(12) United States Patent
Kalayanov et al.

(10) Patent No.: US 9,540,411 B2
(45) Date of Patent: Jan. 10, 2017

(54) HCV POLYMERASE INHIBITORS

(71) Applicant: MEDIVIR AB, Stockholm (SE)

(72) Inventors: Genadiy Kalayanov, Huddinge (SE); Staffan Torssell, Huddinge (SE); Horst Wahling, Huddinge (SE)

(73) Assignee: MEDIVIR AB, Huddinge (SE)

( * ) Notice: Subject to any disclaimer, the term of this patent is extended or adjusted under 35 U.S.C. 154(b) by 0 days.

(21) Appl. No.: 15/210,500

(22) Filed: Jul. 14, 2016

(65) Prior Publication Data

US 2016/0340380 A1 Nov. 24, 2016

Related U.S. Application Data

(63) Continuation of application No. 14/634,449, filed on Feb. 27, 2015, which is a continuation-in-part of
(Continued)

(30) Foreign Application Priority Data

Sep. 4, 2013 (SE) ....................... 1351026
Oct. 3, 2013 (SE) ....................... 1351169
Feb. 12, 2014 (SE) ....................... 1450152

(51) Int. Cl.
*C07H 19/213* (2006.01)
*C07H 19/11* (2006.01)
(Continued)

(52) U.S. Cl.
CPC .......... *C07H 19/213* (2013.01); *C07H 19/073* (2013.01); *C07H 19/11* (2013.01); *C07H 19/173* (2013.01)

(58) Field of Classification Search
None
See application file for complete search history.

(56) References Cited

U.S. PATENT DOCUMENTS

| | | |
|---|---|---|
| 5,484,801 A | 1/1996 | Al-Razzak et al. |
| 5,948,436 A | 9/1999 | Al-Razzak et al. |
| 6,037,157 A | 3/2000 | Norbeck et al. |

FOREIGN PATENT DOCUMENTS

| | | |
|---|---|---|
| CN | 101591371 A | 12/2009 |
| WO | 9414436 A1 | 7/1994 |

(Continued)

OTHER PUBLICATIONS

Beadel et al, Synthesis and Antiviral Evaluation of Alkoxyalkyl Derivatives of 9-(S)-3- Hydroxy-2-phosphonomethxypropyl) adenine against Cytomegalovirus and Orthopoxviruses, J Med Chem, 2006, 49(6):2010-2013.

(Continued)

*Primary Examiner* — Traviss C McIntosh, III
(74) *Attorney, Agent, or Firm* — Gorman IP Law, APC

(57) ABSTRACT

The invention provides compounds of the formula:

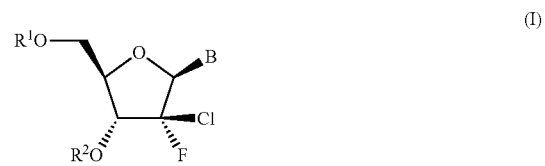

(I)

wherein B is a nucleobase selected from the groups (a) to (d):

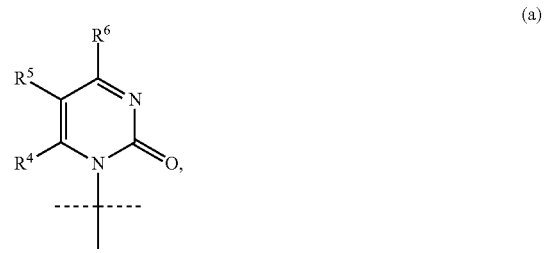

(a)

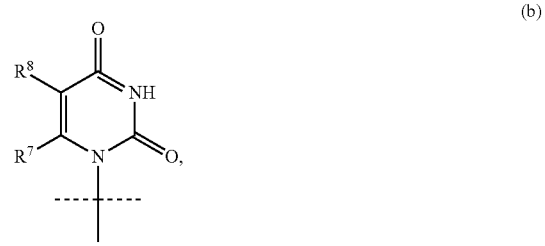

(b)

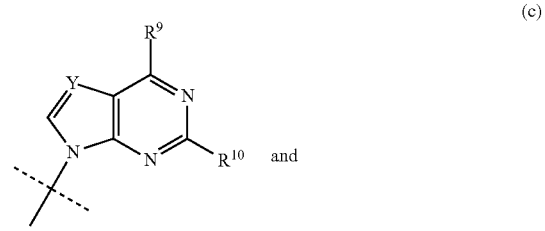

(c) and

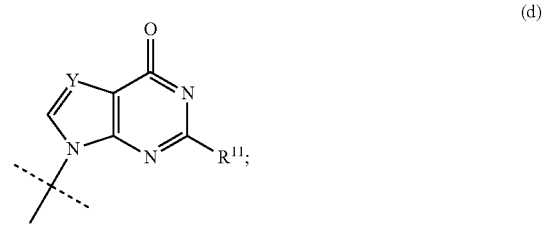

(d)

and the other variables are as defined in the claims, (Continued)

which are of use in the treatment or prophylaxis of hepatitis C virus infection, and related aspects.

17 Claims, No Drawings

Related U.S. Application Data application No. PCT/SE2014/051005, filed on Sep. 2, 2014.

(51) Int. Cl.
*C07H 19/073* (2006.01)
*C07H 19/173* (2006.01)

(56) References Cited

FOREIGN PATENT DOCUMENTS

| WO | 9507696 | A1 | 3/1995 |
|---|---|---|---|
| WO | 9509614 | A1 | 4/1995 |
| WO | 0232920 | A2 | 4/2002 |
| WO | 2007014926 | A1 | 2/2007 |
| WO | 2008082601 | A2 | 7/2008 |
| WO | 2008121634 | A2 | 10/2008 |
| WO | 2009085267 | A1 | 7/2009 |
| WO | 2010075554 | A1 | 7/2010 |
| WO | 2011123672 | A1 | 10/2011 |
| WO | 2012040126 | A1 | 3/2012 |
| WO | 2012142085 | A1 | 10/2012 |
| WO | 2013039920 | A1 | 3/2013 |
| WO | 2013096679 | A1 | 6/2013 |
| WO | 2014078427 | A1 | 5/2014 |
| WO | 2015081133 | A2 | 6/2015 |
| WO | 2015081297 | A1 | 6/2015 |
| WO | WO2015/081297 | * | 6/2015 |
| WO | 2015164812 | A1 | 10/2015 |

OTHER PUBLICATIONS

Blight et al, Efficient Replication of Hepatitis C Virus Genotype 1a RNAs in Cell Culture, Journal of Virology, 2003, 77(5):3181-3190.
David B Smith et al, The Design, Synthesis and Antiviral activity of monofluoro and difluora analogues of 4'-azidocytidine against Hepatitis C virus replication; The discovery of 4'-azado-2'-deoxy-2'fluorcytidine and 4'-azido-2'-dideoxy-2',2'-difluorocytidine, J. Med. Chem., 2009,52,2971-2978; abstract; see compound 2, p. 2971.
Erion et al, Design, Synthesis, and Characterization of a Series of Cytochrome P450 3A-Activated Prodrugs (HepDirect Prodrugs) Useful for Targeting Phosph(on)ate-Based Drugs to the Liver, J. Am. Chem. Soc., 2004, 126 (16):5154-5163.
International Search Report as issued on Nov. 28, 2014 in International Application No. PCT/SE2014/051005.
Krieger et al, Enhancement of Hepatitis C Virus RNA Replication by Cell Culture-Adaptive Mutations, Journal of Virology, 2001, 75:4614-4624.
Kylefjord et al, Transient replication of a hepatitis C virus genotype 1b replicon chimera encoding NS5A-5B from genotype 3a, Journal of Virological Methods, 2014, 195:156-163.
Lawitz et al, Sofosbuvir for Previously Untreated Chronic Hepatitis C Infection, New England Journal of Medicine, 2013, 368:1878-1887.
Lohmann et al, Replication of Subgenomic Hepatitis C Virus in RNAs in a Hepatoma Cell Line, Science, 1999, 285:110-113.
Lohmann et al, Viral and Cellular Determinants of Hepatitis C Virus RNA Replication in Cell Culture, Journal of Virology, 2003, 77(5):3007-3019.
Nomura et al, Synthesis of the Cyclic and Acyclic Acetal Derivatives of 1-(3-C-Ethynyl-B-D-ribo-pentofuranosyl) cytosine, a Potent Antitumor Nucleoside. Design of Prodrugs to be Selectively Activated in Tumor Tissues Via the Bio-Reduction-Hydrolysis Mechanism, Bio-organic & Medicinal Chemistyr, 2003, 11:2453-2461.
PCT International-Type Search Report, Feb. 21, 2014.
Ross et al, Synthesis of Diastereomerically Pure Nucleotide Phosphoramidates, Journal of Organic Chemistry, 2011, 16:8311-8319.
Rudolf K.F. Beran et al, Cellular grown kinetics distinguish a cyclophilin inhibitor from an HSP90 inhibitor as a selective inhibitor of hepatitis C virus PLo2 One, 2012,7,2, e30286,1-8; abstract; see pp. 2-3.
The Merck Index: An Encyclopedia of Chemicals, Drugs, and Biologicals, Fourteenth Edition, Maryadele J. O'Neil, Patricia E. Heckelman, Cherie B. Koch, Kristin J. Roman, Eds. (Merck & Co., Inc., Whitehouse Station, NJ, USA, 2006), Gemcitabine; abstract.
Tong et al, In Vivo Emergence of a Novel Mutant L159F/L320F in the NS5B Polymerase Confers Low-Level Resistance to the HCV Polymerase Inhibitors Mericitabine and Sofosbuvir, Journal of Infectious Disease, 2014, 209 (5):668-675.
Wakita et al, Production of infectious hepatitis C virus in tissue culture from a cloned viral genome, Nat Med., 2005, 11(7):791-796.
Wong et al, Tegobuvir (GS-9190) potency against HCV chimeric replicons derived from consensus NS5B sequences from genotypes 2b, 3a, 4a, 5a, and 6a, Virology, 2012, 429(1) 57-62.

* cited by examiner

SEQUENCE LISTING

<160> NUMBER OF SEQ ID NOS: 1

<210> SEQ ID NO 1
<211> LENGTH: 36
<212> TYPE: RNA
<213> ORGANISM: Artificial Sequence
<220> FEATURE:
<223> OTHER INFORMATION: Biotinylated RNA template

<400> SEQUENCE: 1
uuuuuuuuuu agucagucgg cccgguuuuc cgggcc                36

HCV POLYMERASE INHIBITORS

CROSS-REFERENCE TO RELATED APPLICATIONS

This Nonprovisional application is a Continuation application of co-pending application Ser. No. 14/634,449 filed on Feb. 27, 2015, which is a Continuation-In-Part application of PCT International Application No. PCT/SE2014/051005 filed on Sep. 2, 2014, which claims priority under 35 U.S. C. §119 on Patent Application No. 1351026-8 filed in Sweden on Sep. 4, 2013, on Patent Application No. 1351169-6 filed in Sweden on Oct. 3, 2013, and on Patent Application No. 1450152-2 filed in Sweden on Feb. 12, 2014, the entire contents of each of which are hereby incorporated by reference.

TECHNICAL FIELD

The present invention relates to nucleoside derivatives which are inhibitors of the polymerase of hepatitis C virus (HCV). The invention further relates to prodrugs of the nucleoside derivatives, compositions comprising them, and methods for their use in the treatment or prophylaxis of HCV infection.

BACKGROUND OF THE INVENTION

HCV is a single stranded, positive-sense RNA virus belonging to the Flaviviridae family of viruses in the hepacivirus genus. The NS5B region of the RNA polygene encodes an RNA dependent RNA polymerase (RdRp), which is essential to viral replication. Following the initial acute infection, a majority of infected individuals develop chronic hepatitis because HCV replicates preferentially in hepatocytes but is not directly cytopathic. In particular, the lack of a vigorous T-lymphocyte response and the high propensity of the virus to mutate appear to promote a high rate of chronic infection. Chronic hepatitis can progress to liver fibrosis, leading to cirrhosis, end-stage liver disease and HCC (hepatocellular carcinoma), making it the leading cause of liver transplantations.

There are six major HCV genotypes and more than 50 subtypes, which are differently distributed geographically. HCV genotype 1 is the predominant genotype in Europe and in the US. The extensive genetic heterogeneity of HCV has important diagnostic and clinical implications, perhaps explaining difficulties in vaccine development and the lack of response to current therapy.

Transmission of HCV can occur through contact with contaminated blood or blood products, for example following blood transfusion or intravenous drug use. The introduction of diagnostic tests used in blood screening has led to a downward trend in post-transfusion HCV incidence. However, given the slow progression to the end-stage liver disease, the existing infections will continue to present a serious medical and economic burden for decades.

The first generation HCV therapies were based on (pegylated) interferon-alpha (IFN-α) in combination with ribavirin. This combination therapy yields a sustained virologic response in more than 40% of patients infected by genotype 1 viruses and about 80% of those infected by genotypes 2 and 3. Beside the limited efficacy on HCV genotype 1, this combination therapy has significant side effects and is poorly tolerated in many patients. Major side effects include influenza-like symptoms, hematologic abnormalities and neuropsychiatric symptoms. The second generation of HCV treatments added the HCV protease inhibitors telepravir or boceprevir, allowing treatment times to be shortened, but generating a significant number of serious side-effects. A major improvement in treatment was possible with the introduction of the protease inhibitor simeprevir and the HCV polymerase inhibitor sofosbuvir. These were initially co-administered with interferon and ribavirin, but more recently the co-administration of simeprevir (WO2007/014926) and sofosbuvir (WO2008/121634) has allowed interferon-free and ribavirin-free HCV treatment with further diminished treatment times and dramatically decreased side effects.

An advantage of nucleoside/nucleotide HCV polymerase inhibitors such as sofosbuvir, is that they tend to be active against several of the HCV genotypes. Sofosbuvir for example has been approved by the FDA and EMA for treatment of HCV genotypes 1 and 4. However, in the Fission phase III clinical trials reported in Lawitz et al, N. Eng. J. Med. 2013; 368:1878-87, it was noted "Response rates in the sofosbuvir-ribavirin group were lower among patients with genotype 3 infection than amongst those with genotype 2 infection (56% vs. 97%)". Hence there is a need for more effective, convenient and better-tolerated treatments.

Experience with HIV drugs, in particular with HIV protease inhibitors, has taught that sub-optimal pharmacokinetics and complex dosing regimes quickly result in inadvertent compliance failures. This in turn means that the 24 hour trough concentration (minimum plasma concentration) for the respective drugs in an HIV regime frequently falls below the $IC_{90}$ or $ED_{90}$ threshold for large parts of the day. It is considered that a 24 hour trough level of at least the $IC_{50}$, and more realistically, the $IC_{90}$ or $ED_{90}$, is essential to slow down the development of drug escape mutants. Achieving the necessary pharmacokinetics and drug metabolism to allow such trough levels provides a stringent challenge to drug design.

The NS5B RdRp is absolutely essential for replication of the single-stranded, positive sense HCV RNA genome which makes it an attractive target for the development of antiviral compounds. There are two major classes of NS5B inhibitors: non-nucleoside inhibitors (NNIs) and nucleoside analogues. The NNIs bind to allosteric regions of the protein whereas the nucleoside inhibitors are anabolized to the corresponding nucleotide and act as alternative substrate for the polymerase. The formed nucleotide is then incorporated in the nascent RNA polymer chain and can terminate the growth of the polymer chain. To date, both nucleoside and non-nucleoside inhibitors of NS5B are known.

As stated above, the inhibition mechanism of nucleoside inhibitors involves phosphorylation of the nucleoside to the corresponding triphosphate. The phosphorylation is commonly mediated by host cell kinases and is an absolute requirement for the nucleoside to be active as an alternative substrate for the NS5B polymerase. Typically, the first phosphorylation step, i.e. conversion of the nucleoside to the nucleoside 5'-monophosphate is the rate limiting step. Subsequent conversion of the monophosphate to the di- and tri-phosphate usually proceed facile and are usually not rate limiting. A strategy for increasing nucleoside triphosphate production is to use cell permeable nucleoside prodrugs of the monophosphate, i.e. a nucleoside carrying a masked phosphate moiety, a "prodrug moiety", which are susceptible to intracellular enzymatic activation leading to a nucleoside monophosphate. The thus formed monophosphate is subsequently converted to the active triphosphate by cellular kinases.

Chemical modifications of an active compound to afford a potential prodrug produces an entirely new molecular entity which can exhibit undesirable physical, chemical and biological properties, thus the identification of optimal prodrugs remains an uncertain and challenging task.

There is a need for HCV inhibitors that may overcome the disadvantages of current HCV therapy such as side effects e.g. toxicity, limited efficacy, lack of pan-genotypic coverage, the emerging of resistance, and compliance failures, as well as improve the sustained viral response.

The present invention provides new HCV inhibiting compounds which have useful properties regarding one or more of the following parameters: antiviral efficacy; pan-genotypic coverage; favourable profile of resistance development; lack of toxicity and genotoxicity; favourable pharmacokinetics and pharmacodynamics; and ease of formulation and administration. The skilled person will appreciate that an HCV inhibiting compound of the present invention need not demonstrate an improvement in every respect over all known compounds but may instead provide a balance of properties which in combination mean that the HCV inhibiting compound is a valuable alternative pharmaceutical agent.

Compounds of the invention may also be attractive due to the fact that they lack activity against other viruses, i.e. are selective, in particular against HIV. HIV infected patients often suffer from co-infections such as HCV. Treatment of such patients with an HCV inhibitor that also inhibits HIV may lead to the emergence of resistant HIV strains.

DESCRIPTION OF THE INVENTION

In one aspect, the present invention provides compounds represented by formula I:

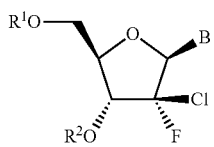
(I)

wherein:
B is a nucleobase selected from the groups (a) to (d):

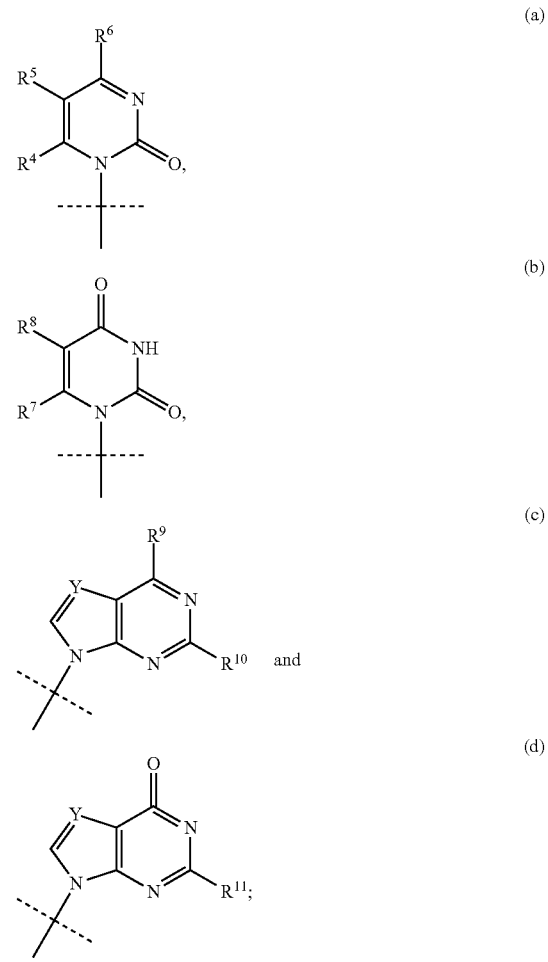

wherein Y is N or —C($R^{19}$)—;
$R^1$ is H, C(=O)$R^{30}$, C(=O)CH$R^{31}$NH$_2$, C$R^{32}R^{32'}$OC(=O) CH$R^{33}$NH$_2$, or $R^1$ is selected from the groups (i) to (vi):

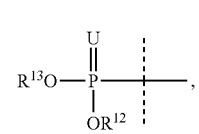
(i)

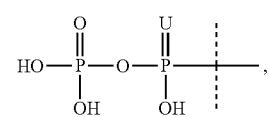
(ii)

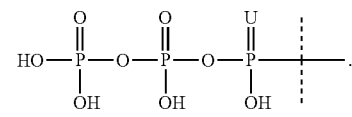
(iii)

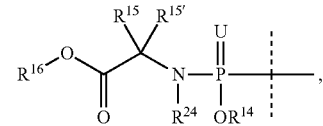
(iv)

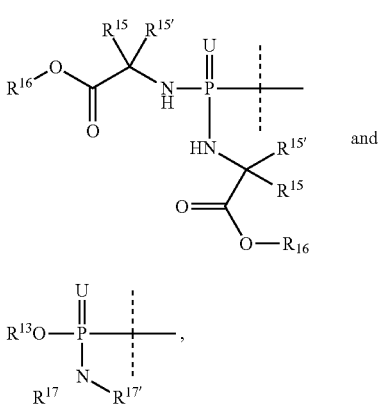

(v)

(vi)

$R^2$ is H, $C(=O)R^{30}$, $C(=O)CHR^{31}NH_2$, $CR^{32}R^{32'}OC(=O)CHR^{33}NH_2$ or $CR^{32}R^{32'}OC(=O)R^{30}$; or $R^1$ and $R^2$ together form a bivalent linker of formula:

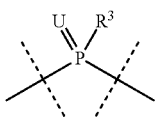

$R^3$ is OH, $C_1$-$C_6$alkoxy, $C_3$-$C_7$cycloalkoxy, $C_3$-$C_7$cycloalkyl$C_1$-$C_3$alkoxy, benzyloxy, O—($C_1$-$C_6$alkylene)-T-$R^{21}$ or $NHC(R^{15})(R^{15'})C(=O)R^{16}$;

$R^4$, $R^5$, $R^7$ and $R^8$ are each independently H, $C_1$-$C_6$alkyl, $C_1$-$C_6$haloalkyl, $C_1$-$C_6$hydroxyalkyl, halo, —$OR^{18}$, —$SR^{18}$ or —$N(R^{18})_2$;

$R^6$, $R^9$, $R^{10}$, $R^{11}$ are each independently selected from H, $C_1$-$C_6$alkyl, $C_2$-$C_6$alkenyl, $C_2$-$C_6$alkynyl, $C_3$-$C_7$cycloalkyl, $C_1$-$C_6$haloalkyl, $C_1$-$C_6$hydroxyalkyl, halo, $OR^{18}$, $SR^{18}$, $N(R^{18})_2$, —$NHC(O)OR^{18}$, —$NHC(O)N(R^{18})_2$, —CN, —$NO_2$, —$C(O)R^{18}$, —$C(O)OR^{18}$, —$C(O)N(R^{18})_2$ and —$NHC(O)R^{18}$, wherein said $C_2$-$C_6$alkenyl group and said $C_2$-$C_6$alkynyl group can be optionally substituted with halo or $C_3$-$C_5$cycloalkyl;

$R^{12}$ is H or —($C_1$-$C_6$alkylene)-T-$R^{21}$, phenyl, indolyl or naphthyl which phenyl, indolyl or naphthyl group is optionally substituted with 1, 2 or 3 substituents each independently selected from halo, $C_1$-$C_6$alkyl, $C_2$-$C_6$alkenyl, $C_1$-$C_6$haloalkyl, hydroxy$C_1$-$C_6$alkyl, $C_3$-$C_6$cycloalkyl, $C_1$-$C_6$alkylcarbonyl, $C_3$-$C_6$cycloalkyl carbonyl $C_1$-$C_6$alkoxy, $C_1$-$C_6$haloalkoxy, hydroxy and amino;

$R^{13}$ is H or —($C_1$-$C_6$alkylene)-T-$R^{21}$; or $R^{12}$ and $R^{13}$ can join to form a $C_2$-$C_4$alkylene group between the oxygen atoms to which they are attached, wherein said $C_2$-$C_4$alkylene group is optionally substituted with one $C_6$-$C_{10}$aryl group;

$R^{14}$ is H or $C_1$-$C_6$alkyl, phenyl, naphthyl or a 5 to 12 membered mono or bicyclic heteroaryl containing 1, 2 or 3 heteroatoms independently selected from N, O and S, which phenyl, naphthyl or heteroaryl is optionally substituted with 1, 2 or 3 $R^{22}$;

$R^{15}$ and $R^{15'}$ are each independently selected from H, $C_1$-$C_6$alkyl, $C_3$-$C_7$cycloalkyl, $C_3$-$C_7$cycloalkyl$C_1$-$C_3$alkyl, phenyl and benzyl, or $R^{15}$ and $R^{15'}$ together with the carbon atom to which they are attached from a $C_3$-$C_7$cycloalkylene group, wherein each $C_1$-$C_6$alkyl is optionally substituted with a group selected from halo, $OR^{18}$ and $SR^{18}$, and each $C_3$-$C_7$cycloalkyl, $C_3$-$C_7$cycloalkylene, phenyl and benzyl is optionally substituted with one or two groups independently selected from $C_1$-$C_3$alkyl, halo and $OR^{18}$; or $R^{15'}$ is H and $R^{15}$ and $R^{24}$ together with the atoms to which they are attached, form a 5-membered ring;

$R^{16}$ is H, $C_1$-$C_{10}$alkyl, $C_2$-$C_{10}$alkenyl, $C_3$-$C_7$cycloalkyl, $C_3$-$C_7$cycloalkyl$C_1$-$C_3$alkyl, benzyl, phenyl or adamantyl, any of which is optionally substituted with 1, 2 or 3 groups, each independently selected from halo, $OR^{18}$ and $N(R^{18})_2$;

each $R^{17}$ is independently selected from H, $C_1$-$C_6$alkyl, $C_2$-$C_6$alkenyl, $C_2$-$C_6$alkynyl, $C_1$-$C_6$haloalkyl, $C_3$-$C_7$cycloalkyl, $C_3$-$C_7$cycloalkenyl, phenyl and benzyl; or both $R^{17}$ together with the nitrogen atom to which they are attached form a 3-7 membered heterocyclic or a 5-6 membered heteroaryl ring which rings are optionally substituted with one or two groups independently selected from $C_1$-$C_3$alkyl, halo, $C_1$-$C_3$haloalkyl, amino, $C_1$-$C_3$alkylamino, $(C_1$-$C_3$alkyl$)_2$amino;

each $R^{18}$ is independently H, $C_1$-$C_6$alkyl, $C_1$-$C_6$haloalkyl or $C_3$-$C_7$cycloalkyl;

$R^{19}$ is H, $C_1$-$C_6$alkyl, $C_2$-$C_6$alkenyl, $C_2$-$C_6$alkynyl, $C_3$-$C_7$cycloalkyl, $C_1$-$C_6$haloalkyl, $C_1$-$C_6$hydroxyalkyl, halo, —$OR^{18}$ or $N(R^{18})_2$;

each $R^{20}$ is independently H, $C_1$-$C_6$alkyl, $C_1$-$C_6$haloalkyl, $C_3$-$C_7$cycloalkyl, $C_1$-$C_6$hydroxyalkyl or $C_3$-$C_7$cycloalkyl$C_1$-$C_3$alkyl;

each $R^{21}$ is independently H, $C_1$-$C_{24}$alkyl, $C_1$-$C_6$haloalkyl, $C_1$-$C_6$hydroxyalkyl, $C_2$-$C_6$alkenyl, $C_2$-$C_6$alkynyl, $C_3$-$C_7$cycloalkyl or $C_3$-$C_7$cycloalkenyl;

each $R^{22}$ is independently selected from halo, $C_1$-$C_6$alkyl, $C_2$-$C_6$alkenyl, $C_1$-$C_6$haloalkyl, phenyl, hydroxy$C_1$-$C_6$alkyl, $C_3$-$C_6$cycloalkyl, $C_1$-$C_6$alkylcarbonyl, $C_3$-$C_6$cycloalkylcarbonyl, carboxy$C_1$-$C_6$alkyl, oxo (required to make flavone), $OR^{20}$, $SR^{20}$, $N(R^{20})_2$, CN, $NO_2$, $C(O)OR^{20}$, $C(O)N(R^{20})_2$ and $NHC(O)R^{20}$, or any two $R^{22}$ groups attached to adjacent ring carbon atoms can combine to form —O—$R^{23}$—O—;

$R^{23}$ is —$[C(R^{33})_2]_n$—;

$R^{24}$ is H, or $R^{24}$ and $R^{15}$ together with the atoms to which they are attached, form a 5-membered ring;

each $R^{30}$ is independently selected from $C_1$-$C_6$alkyl and $C_1$-$C_6$alkoxy;

each $R^{31}$ is independently selected from H, $C_1$-$C_6$alkyl, $C_3$-$C_7$cycloalkyl and benzyl;

each $R^{32}$ and $R^{32'}$ is independently selected from H and $C_1$-$C_3$alkyl;

each $R^{33}$ is independently selected from H and $C_1$-$C_6$alkyl;

U is O or S;

each T is independently —S—, —O—, —SC(O)—, —C(O)S—, —SC(S)—, —C(S)S—, —OC(O)—, —C(O)O— and —OC(O)O—;

or a pharmaceutically acceptable salt and/or solvate thereof.

The compounds of formula I may optionally be provided in the form of a pharmaceutically acceptable salt and/or solvate. In one embodiment the compound of the invention is provided in the form of a pharmaceutically acceptable salt. In a second embodiment the compound of the invention is provided in the form of a pharmaceutically acceptable solvate. In a third embodiment the compound of the invention is provided in its free form.

In one aspect, the invention includes prodrugs. In a typical configuration, the prodrug group is located at the 3'- and/or the 5'-position of the sugar moiety. Suitable groups for this purpose include esters, i.e. groups of the formula OC(=O)$R^{30}$ wherein $R^{30}$ typically is $C_1$-$C_4$alkyl, and amino acid esters, i.e. groups of the formula OC(=O)CHR$^{31}$NH$_2$ wherein $R^{31}$ typically is $C_1$-$C_6$alkyl. Further suitable prodrug groups are phosphate prodrugs, i.e. a prodrug group which in vivo is converted to a phosphate. Prodrug group(s) may also be present on the nucleobase B.

In one embodiment of the invention, B is the group (a). Typically in this embodiment, the group B is of the formula (a'):

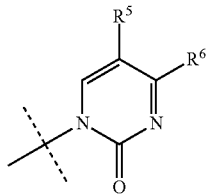

wherein $R^5$ is H or F, and $R^6$ is $N(R^{18})_2$ or NHCOC$_1$-C$_6$alkyl. Typically $R^6$ is NH$_2$.

In a further typical embodiment of the invention, B is of the group (a''):

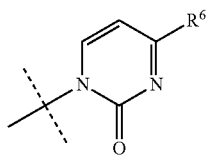

wherein $R^6$ is $N(R^{18})_2$ or NHCOC$_1$-C$_6$alkyl. Typically $R^6$ is NH$_2$.

In a second embodiment of the invention, B is the group (b). Typically in this embodiment, the group B is of the formula b':

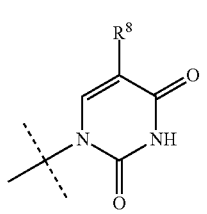

wherein $R^8$ is H or F. Typically $R^8$ is H

In a third embodiment of the invention B is the group (c').

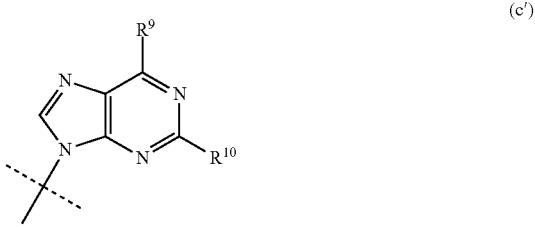

wherein $R^9$ is OH or $C_1$-$C_6$alkoxy, and $R^{10}$ is NH$_2$ or NHCOC$_1$-$C_6$alkyl.

In a fourth embodiment of the invention B is the group (d).

In one embodiment of the invention, $R^2$ is H.

In alternative embodiments of the invention, $R^2$ is C(=O)$R^{30}$, C(=O)CHR$^{31}$NH$_2$ or OCR$^{32}$R$^{32'}$OC(=O)CHR$^{33}$NH$_2$.

In embodiments of the invention where $R^2$ is C(=O)$R^{30}$, $R^{30}$ is typically methyl, isopropyl, isobutyl or sec-butyl, especially isopropyl. In embodiments of the invention where $R^2$ is C(=O)CHR$^{31}$NH$_2$, $R^{31}$ suitably corresponds to the side chain of a natural or non-natural amino acid, such as the side chain of glycine (Gly), alanine (Ala), valine (Val), isoleucine (Ile) or phenylalanine (Phe), i.e. $R^{31}$ is H, methyl, isopropyl, isobutyl or benzyl respectively, especially isopropyl. Of particular interest are amino acid ester moieties wherein the configuration at the asymmetric carbon atom to which $R^{31}$ is attached is that of an L-amino acid, in particular L-Ala, L-Val, L-Ile, and L-Phe, especially L-valine, i.e. $R^{31}$ is isopropyl. In embodiments of the invention where $R^2$ is OCR$^{32}$R$^{32'}$OC(=O)CHR$^{33}$NH$_2$, $R^{32}$ and $R^{32'}$ may be the same or different and are typically selected from H and methyl, with $R^{33}$ typically being $C_1$-$C_3$alkyl.

In one embodiment of the invention, $R^1$ is H.

In alternative embodiments of the invention $R^1$ is a prodrug moiety. Suitably according to these embodiments $R^1$ is C(=O)$R^{30}$, C(=O)CHR$^{31}$NH$_2$ or OCR$^{32}$R$^{32'}$OC(=O)CHR$^{33}$NH$_2$.

In embodiments of the invention where $R^1$ is C(=O)$R^{30}$, $R^{30}$ is typically methyl, isopropyl, isobutyl or sec-butyl, especially isopropyl. In embodiments of the invention where $R^1$ is C(=O)CHR$^{31}$NH$_2$, $R^{31}$ suitably corresponds to the side chain of a natural or non-natural amino acid, such as the side chains of glycine (Gly), alanine (Ala), valine (Val), isoleucine (Ile) or phenylalanine (Phe), i.e. $R^{31}$ is H, methyl, isopropyl, isobutyl or benzyl respectively, especially isopropyl. Of particular interest are amino acid ester moieties wherein the configuration at the asymmetric carbon atom to which $R^{31}$ is attached is that of an L-amino acid, in particular L-Ala, L-Val, L-Ile, and L-Phe, especially L-valine, i.e. $R^{31}$ is isopropyl. $R^{31}$ may also be sec-butyl. In embodiments of the invention where $R^1$ is OCR$^{32}$R$^{32'}$OC(=O)CHR$^{33}$NH$_2$, $R^{32}$ and $R^{32'}$ may be the same or different and are typically selected from H and methyl, with $R^{33}$ typically being H or $C_1$-$C_3$alkyl.

In one embodiment of the invention, $R^1$ and $R^2$ form together a bivalent linker of the formula:

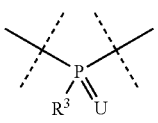

wherein $R^3$ is as defined above, thus providing compounds of the formula:

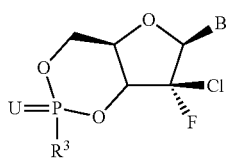

Typically according to this embodiment, U is O.

Representative configurations for $R^3$ include $C_1$-$C_6$alkoxy and $NHC(R^{15})(R^{15'})C(=O)R^{16}$.

Typically, $R^3$ is $C_1$-$C_3$alkoxy, such as isopropoxy or methoxy.

A further typical configuration for $R^3$ is $NHC(R^{15})(R^{15'})C(=O)R^{16}$.

Typically in this configuration, $R^{15}$ and $R^{15'}$ are each independently selected from H, $C_1$-$C_6$alkyl and benzyl. Typically, one of $R^{15}$ and $R^{15'}$ is H and the other is the side chain of an amino acid, such as the side chain of alanine, valine, leucine or isoleucine, i.e. methyl, isopropyl, isobutyl or 1-methylprop-1-yl respectively. In a preferred configuration, one of $R^{15}$ and $R^{15'}$ is H and the other is methyl.

$R^{16}$ is typically straight or branched $C_1$-$C_6$alkyl or $C_3$-$C_7$cycloalkyl. Typically $R^{16}$ is isopropyl.

A representative value for $R^3$ is $NHCH(C_1$-$C_6$alkyl$)C(=O)$ $C_1$-$C_3$alkyl.

An alternative configuration for $R^3$ is $O-(C_1$-$C_6$alkylene$)$-T-$R^{21}$, wherein the $C_1$-$C_6$alkylene moiety is linear or branched.

In one embodiment of compounds of formula (I), $R^1$ is the group (i):

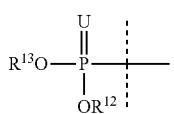

Preferably in compounds according to this embodiment, U is O.

In one configuration of the group (i), $R^{13}$ is H and $R^{12}$ is $(C_1$-$C_6$alkylene$)$-T-$R^{21}$, typically in this configuration, $R^{12}$ is ethylene, T is O and $R^{21}$ is $C_{12}$-$C_{19}$, thus forming the structure (i-a):

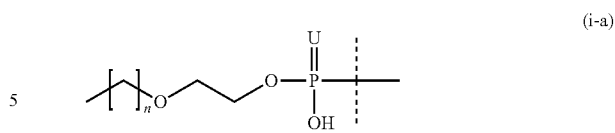

wherein n is an integer from 11 to 23, such as from 11 to 18. Preferably n is an integer from 15 to 16.

Typically in the group (i-a), U is O.

Typically in compounds of formula (I) wherein $R^1$ is the group (i-a), $R^2$ is H.

In an alternative configuration of the group (i), $R^{12}$ and $R^{13}$ join to form an optionally substituted $C_2$-$C_4$alkylene group between the oxygen atoms to which they are attached, thus forming a cyclic phosphate. Typically, the alkylene group is a $C_3$alkylene, thus providing the structure (i-b):

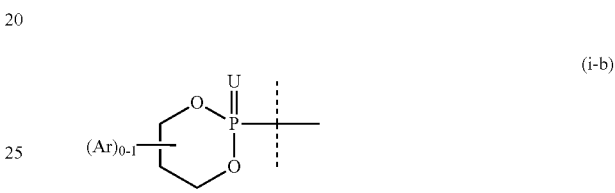

Typically U is O and Ar is phenyl which is optionally substituted with one or two substituents independently selected from halo, $C_1$-$C_6$alkyl, $C_1$-$C_6$haloalkyl, $C_1$-$C_6$alkoxy and cyano, typically halo. Representative examples of Ar include phenyl and phenyl which is substituted with chloro in the meta position.

Typically in compounds of formula (I) wherein $R^1$ is the group (i-b), $R^2$ is H.

In a further configuration of the group (i), $R^{13}$ is $(C_1$-$C_6$alkylene$)$-T-$R^{21}$, thus providing the group (i-c):

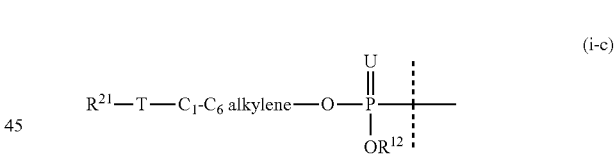

wherein the $C_1$-$C_6$alkylene moiety is linear or branched. Non-limiting examples of the $C_1$-$C_6$alkylene moiety in the group (i-c) include methylene, ethylene, isopropylene and dimethylmethylene.

Typically in the group (i-c), U is O.

In a typical subgroup of the group (i-c), U is O, $C_1$-$C_6$alkylene is methylene and T is —C(O)O—, or the $C_1$-$C_6$alkylene is ethylene and T is —C(O)S— thus providing compounds of formula I having any one of the partial structures (i-c1) or (i-c2) respectively:

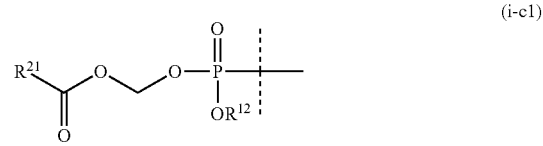

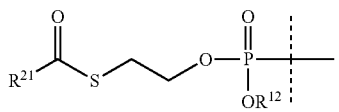

(i-c2)

wherein $R^{21}$ is $C_1$-$C_6$alkyl, such as tert-butyl. $R^{12}$ in these structures is typically the same group as $R^{13}$, or alternatively, $R^{12}$ is as defined above.

Typically in compounds of formula (I) wherein $R^1$ is the group (i-c), $R^2$ is H.

In a further embodiment of compounds of formula (I), $R^1$ is the group (iii), i.e. $R^1$ together with the oxygen atom to which is attached, form a triphosphate, or a tri-thiophosphate, thus providing compounds having the structure:

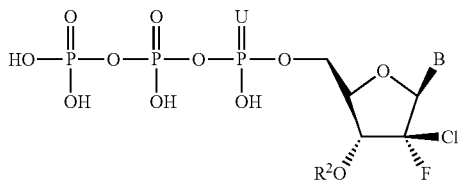

or a pharmaceutically acceptable salt thereof, such as the potassium salt or the sodium salt. In preferred configurations according to these embodiments, U is O.

Typically according to this embodiment, $R^2$ is H.

In a preferred embodiment, the invention provides a compound of the formula:

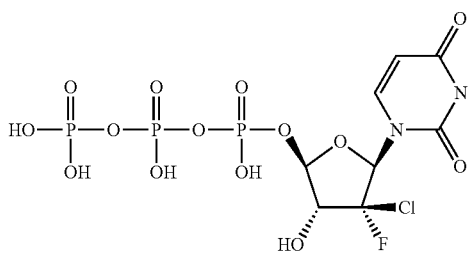 [SMILES: O=c1ccn([C@@H]2O[C@H](OP(=O)(O)OP(=O)(O)OP(=O)(O)O)[C@@H](O)[C@]2(F)Cl)c(=O)[nH]1]

In a further embodiment of compounds of formula (I), $R^1$ is the group (iv):

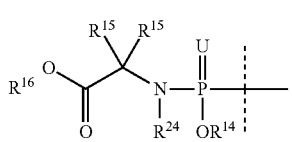

(iv)

In typical compounds of formula (I) wherein $R^1$ is the group (iv) and one of $R^{15}$ and $R^{15'}$ is H, the stereochemistry is as indicated in the partial formula:

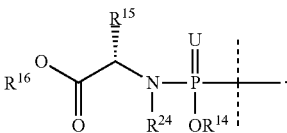

U is typically O.

$R^{24}$ is typically H.

Representative examples of $R^{14}$ include phenyl which is optionally substituted with one or two $R^{22}$, wherein each $R^{22}$ is independently selected from halo, $C_1$-$C_6$alkyl, $C_2$-$C_6$alkenyl and $OR^{20}$ and $R^{20}$ is $C_1$-$C_6$alkyl; or $R^{14}$ is naphthyl.

Typically according to this embodiment, U is O, $R^{24}$ is H and $R^{14}$ is phenyl which is optionally substituted with 1, 2 or 3 $R^{22}$, thus providing the group (iv-a):

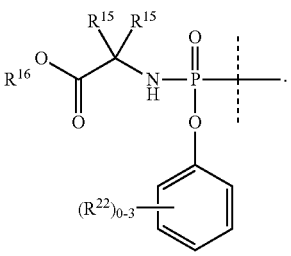

(iv-a)

In a typical configuration of the group (iv-a), the phenyl is substituted with one or two halo, such as chloro or fluoro.

In a further representative configuration of group (iv-a), the phenyl is substituted with one $R^{22}$ which is selected from $C_3$-$C_6$cycloalkyl, $C_1$-$C_6$alkylcarbonyl or $C_3$-$C_6$cycloalkylcarbonyl, the cycloalkyl moiety being optionally substituted with $C_1$-$C_3$ alkyl.

In a further representative configuration of group (iv-a), the phenyl is substituted with two $R^{22}$, whereof one $R^{22}$ is selected from $C_3$-$C_6$cycloalkyl, $C_1$-$C_6$alkylcarbonyl or $C_3$-$C_6$cycloalkylcarbonyl, the cycloalkyl moiety being optionally substituted with $C_1$-$C_3$alkyl, and the other $R^{22}$ is methyl, cyclopropyl, fluoro or chloro.

A further representative value for $R^{14}$ is phenyl which is substituted with two $R^{22}$ located on adjacent carbon atoms and the two $R^{22}$ combine to form —O—$CH_2$—O—, thus forming the partial structure:

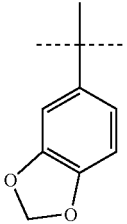

A further representative configuration of $R^{14}$ is phenyl which is substituted with $R^{22}$ and $R^{22}$ is carboxy$C_1$-$C_6$alkyl, and $R^{24}$ is H. A representative example of this configuration is illustrated in formula (iv-b)

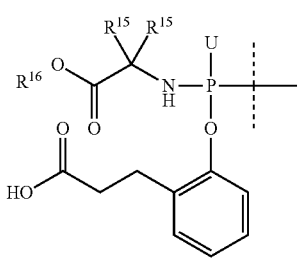

(iv-b)

Typically in the group (iv-b), U is O.

In one configuration of the group (iv), $R^{14}$ is phenyl which is fused to a 4-membered heterocyclic ring, which ring is substituted with keto and phenyl. Typical such structures are as shown in the partial formulae below:

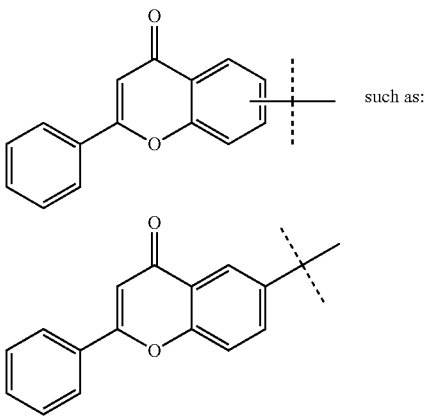

Further representative values for $R^{14}$ include indolyl, typically 5-indolyl.

In one embodiment, $R^{14}$ is heteroaryl, which heteroaryl is a 5 to 12 membered mono or bicyclic aromatic ring containing 1, 2 or 3 heteroatoms independently selected from N, O and S, and which heteroaryl is optionally substituted with 1, 2 or 3 $R^{22}$. Typically in this embodiment, each $R^{22}$ is independently selected from $C_1$-$C_6$alkyl, $C_2$-$C_6$alkenyl, $C_1$-$C_6$haloalkyl, $C_1$-$C_6$alkoxy, hydroxy and amino.

A representative value for $R^{14}$ according to this embodiment is optionally substituted pyridyl.

Typical compounds according to this embodiment are those wherein U is O and $R^{14}$ is pyridyl which is optionally substituted with one or two substituents each independently selected from halo, $C_1$-$C_6$haloalkyl, $C_1$-$C_6$alkyl, $C_2$-$C_6$alkenyl, $C_1$-$C_6$alkoxy, hydroxy, amino.

Typically in compounds of formula (I) wherein $R^1$ is the group (iv), or any subgroup thereof, the moiety $N(R^{24})C(R^{15})(R^{15'})$—$C(=O)OR^{16}$ forms an amino acid ester residue, including natural and non-natural amino acid residues. Typically one of $R^{15}$ and $R^{15'}$ is hydrogen, and the other one is hydrogen or $C_1$-$C_6$alkyl, such as isopropyl or isobutyl. Of particular interest are amino acid residues wherein $R^{15'}$ is hydrogen, examples are glycine, (Gly) alanine (Ala), valine (Val), isoleucine (Ile) and phenylalanine (Phe) residues, i.e., $R^{15'}$ is H and $R^{15}$ is methyl, isopropyl, isobutyl or benzyl respectively. In compounds wherein $R^{15'}$ is hydrogen and $R^{15}$ is other than hydrogen, the configuration at the asymmetric carbon atom is typically that of an L-amino acid, in particular L-Ala, L-Val, L-Ile, and L-Phe.

In a typical configuration of the group (iv), one of $R^{15}$ and $R^{15'}$ is H and the other is methyl.

In a further configuration of the group (iv), $R^{15}$ and $R^{15'}$ together with the carbon atom to which they are attached form $C_3$-$C_7$cycloalkyl, for example cyclopropyl or cyclobutyl.

In a typical configuration of group (iv) $R^{16}$ is $C_1$-$C_{10}$alkyl.

In one configuration of group (iv), $R^{16}$ is $C_1$-$C_3$alkyl, such as methyl, ethyl, propyl, isopropyl, preferably isopropyl.

In a further configuration of group (iv), $R^{16}$ is $C_1$-$C_8$alkyl, such as 2-ethylbutyl, 2-pentyl, 2-butyl, isobutyl, tert-pentyl, preferably 2-ethylbutyl.

In a further configuration of group (iv), $R^{16}$ is $C_3$-$C_7$cycloalkyl, such as cyclohexyl.

In one embodiment of compounds of formula (I), $R^1$ is the group (iv) wherein

U is O $R^{24}$ is H, $R^{14}$ is phenyl which is substituted with $C_3$-$C_6$cycloalkyl, $C_1$-$C_6$alkylcarbonyl or a 5- or 6-membered heteroaryl, $R^{15}$ is H, $R^{15'}$ is $C_1$-$C_3$alkyl, such as methyl, ethyl or isopropyl, and $R^{16}$ is $C_1$-$C_6$alkyl or $C_3$-$C_7$cycloalkyl, such as cyclopropyl, cyclobutyl or cyclopentyl.

In one embodiment of compounds of formula (I), $R^1$ is the group (iv) wherein $R^{24}$ is H, $R^{14}$ is optionally substituted phenyl or naphthyl;

$R^{15}$ and $R^{15'}$ are each independently H or $C_1$-$C_6$alkyl, and $R^{16}$ is $C_1$-$C_8$alkyl or $C_3$-$C_7$cycloalkyl.

In a typical configuration of $R^1$ according to this embodiment $R^{24}$ is H, $R^{14}$ is optionally substituted phenyl;

One of $R^{15}$ and $R^{15'}$ is H, and the other one is $C_1$-$C_3$alkyl, and $R^{16}$ is $C_1$-$C_8$alkyl.

In a typical embodiment the invention includes compounds wherein

B is the group b';

U is O;

$R^1$ is the group (iv);

$R^2$ is H;

$R^8$ is H;

$R^{14}$ is optionally substituted phenyl;

one of $R^{15}$ and $R^{15'}$ is H is and the other is $C_1$-$C_3$alkyl;

$R^{16}$ is $C_1$-$C_8$alkyl.

In a preferred embodiment, the invention provides a compound of the formula:

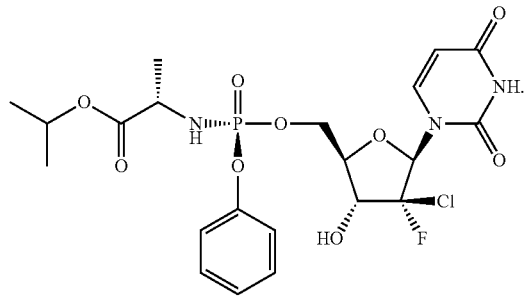 [SMILES: CC(C)OC(=O)[C@H](C)N[P@](=O)(OC[C@H]1O[C@@H](n2ccc(=O)[nH]c2=O)[C@@](F)(Cl)[C@@H]1O)Oc1ccccc1]

In a further preferred embodiment, the invention provides a compound of the formula:

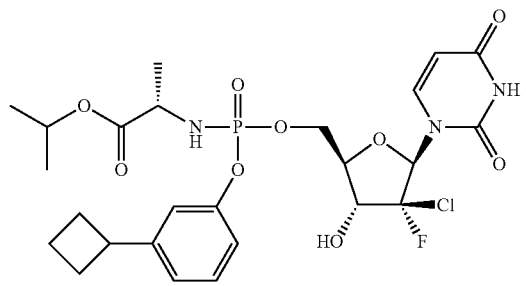 [SMILES: CC(C)OC(=O)[C@H](C)NP(=O)(OC[C@H]1O[C@@H](n2ccc(=O)[nH]c2=O)[C@@](F)(Cl)[C@@H]1O)Oc1cccc(C2CCC2)c1]

the compound being a single stereoisomer at the phosphorus atom.

In a further preferred embodiment, the invention provides a compound of the formula:

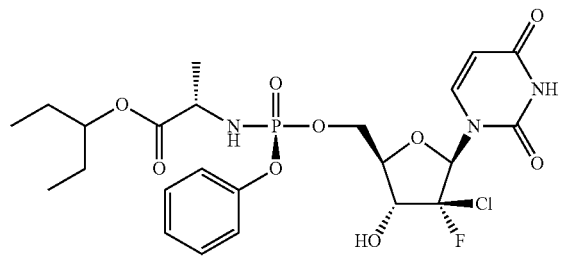 [SMILES: CCC(CC)OC(=O)[C@H](C)N[P@](=O)(OC[C@H]1O[C@@H](n2ccc(=O)[nH]c2=O)[C@@](F)(Cl)[C@@H]1O)Oc1ccccc1]

the compound being a single stereoisomer at the phosphorus atom.

In a further preferred embodiment, the invention provides a compound of the formula:

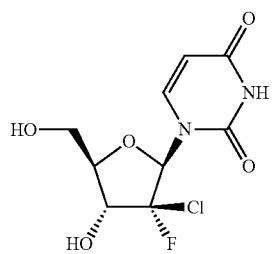 [SMILES: O=c1ccn([C@@H]2O[C@H](CO)[C@@H](O)[C@]2(F)Cl)c(=O)[nH]1]

In an alternative configuration of the group (iv), $R^{15}$ is H, and $R^{15'}$ and $R^{24}$ together with the atoms to which they are attached form a pyrrolidine ring, thus affording the group (iv-c):

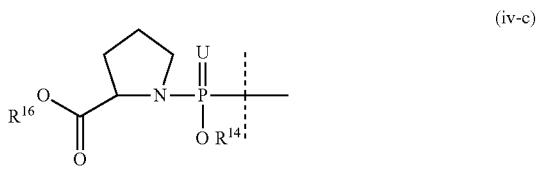

(iv-c)

Typically in this configuration, U is O, $R^{14}$ is optionally substituted phenyl and $R^6$ is $C_1$-$C_6$alkyl or $C_3$-$C_6$cycloalkyl.

Typically in compounds of formula (I) wherein $R^1$ is the group (iv), or any subgroup thereof, $R^2$ is H.

In a further embodiment of compounds of formula (I), $R^1$ is the group (v):

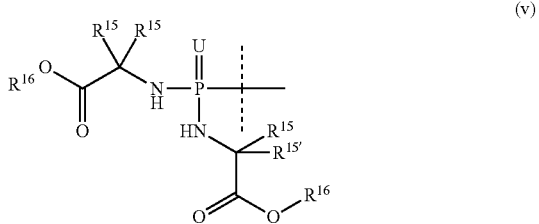

(v)

Typically in the group (v), U is O.

According to this embodiment, the two N-linked substituents to the P-atom are identical, i.e. both of the $R^{15}$ moieties are the same, both of the $R^{15'}$ moieties are the same, and both of $R^6$ moieties are the same.

In a typical configuration of the group (v) both $R^{15}$ are H or $C_1$-$C_6$alkyl (such as ethyl, n-propyl, isopropyl, n-butyl or isobutyl), both $R^{15'}$ are H, and both $R^{16}$ are $C_1$-$C_6$alkyl (such as methyl, ethyl or isopropyl) or $C_3$-$C_7$cycloalkyl (such as cyclopropyl, cyclobutyl or cyclopentyl).

In one configuration of group (v), $R^{16}$ is $C_1$-$C_3$alkyl, such as methyl, ethyl, propyl, isopropyl, preferably isopropyl.

In a further configuration of group (v), $R^{16}$ is $C_1$-$C_8$alkyl, such as 2-ethylbutyl, 2-pentyl, 2-butyl, isobutyl, tert-pentyl, preferably 2-ethylbutyl.

In a further configuration of group (v), $R^{16}$ is $C_3$-$C_7$cycloalkyl, such as cyclohexyl In a further embodiment of compounds of formula (I), $R^1$ is the group (vi):

(vi)

Typically in the group (vi), U is O.

In one configuration of the group (vi), $R^{13}$ is —($C_1$-$C_6$alkylene)-T-$R^{21}$, thus providing the structure (vi-a):

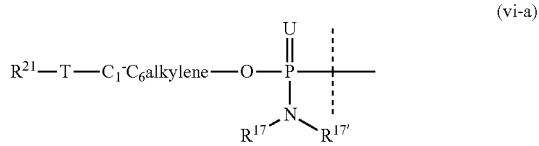

wherein the $C_1$-$C_6$alkylene moiety is linear or branched. Non-limiting examples of the $C_1$-$C_6$alkylene moiety in the group (vi-a) include methylene, ethylene, isopropylene and dimethylmethylene.

In one configuration of the subgroup vi-a, $R^{21}$ is 1-hydroxy-2-methylpropan-2-yl, i.e. a group of the formula:

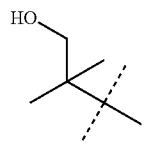

Typically in the group (vi-a), U is O.

In a typical subgroup of the group (vi-a), $C_1$-$C_6$alkylene is methylene which is optionally substituted with one or two $C_1$-$C_3$alkyl, and T is —OC(O)O—, thus providing compounds of formula I having of the partial structure (vi-b):

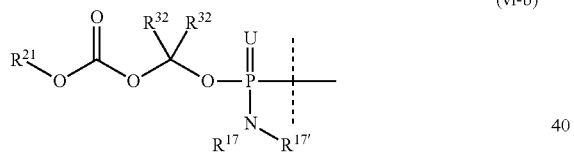

wherein $R^{32}$ and $R^{32'}$ are independently H or $C_1$-$C_3$alkyl. Typically, one of $R^{32}$ and $R^{32'}$ is H and the other one is H, methyl or isopropyl. Alternatively, $R^{32}$ and $R^{32'}$ are both methyl.

Typically in the group (vi-b), U is O.

Typical examples of $R^{21}$ include optionally substituted $C_1$-$C_6$alkyl, such as methyl, ethyl, propyl and isopropyl.

Typically, one of $R^{17}$ and $R^{17'}$ is H and the other one is phenyl or benzyl, preferably benzyl.

Typically in compounds of formula (I) wherein $R^1$ is the group (vi) or any subgroup thereof, $R^2$ is H.

In a further subgroup of the group (vi-a), U is O, $C_1$-$C_6$alkylene is ethylene and T is —C(O)S—, thus providing compounds of formula I having of the partial structure:

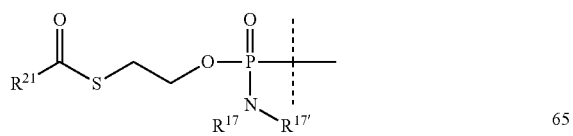

Typical examples of $R^{21}$ include optionally substituted $C_1$-$C_6$alkyl, especially branched $C_1$-$C_6$alkyl, and $C_1$-$C_6$hydroxyalkyl.

Typically, one of $R^{17}$ and $R^{17'}$ is H and the other one is phenyl or benzyl, preferably benzyl.

Typically in compounds of formula (I) wherein $R^1$ is the group (vi) or any subgroup thereof, $R^2$ is H.

In another aspect, the present invention provides compounds represented by formula V:

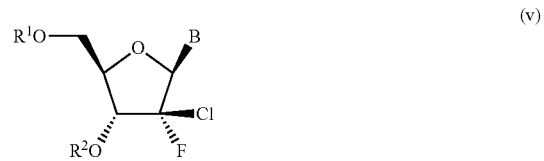

wherein:
B is a nucleobase selected from the groups (a) to (d):

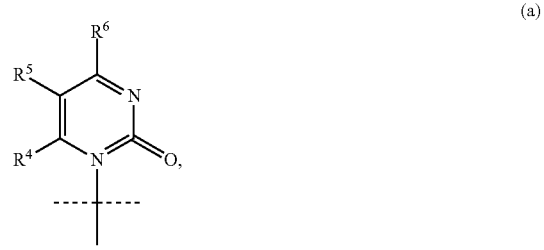

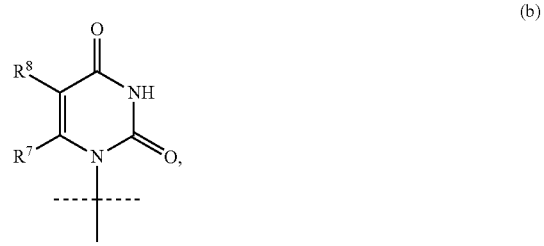

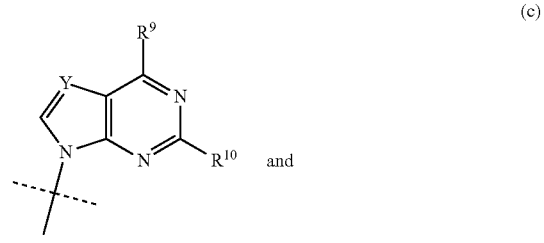

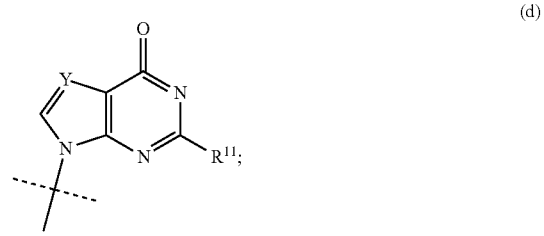

wherein Y is N or C($R^{19}$);

$R^1$ is the group (v):

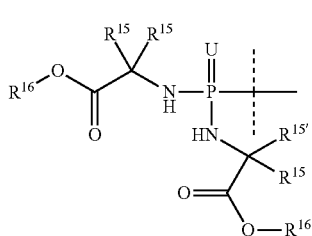

(v)

$R^4$, $R^5$, $R^7$ and $R^8$ are each independently H, $C_1$-$C_6$alkyl, $C_1$-$C_6$haloalkyl, $C_1$-$C_6$hydroxyalkyl, halo, —$OR^{18}$, —$SR^{18}$ or —$N(R^{18})_2$;

$R^6$, $R^9$, $R^{10}$, $R^{11}$ are each independently selected from H, $C_1$-$C_6$alkyl, $C_2$-$C_6$alkenyl, $C_2$-$C_6$alkynyl, $C_3$-$C_7$cycloalkyl, $C_1$-$C_6$haloalkyl, $C_1$-$C_6$hydroxyalkyl, halo, $OR^{18}$, $SR^{18}$, $N(R^{18})_2$, $NHC(O)OR^{18}$, $NHC(O)N(R^{18})_2$, CN, $NO_2$, $C(O)R^{18}$, $C(O)OR^{18}$, $C(O)N(R^{18})_2$ and $NHC(O)R^{18}$, wherein said $C_2$-$C_6$alkenyl group and said $C_2$-$C_6$alkynyl group can be optionally substituted with halo or $C_3$-$C_5$cycloalkyl;

$R^{15}$ and $R^{15'}$ are each independently selected from H, $C_1$-$C_6$alkyl, $C_3$-$C_7$cycloalkyl, $C_3$-$C_7$cycloalkyl$C_1$-$C_3$alkyl, phenyl and benzyl, or $R^{15}$ and $R^{15'}$ together with the carbon atom to which they are attached from a $C_3$-$C_7$cycloalkylene group, wherein each $C_1$-$C_6$alkyl is optionally substituted with a group selected from halo, $OR^{18}$ and $SR^{18}$, and each $C_3$-$C_7$cycloalkyl, $C_3$-$C_7$cycloalkylene, phenyl and benzyl is optionally substituted with one or two groups independently selected from $C_1$-$C_3$alkyl, halo and $OR^{18}$; or $R^{15'}$ is H and $R^{15}$ and $R^{24}$ together with the atoms to which they are attached, form a 5-membered ring;

$R^{16}$ is H, $C_1$-$C_{10}$alkyl, $C_2$-$C_{10}$alkenyl, $C_3$-$C_7$cycloalkyl, $C_3$-$C_7$cycloalkyl$C_1$-$C_3$alkyl, benzyl, phenyl or adamantyl, any of which is optionally substituted with 1, 2 or 3 groups, each independently selected from halo, $OR^{18}$ and $N(R^{18})_2$;

each $R^{18}$ is independently H, $C_1$-$C_6$alkyl, $C_1$-$C_6$haloalkyl or $C_3$-$C_7$cycloalkyl;

$R^{19}$ is H, $C_1$-$C_6$alkyl, $C_2$-$C_6$alkenyl, $C_2$-$C_6$alkynyl, $C_3$-$C_7$cycloalkyl, $C_1$-$C_6$haloalkyl, $C_1$-$C_6$hydroxyalkyl, halo, —$OR^{18}$ or $N(R^{18})_2$;

each $R^{20}$ is independently H, $C_1$-$C_6$alkyl, $C_1$-$C_6$haloalkyl, $C_3$-$C_7$cycloalkyl, $C_1$-$C_6$hydroxyalkyl or $C_3$-$C_7$cycloalkyl$C_1$-$C_3$alkyl;

each $R^{30}$ is independently selected from $C_1$-$C_6$alkyl and $C_1$-$C_6$alkoxy;

each $R^{31}$ is independently selected from H, $C_1$-$C_6$alkyl, $C_3$-$C_7$cycloalkyl and benzyl;

each $R^{32}$ and $R^{32'}$ is independently selected from H and $C_1$-$C_3$alkyl;

each $R^{33}$ is independently selected from H and $C_1$-$C_6$alkyl;

U is O;

or a pharmaceutically acceptable salt and/or solvate thereof.

In one embodiment of this aspect, the group B is (a')

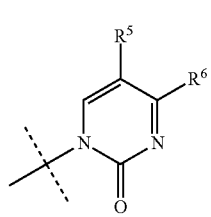

(a')

wherein
$R^5$ is H or F, and $R^6$ is $N(R^{18})_2$ or $NHCOC_1$-$C_6$alkyl. Typically $R^6$ is $NH_2$.

In one embodiment of this aspect, the group B is (b')

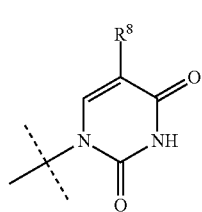

(b')

wherein $R^8$ is H or F. Typically, $R^8$ is H.

In one embodiment of this aspect, the group B is (c')

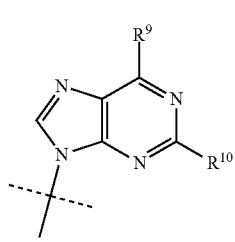

(c')

wherein $R^9$ is OH or $C_1$-$C_6$alkoxy, and $R^{10}$ is $NH_2$ or $NHCOC_1$-$C_6$alkyl.

Typically in this aspect, $R^2$ is H.

In another aspect, the present invention provides compounds represented by formula VI:

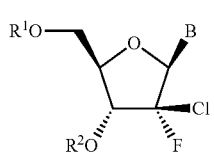

(VI)

wherein:

B is a nucleobase selected from the groups (a) to (d):

(a) 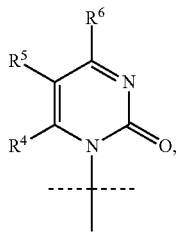

(b) 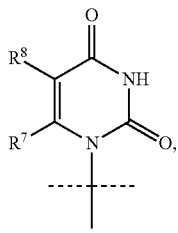

(c) 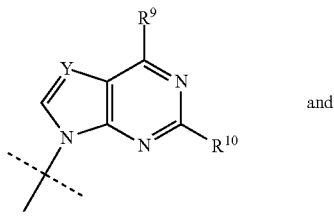

and (d) 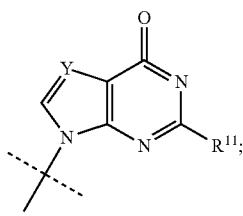

wherein Y is N or C($R^{19}$);

$R^1$ is the group (vi):

(vi) 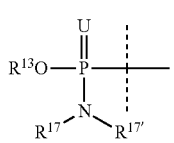

$R^2$ is H, C(=O)$R^{30}$, C(=O)CH$R^{31}$NH$_2$, C$R^{32}$$R^{32'}$OC(=O)CH$R^{33}$NH$_2$ or C$R^{32}$$R^{32'}$OC(=O)$R^{30}$;

$R^4$, $R^5$, $R^7$ and $R^8$ are each independently H, $C_1$-$C_6$alkyl, $C_1$-$C_6$haloalkyl, $C_1$-$C_6$hydroxyalkyl, halo, O$R^{18}$, S$R^{18}$ or N($R^{18}$)$_2$;

$R^6$, $R^9$, $R^{10}$, $R^{11}$ are each independently selected from H, $C_1$-$C_6$alkyl, $C_2$-$C_6$alkenyl, $C_2$-$C_6$alkynyl, $C_3$-$C_7$cycloalkyl, $C_1$-$C_6$haloalkyl, $C_1$-$C_6$hydroxyalkyl, halo, O$R^{18}$, S$R^{18}$, N($R^{18}$)$_2$, NHC(O)O$R^{18}$, NHC(O)N($R^{18}$)$_2$, CN, NO$_2$, C(O)$R^{18}$, C(O)O$R^{18}$, C(O)N($R^{18}$)$_2$ and NHC(O)$R^{18}$, wherein said $C_2$-$C_6$alkenyl group and said $C_2$-$C_6$alkynyl group can be optionally substituted with halo or $C_3$-$C_5$cycloalkyl;

$R^{13}$ is $C_1$-$C_6$alkylene-T-$R^{21}$;

each $R^{18}$ is independently H, $C_1$-$C_6$alkyl, $C_1$-$C_6$haloalkyl or $C_3$-$C_7$cycloalkyl;

$R^{19}$ is H, $C_1$-$C_6$alkyl, $C_2$-$C_6$alkenyl, $C_2$-$C_6$alkynyl, $C_3$-$C_7$cycloalkyl, $C_1$-$C_6$haloalkyl, $C_1$-$C_6$hydroxyalkyl, halo, O$R^{18}$ or N($R^{18}$)$_2$;

each $R^{20}$ is independently H, $C_1$-$C_6$alkyl, $C_1$-$C_6$haloalkyl, $C_3$-$C_7$cycloalkyl, $C_1$-$C_6$hydroxyalkyl or $C_3$-$C_7$cycloalkyl$C_1$-$C_3$alkyl;

each $R^{21}$ is independently H, $C_1$-$C_{24}$alkyl, $C_1$-$C_6$haloalkyl, $C_1$-$C_6$hydroxyalkyl, $C_2$-$C_6$alkenyl, $C_2$-$C_6$alkynyl, $C_3$-$C_7$cycloalkyl or $C_3$-$C_7$cycloalkenyl;

each $R^{30}$ is independently selected from $C_1$-$C_6$alkyl and $C_1$-$C_6$alkoxy;

each $R^{31}$ is independently selected from H, $C_1$-$C_6$alkyl, $C_3$-$C_7$cycloalkyl and benzyl;

each $R^{32}$ and $R^{32'}$ is independently selected from H and $C_1$-$C_3$alkyl;

each $R^{33}$ is independently selected from H and $C_1$-$C_6$alkyl;

U is O;

each T is independently S, O, SC(O), C(O)S, SC(S), C(S)S, OC(O), C(O)O and OC(O)O;

or a pharmaceutically acceptable salt and/or solvate thereof.

In one embodiment of this aspect, the group B is (a')

(a') 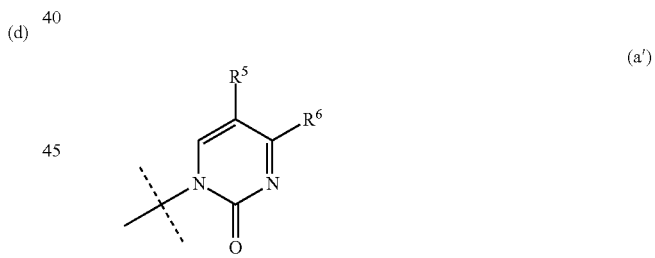

wherein $R^5$ is H or F, and $R^6$ is N($R^{18}$)$_2$ or NHCOC$_1$-$C_6$alkyl. Typically $R^6$ is NH$_2$.

In one embodiment of this aspect, the group B is (b')

(b') 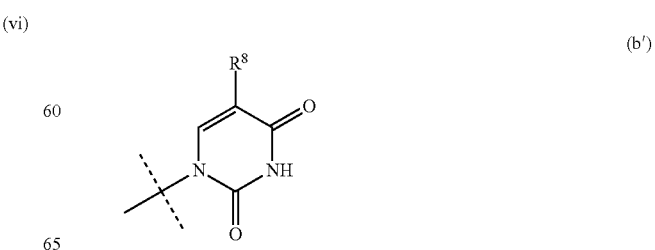

wherein $R^8$ is H or F. Typically, $R^8$ is H.

In one embodiment of this aspect, the group B is (c')

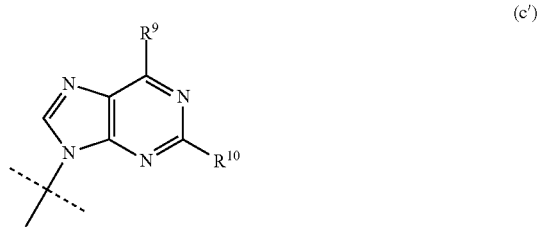

wherein $R^9$ is OH or $C_1$-$C_6$alkoxy, and $R^{10}$ is $NH_2$ or $NHCOC_1$-$C_6$alkyl.

Typically in this aspect, $R^2$ is H.

Consequently, there is provided a compound of formula I for use as a medicament, in particular for use in the treatment or prophylaxis of HCV infection, especially the treatment of HCV infection.

Further provided is the use of a compound of formula I in the manufacture of a medicament, in particular a medicament for the treatment or prophylaxis of HCV infection, especially a medicament for the treatment of HCV infection.

Additionally, there is provided a method for the treatment or prophylaxis of HCV infection comprising the administration of a compound of formula I, in particular a method for the treatment of HCV infection comprising the administration of a compound of formula I.

In a further aspect, the invention concerns the use of the compounds of the invention for inhibiting HCV.

Additionally, there is provided the use of the compounds of formula I for the treatment or prophylaxis of HCV infection, such as the treatment or prophylaxis of HCV infection in humans.

In a preferred aspect, the invention provides the use of compounds of formula I for the treatment of HCV infection, such as the treatment of HCV infection in humans.

Furthermore, the invention relates to a method for manufacturing compounds of formula I, to novel intermediates of use in the manufacture of compounds of formula I and to the manufacture of such intermediates.

In a further aspect, the invention provides pharmaceutical compositions comprising a compound of formula I in association with a pharmaceutically acceptable adjuvant, diluent, excipient or carrier. The pharmaceutical composition will typically contain an antivirally effective amount (e.g. for humans) of the compound of formula I, although sub-therapeutic amounts of the compound of formula I may nevertheless be of value when intended for use in combination with other agents or in multiple doses.

The skilled person will recognise that references to compounds of formula I will include any subgroup of the compounds of formula I described herein.

HCV genotypes in the context of treatment or prophylaxis in accordance with the invention include the major HCV genotypes, i.e. genotype 1a, 1b, 2a, 3a, 4a, 5a and 6a. The invention also provides a method for the treatment or prophylaxis of HCV infection. Typically, the invention provides a method for the treatment of HCV infection.

Representative HCV genotypes in the context of treatment or prophylaxis in accordance with the invention include genotype 1b (prevalent in Europe) and 1a (prevalent in North America). The invention also provides a method for the treatment or prophylaxis of HCV infection, in particular of the genotype 1a or 1b. Typically, the invention provides a method for the treatment of HCV infection, in particular of the genotype 1a or 1b.

Further representative genotypes in the context of treatment or prophylaxis in accordance with the invention include genotype 3a, such as wild type genotype 3a and mutant strains of the genotype 3a, for example the S282T and L159/320F mutants. Typically, the invention provides a method for the treatment of HCV infection, in particular of the genotype 3a, such as wild type genotype 3a and mutant strains of the genotype 3a, for example the S282T and L159/320F mutants.

The invention further relates to the treatment or prophylaxis of HCV infection caused by the genotypes 2a, 4a, 5a, 6a. The invention also provides a method for the treatment or prophylaxis of HCV infection, of the genotypes 2a, 4a, 5a, 6a.

The good activity of the compounds of the invention against genotype 3 is noteworthy given the poor performance of previous generations of nucleotides. Preferably the compositions of the invention have pan-genotypic coverage against each of the 6 genotypes, that is the $EC_{50}$ of the compound of the invention does not differ markedly between genotypes, thereby simplifying treatment.

The compounds of the invention have several chiral centers and may exist and be isolated in optically active and racemic forms. Some compounds may exhibit polymorphism. It is to be understood that any racemic, optically active, diastereomeric, polymorphic or stereoisomeric form or mixtures thereof, of a compound provided herein is within the scope of this invention. The absolute configuration of such compounds can be determined using methods known in the art such as, for example, X-ray diffraction or NMR and/or implication from starting materials of known stereochemistry and/or stereoselective synthesis methods. Pharmaceutical compositions in accordance with the invention will preferably comprise substantially stereoisomerically pure preparations of the indicated stereoisomer.

Most amino acids are chiral and can exist as separate enantiomers. They are designated L- or D-amino acids, wherein the L-enantiomer is the naturally occurring enantiomer. Accordingly, pure enantiomers of the amino acids are readily available and where an amino acid is used in the synthesis of a compound of the invention, the use of a chiral amino acid, will provide a chiral product.

Pure stereoisomeric forms of the compounds and intermediates as mentioned herein are defined as isomers substantially free of other enantiomeric or diastereomeric forms of the same basic molecular structure of said compounds or intermediates. In particular, the term "stereoisomerically pure" concerns compounds or intermediates having a stereoisomeric excess of at least 80% (i.e. minimum 90% of one isomer and maximum 10% of the other possible stereoisomers) up to a stereoisomeric excess of 100% (i.e. 100% of one isomer and none of the other), more in particular, compounds or intermediates having a stereoisomeric excess of 90% up to 100%, even more in particular having a stereoisomeric excess of 94% up to 100% and most in particular having a stereoisomeric excess of 97% up to 100%. The terms "enantiomerically pure" and "diastereomerically pure" should be understood in a similar way, but then having regard to the enantiomeric excess, and the diastereomeric excess, respectively, of the mixture in question.

Pure stereoisomeric forms of the compounds and intermediates of this invention may be obtained by using procedures well known in the art. For instance, enantiomers may be separated from each other by resolution of the racemic mixture, i.e. formation of a diastereomeric salt effected by reaction with an optically active acid or base followed by selective crystallization of the formed diastereomeric salt. Examples of such acids are tartaric acid, dibenzoyltartaric acid, ditoluoyltartaric acid and camphorsulfonic acid. Alternatively, enantiomers may be separated by chromatographic techniques using chiral stationary phases. Pure stereochemically isomeric forms may also be obtained by synthesis from stereochemically pure forms of the appropriate starting materials, provided that the reaction occurs stereospecifically, by chiral synthesis or by utilisation of a chiral auxiliary. If a specific stereoisomer is desired, the preparation of that compound is preferably performed using stereospecific methods. These methods will advantageously employ enantiomerically pure starting materials.

Diastereomeric racemates of the compounds of the invention can be separated by conventional methods. Appropriate physical separation methods that may advantageously be employed are, for example, selective crystallization and chromatography, e.g. column chromatography.

When a phosphorus atom is present in compounds of the invention comprising, the phosphorus atom may represent a chiral centre. The chirality at this centre is designated "R" or "S" according to the Cahn-Ingold-Prelog priority rules. When the chirality is not indicated, it is contemplated that both the R- and S-isomers are meant to be included, as well as a mixture of both.

In preferred embodiments of the invention compounds of formula I or any subgroup of formula I which are pure stereoisomers at the phosphorus atom are included. Preferred are compounds having the S-configuration at the phosphorus atom. These stereoisomers are designated Sp.

In other embodiments of the invention, compounds of formula I or any subgroup of formula I having the R-configuration at the phosphorus atom are included. These stereoisomers are designated $R_P$.

In other embodiments of the invention, diastereomeric mixtures are included, i.e. mixtures of compounds having the R- or S-configuration at the phosphorus atom.

The present invention also includes isotope-labelled compounds of formula I or any subgroup of formula I, wherein one or more of the atoms is replaced by an isotope of that atom, i.e. an atom having the same atomic number as, but an atomic mass different from, the one(s) typically found in nature. Examples of isotopes that may be incorporated into the compounds of formula I or any subgroup of formula I, include but are not limited to isotopes of hydrogen, such as $^2$H and $^3$H (also denoted D for deuterium and T for tritium, respectively), carbon, such as $^{11}$C, $^{13}$C and $^{14}$C, nitrogen, such as $^{13}$N and $^{15}$N, oxygen, such as $^{15}$O, $^{17}$O and $^{18}$O, phosphorus, such as $^{31}$P and $^{32}$P, sulfur, such as $^{35}$S, fluorine, such as $^{18}$F, chlorine, such as $^{36}$Cl, bromine such as $^{75}$Br, $^{76}$Br, $^{77}$Br and $^{82}$Br, and iodine, such as $^{123}$I, $^{124}$I, $^{125}$I and $^{131}$I. The choice of isotope included in an isotope-labelled compound will depend on the specific application of that compound. For example, for drug or substrate tissue distribution assays, compounds wherein a radioactive isotope such as $^3$H or $^{14}$C is incorporated will generally be most useful. For radio-imaging applications, for example positron emission tomography (PET) a positron emitting isotope such as $^{11}$C, $^{18}$F, $^{13}$N or $^{15}$O will be useful. The incorporation of a heavier isotope, such as deuterium, i.e. $^2$H, may provide greater metabolic stability to a compound of formula I or any subgroup of formula I, which may result in, for example, an increased in vivo half life of the compound or reduced dosage requirements.

Isotope-labelled compounds of formula I or any subgroup of formula I can be prepared by processes analogous to those described in the Schemes and/or Examples herein below by using the appropriate isotope-labelled reagent or starting material instead of the corresponding non-isotope-labelled reagent or starting material, or by conventional techniques known to those skilled in the art.

The pharmaceutically acceptable addition salts comprise the therapeutically active non-toxic acid and base addition salt forms of the compounds of formula I. Of interest are the free, i.e. non-salt forms of the compounds of formula I.

The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propionic, hydroxyacetic, lactic, pyruvic, oxalic (i.e. ethanedioic), malonic, succinic (i.e. butanedioic acid), maleic, fumaric, malic (i.e. hydroxylbutanedioic acid), tartaric, citric, methanesulfonic, ethanesulfonic, benzenesulfonic, p-toluenesulfonic, cyclamic, salicylic, p-aminosalicylic, pamoic and the like acids. Conversely said salt forms can be converted by treatment with an appropriate base into the free base form.

The compounds of formula I containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

Some of the compounds of formula I may also exist in their tautomeric form. For example, tautomeric forms of amide groups (—C(=O)—NH—) are iminoalcohols (—C(OH)=N—), which can become stabilized in rings with aromatic character. Such forms, although not explicitly indicated in the structural formulae represented herein, are intended to be included within the scope of the present invention.

The terms and expressions used herein throughout the abstract, specification and claims shall be interpreted as defined below unless otherwise indicated. The meaning of each term is independent at each occurrence. These definitions apply regardless of whether a term is used by itself or in combination with other terms, unless otherwise indicated. A term or expression used herein which is not explicitly defined, shall be interpreted as having its ordinary meaning used in the art. Chemical names, common names, and chemical structures may be used interchangeably to describe the same structure. If a chemical compound is referred to using both a chemical structure and a chemical name and an ambiguity exists between the structure and the name, the structure predominates.

"$C_m$-$C_n$alkyl" on its own or in composite expressions such as $C_m$-$C_n$haloalkyl, $C_m$-$C_n$alkylcarbonyl, $C_m$-$C_n$alkylamine, etc. represents a straight or branched aliphatic hydrocarbon radical having the number of carbon atoms designated, e.g. $C_1$-$C_4$alkyl means an alkyl radical having from 1 to 4 carbon atoms. $C_1$-$C_6$alkyl has a corresponding meaning, including also all straight and branched chain isomers of pentyl and hexyl. Preferred alkyl radicals for use in the present invention are $C_1$-$C_6$alkyl, including methyl, ethyl, n-propyl, isopropyl, n-butyl, isobutyl, sec-buty, tert-butyl, n-pentyl and n-hexyl, especially $C_1$-$C_4$alkyl such as methyl, ethyl, n-propyl, isopropyl, t-butyl, n-butyl and isobutyl. Methyl and isopropyl are typically preferred. An alkyl group may be unsubstituted or substituted by one or more substituents which may be the same or different, each substituent being independently selected from the group consisting of halo, alkenyl, alkynyl, aryl, cycloalkyl, cyano, hydroxy, —O-alkyl, —O-aryl, -alkylene-O-alkyl, alkylthio, —NH$_2$, —NH(alkyl), —N(alkyl)$_2$, —NH(cycloalkyl), —O—C(=O)-alkyl, —O—C(=O)-aryl, —O—C(=O)-cycloalkyl, —C(=O)OH and —C(=O)O-alkyl. It is generally preferred that the alkyl group is unsubstituted, unless otherwise indicated.

"$C_2$-$C_n$alkenyl" represents a straight or branched aliphatic hydrocarbon radical containing at least one carbon-carbon double bond and having the number of carbon atoms designated, e.g. $C_2$-$C_4$alkenyl means an alkenyl radical having from 2 to 4 carbon atoms; $C_2$-$C_6$alkenyl means an alkenyl radical having from 2 to 6 carbon atoms. Non-limiting alkenyl groups include ethenyl, propenyl, n-butenyl, 3-methylbut-2-enyl, n-pentenyl and hexenyl. An alkenyl group may be unsubstituted or substituted by one or more substituents which may be the same or different, each substituent being independently selected from the group consisting of halo, alkenyl, alkynyl, aryl, cycloalkyl, cyano, hydroxy, —O-alkyl, —O-aryl, -alkylene-O-alkyl, alkylthio, —NH$_2$, —NH(alkyl), —N(alkyl)$_2$, —NH(cycloalkyl), —O—C(=O)-alkyl, —O—C(=O)-aryl, —O—C(=O)-cycloalkyl, —C(=O)OH and —C(=O)O-alkyl. It is generally preferred that the alkenyl group is unsubstituted, unless otherwise indicated.

"$C_2$-$C_n$alkynyl" represents a straight or branched aliphatic hydrocarbon radical containing at least one carbon-carbon tripple bond and having the number of carbon atoms designated, e.g. $C_2$-$C_4$alkynyl means an alkynyl radical having from 2 to 4 carbon atoms; $C_2$-$C_6$alkynyl means an alkynyl radical having from 2 to 6 carbon atoms. Non-limiting alkenyl groups include ethynyl, propynyl, 2-butynyl and 3-methylbutynyl pentynyl and hexynyl. An alkynyl group may be unsubstituted or substituted by one or more substituents which may be the same or different, each substituent being independently selected from the group consisting of halo, alkenyl, alkynyl, aryl, cycloalkyl, cyano, hydroxy, —O-alkyl, —O-aryl, -alkylene-O-alkyl, alkylthio, —NH$_2$, —NH(alkyl), —N(alkyl)$_2$, —NH(cycloalkyl), —O—C(O)-alkyl, —O—C(O)-aryl, —O—C(O)-cycloalkyl, —C(O)OH and —C(O)O-alkyl. It is generally preferred that the alkynyl group is unsubstituted, unless otherwise indicated.

The term "$C_m$-$C_n$haloalkyl" as used herein represents $C_m$-$C_n$alkyl wherein at least one C atom is substituted with a halogen (e.g. the $C_m$-$C_n$haloalkyl group may contain one to three halogen atoms), preferably chloro or fluoro. Typical haloalkyl groups are $C_1$-$C_2$haloalkyl, in which halo suitably represents fluoro. Exemplary haloalkyl groups include fluoromethyl, difluromethyl and trifluoromethyl.

The term "$C_m$-$C_n$hydroxyalkyl" as used herein represents $C_m$-$C_n$alkyl wherein at least one C atom is substituted with one hydroxy group. Typical $C_m$-$C_n$hydroxyalkyl groups are $C_m$-$C_n$alkyl wherein one C atom is substituted with one hydroxy group. Exemplary hydroxyalkyl groups include hydroxymethyl and hydroxyethyl.

The term "$C_m$-$C_n$aminoalkyl" as used herein represents $C_m$-$C_n$alkyl wherein at least one C atom is substituted with one amino group. Typical $C_m$-$C_n$aminoalkyl groups are $C_m$-$C_n$alkyl wherein one C atom is substituted with one amino group. Exemplary aminoalkyl groups include aminomethyl and aminoethyl.

The term "$C_m$-$C_n$alkylene" as used herein represents a straight or branched bivalent alkyl radical having the number of carbon atoms indicated. Preferred $C_m$-$C_n$alkylene radicals for use in the present invention are $C_1$-$C_3$alkylene. Non-limiting examples of alkylene groups include —CH$_2$—, —CH$_2$CH$_2$—, —CH$_2$CH$_2$CH$_2$—, —CH(CH$_3$)CH$_2$CH$_2$—, —CH(CH$_3$)— and —CH(CH(CH$_3$)$_2$)—.

The term "Me" means methyl, and "MeO" means methoxy.

The term "$C_m$-$C_n$alkylcarbonyl" represents a radical of the formula $C_m$-$C_n$alkyl-C(=O)— wherein the $C_m$-$C_n$alkyl moiety is as defined above. Typically, "$C_m$-$C_n$alkylcarbonyl" is $C_1$-$C_6$alkyl-C(=O)—.

"$C_m$-$C_n$alkoxy" represents a radical $C_m$-$C_n$alkyl-O— wherein $C_m$-$C_n$alkyl is as defined above. Of particular interest is $C_1$-$C_4$alkoxy which includes methoxy, ethoxy, n-propoxy, isopropoxy, t-butoxy, n-butoxy and isobutoxy. Methoxy and isopropoxy are typically preferred. $C_1$-$C_6$alkoxy has a corresponding meaning, expanded to include all straight and branched chain isomers of pentoxy and hexoxy.

The term "$C_m$-$C_n$alkoxycarbonyl" represents a radical of the formula $C_m$-$C_n$alkoxy-C(=O)— wherein the $C_m$-$C_n$alkoxy moiety is as defined above. Typically, "$C_m$-$C_n$alkoxycarbonyl" is $C_1$-$C_6$alkoxy-C(=O)—.

The term "amino" represents the radical —NH$_2$.

The term "halo" represents a halogen radical such as fluoro, chloro, bromo or iodo. Typically, halo groups are fluoro or chloro.

The term "aryl" means a phenyl, biphenyl or naphthyl group.

The term "heterocycloalkyl" represents a stable saturated monocyclic 3-7 membered ring containing 1-3 heteroatoms independently selected from O, S and N. In one embodiment the stable saturated monocyclic 3-7 membered ring contains 1 heteroatom selected from O, S and N. In a second embodiment the stable saturated monocyclic 3-7 membered ring contains 2 heteroatoms independently selected from O, S and N. In a third embodiment the stable saturated monocyclic 3-7 membered ring contains 3 heteroatoms independently selected from O, S and N. The stable saturated monocyclic 3-7 membered ring containing 1-3 heteroatoms independently selected from O, S and N may typically be a 5-7 membered ring, such as a 5 or 6 membered ring. A heterocycloalkyl group may be unsubstituted or substituted by one or more substituents which may be the same or different, each substituent being independently selected from the group consisting of halo, alkenyl, alkynyl, aryl, cycloalkyl, cyano, hydroxy, —O-alkyl, —O-aryl, -alkylene-O-alkyl, alkylthio, —NH$_2$, —NH(alkyl), —N(alkyl)$_2$, —NH(cycloalkyl), —O—C(O)-alkyl, —O—C(O)-aryl, —O—C(O)-cycloalkyl, —C(O)OH and —C(O)O-alkyl. It is generally preferred that the heterocycloalkyl group is unsubstituted, unless otherwise indicated.

The term "heteroaryl" represents a stable mono or bicyclic aromatic ring system containing 1-4 heteroatoms independently selected from O, S and N, each ring having 5 or 6 ring atoms. In one embodiment of the invention the stable mono or bicyclic aromatic ring system contains one heteroatom selected from O, S and N, each ring having 5 or 6 ring atoms. In a second embodiment of the invention the stable mono or bicyclic aromatic ring system contains two heteroatoms independently selected from O, S and N, each ring having 5 or 6 ring atoms. In a third embodiment the stable mono or bicyclic aromatic ring system contains three heteroatoms independently selected from O, S and N, each ring having 5 or 6 ring atoms. In a fourth embodiment the stable mono or bicyclic aromatic ring system contains four heteroatoms independently selected from O, S and N, each ring having 5 or 6 ring atoms.

One embodiment of heteroaryl comprises flavone.

The term "$C_3$-$C_n$cycloalkyl" represents a cyclic monovalent alkyl radical having the number of carbon atoms indicated, e.g. $C_3$-$C_7$cycloalkyl means a cyclic monovalent alkyl radical having from 3 to 7 carbon atoms. Preferred cycloalkyl radicals for use in the present invention are $C_3$-$C_4$alkyl i.e. cyclopropyl and cyclobutyl. A cycloalkyl group may be unsubstituted or substituted by one or more substituents which may be the same or different, each substituent being independently selected from the group consisting of halo, alkenyl, alkynyl, aryl, cycloalkyl, cyano, hydroxy, —O-alkyl, —O-aryl, -alkylene-O-alkyl, alkylthio, —NH$_2$, —NH(alkyl), —N(alkyl)$_2$, —NH(cycloalkyl), —O—C(O)-alkyl, —O—C(O)-aryl, —O—C(O)-cycloalkyl, —C(O)OH and —C(O)O-alkyl. It is generally preferred that the cycloalkyl group is unsubstituted, unless otherwise indicated.

The term "aminoC$_m$-C$_n$alkyl" represents a $C_m$-$C_n$alkyl radical as defined above which is substituted with an amino group, i.e. one hydrogen atom of the alkyl moiety is replaced by an NH$_2$-group. Typically, "aminoC$_m$-C$_n$alkyl" is aminoC$_1$-C$_6$alkyl.

The term "aminoC$_m$-C$_n$alkylcarbonyl" represents a $C_m$-$C_n$alkylcarbonyl radical as defined above, wherein one hydrogen atom of the alkyl moiety is replaced by an NH$_2$-group. Typically, "aminoC$_m$-C$_n$alkylcarbonyl" is aminoC$_1$-C$_6$alkylcarbonyl. Examples of aminoC$_m$-C$_n$alkylcarbonyl include but are not limited to glycyl: C(=O)CH$_2$NH$_2$, alanyl: C(=O)CH(NH$_2$)CH$_3$, valinyl: C=OCH(NH$_2$)CH(CH$_3$)$_2$, leucinyl: C(=O)CH(NH$_2$)(CH$_2$)$_3$CH$_3$, isoleucinyl: C(=O)CH(NH$_2$)CH(CH$_3$)(CH$_2$CH$_3$) and norleucinyl: C(=O)CH(NH$_2$)(CH$_2$)$_3$CH$_3$ and the like. This definition is not limited to naturally occurring amino acids.

Related terms, are to be interpreted accordingly in line with the definitions provided above and the common usage in the technical field.

As used herein, the term "(=O)" forms a carbonyl moiety when attached to a carbon atom. It should be noted that an atom can only carry an oxo group when the valency of that atom so permits.

The term "monophosphate, diphosphate and triphosphate ester" refers to groups:

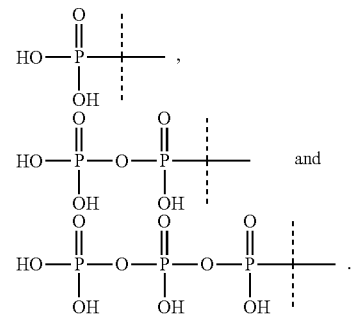

The term "thio-monophosphate, thio-diphosphate and thio-triphosphate ester" refers to groups:

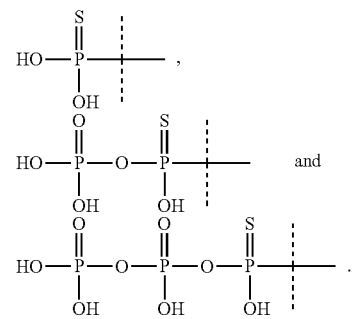

As used herein, the radical positions on any molecular moiety used in the definitions may be anywhere on such a moiety as long as it is chemically stable. When any variable present occurs more than once in any moiety, each definition is independent.

Whenever used herein, the term "compounds of formula I", or "the compounds of the invention" or similar terms, it is meant to include the compounds of formula I and subgroups of compounds of formula I, including the possible stereochemically isomeric forms, and their pharmaceutically acceptable salts and solvates.

The term "solvates" covers any pharmaceutically acceptable solvates that the compounds of formula I as well as the salts thereof, are able to form. Such solvates are for example hydrates, alcoholates, e.g. ethanolates, propanolates, and the like, especially hydrates.

In general, the names of compounds used in this application are generated using ChemDraw Ultra 12.0. In addition, if the stereochemistry of a structure or a portion of a structure is not indicated with for example bold or dashed lines, the structure or portion of that structure is to be interpreted as encompassing all stereoisomers of it.

General Synthetic Methods

Compounds of the present invention may be prepared by a variety of methods e.g. as depicted in the illustrative synthetic schemes shown and described below. The starting materials and reagents used are available from commercial suppliers or can be prepared according to literature procedures set forth in references using methods well known to those skilled in the art.

Scheme 1 illustrates a route to compounds of formula I wherein $R^1$ and $R^2$ are H, and the base B is uracil or derivatised uracil, i.e. B is a group of formula (b).

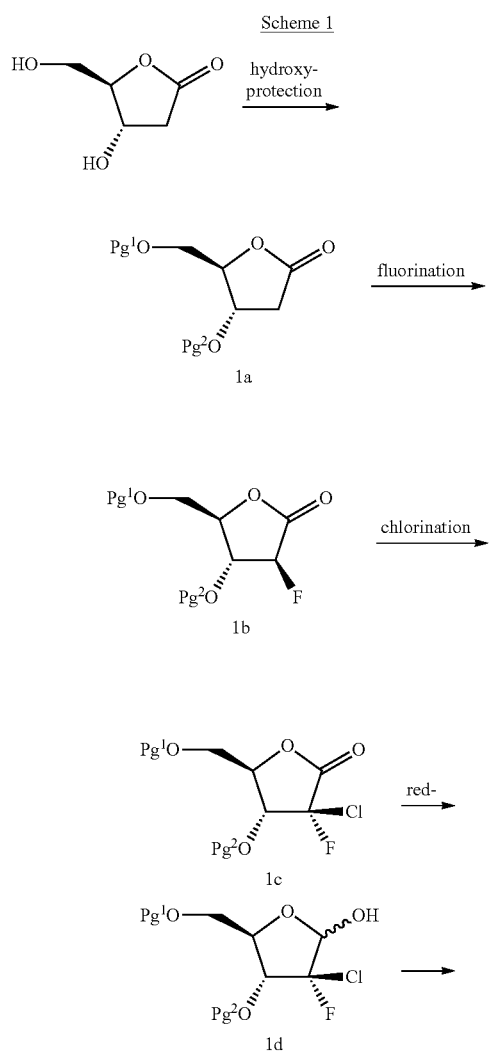

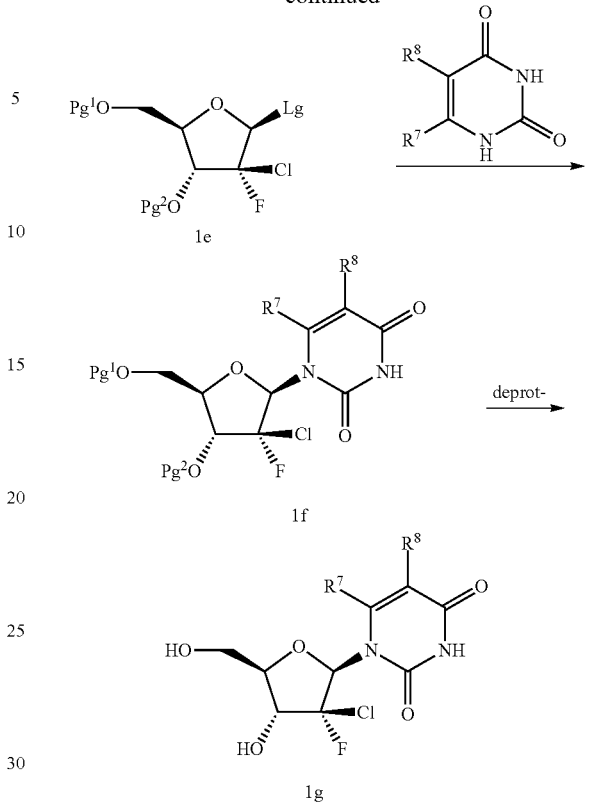

$Pg^1$ anad $Pg^2$ are, the same or different, hydroxy protecting groups
Lg is a leaving group, e.g. methylsulfonate, a halide or a phosphate ester Protection of the hydroxy groups of (4S,5R)-4-hydroxy-5-(hydroxymethyl)dihydrofuran-2(3H)-one using for instance triisopropylsilyl (TIPS) groups effected by treatment with TIPS-chloride in the presence of a base like imidazole or similar, or any other suitable protecting groups such as acyl groups like acetyl, benzoyl or p-chlorobenzoyl groups or trityl groups may be used. Alternatively, an orthogonal protecting group strategy may be employed in order to enable later selective deprotection of one of the hydroxy groups without touching the other. Typically then, the 5'-hydroxy group is protected with a trityl, methoxytrityl or a silyl group, followed by protection of the 3'-hydroxy group using e.g. an acyl group. The thus protected derivative is then subjected to electrophilic α-fluorination by treatment with N-fluorobenzenesulfonimide (NFSI) in the presence of a base like bis(trimethylsilyl) amide provides fluoro lactone (1b). The α-chloro substituent is then conveniently introduced by reaction with N-chlorosuccinimide in the presence of a base like lithium bis(trimethylsilyl) amide or similar. Subsequent reduction of the keto function using any suitable reducing agent such as DIBAL or the like, followed by conversion of the afforded hydroxy group to a leaving group, for instance a derivative of sulfonic acid, a halide or a phosphate ester provides the glycosyl donor (1e). A derivative of sulfonic acid such as a methylsulfone, is typically prepared by treatment with mesyl chloride or equivalent in the presence of a base such as $Et_3N$; the glycosyl bromide is typically prepared via the anomeric acetate by acetylation of the hydroxy group using acetic anhydride or similar followed by treatment with hydrogen bromide in acetic acid. The nucleoside (1f) is then formed by condensation with the desired base or a protected derivative thereof using standard conditions well known in the field of nucleoside chemistry such as in the presence of hexamethyldisilazane (HDMS) and a Lewis acid such as TMS triflate, or tin tetrachloride or similar. In the case the glycosyl bromide is used as glycosyl donor, a promotor for the glycosylation reaction like tintetrachloride or a silver salt such as silver triflate or similar is suitably used. Removal of the hydroxy protecting groups and, if present, protecting groups on the base, using the appropriate methods according to the groups by standard methods well known in the art, then provides the nucleoside (1g). If desired, the afforded nucleoside (1g) can then be transformed into a 5'-mono, di- or tri-phosphate, a 5'-thiomono-, thio-di- or thio-triphosphate, or to a prodrug using any of the methods described herein below or according to literature procedures.

Compounds of the invention carrying a cyclic phosphate ester prodrug moiety linking the 3'-position and 5'-positions together, i.e. $R^1$ and $R^2$ together with the oxygen atoms to which they are attached form a cyclic phosphate ester, can be prepared for example according to the methods described in WO2010/075554. A route to such compounds wherein $R^3$ is $OR^{3'}$ and $R^{3'}$ is H, $C_1$-$C_6$alkyl, $C_3$-$C_7$cycloalkyl, $C_3$-$C_7$cycloalkyl$C_1$-$C_3$alkyl or benzyl, and a phosphorus (III)-reagent is used for the introduction of the phosphorus moiety, is depicted in Scheme 2A.

butylhydroperoxide, hydrogen peroxide or the like. Alternatively, TEMPO-oxidation or an iodine-THF-pyridine-water based oxidation, or any other suitable oxidation method may be used.

Similarly, the corresponding cyclic thiophosphate prodrug, i.e. U is S in compounds of the invention carrying a 3',5'-cyclic prodrug moiety (2d), will be obtained by sulfurization of the phosphite derivative (2b). suitable sulfurization agents include, but are not limited to, elemental sulfur, Lawesson's reagent, cyclooctasulfur, bis(triethoxysilyl)propyl-tetrasulfide (TEST).

The cyclic phosphate ester (2c), may alternatively be prepared directly in one step by reaction of the diol with a P(V)-reagent, such as alkyl phosphorodichloridate, thus avoiding the separate oxidation step.

Phosphorus (III) and phosphorus (V) reagents to be used in the formation of the cyclic phosphite and phosphate esters respectively can be prepared as described in WO2010/075554. In short, reaction of commercially available chloro-N,N,N',N'-tetraisopropylphosphoramidite with the desired alcohol, $R^{3'}$—OH in the presence of a tertiary amine such as $Et_3N$ provides the phosphorus (III) reagent, whereas reaction of phosphoryl trichloride ($POCl_3$) with the desired alcohol $R^{3'}$—OH in the presence of $Et_3N$ or similar, provides the phosphorus (V) reagent.

Cyclic phosphate ester prodrugs of the invention wherein U is O, $R^3$ is $NHC(R^{15})(R^{15'})C(=O)R^{16}$, may be prepared as depicted in Scheme 2B.

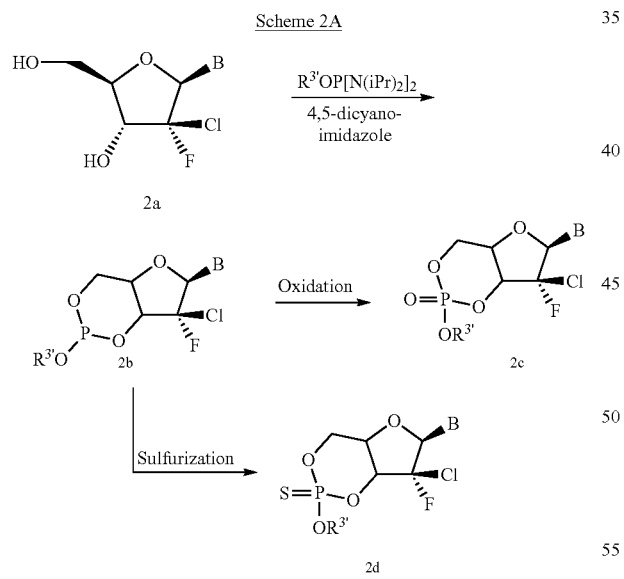

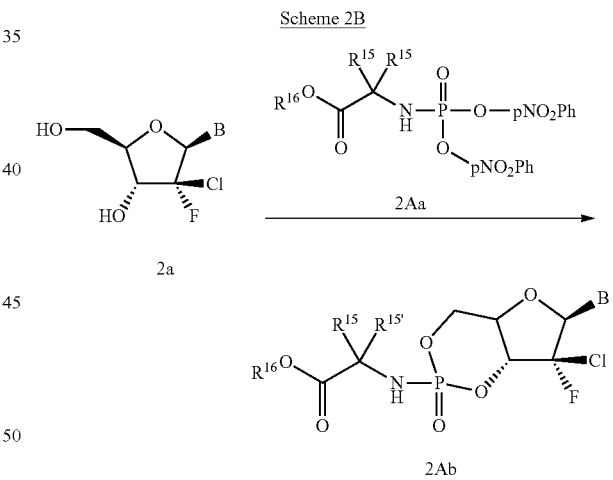

Reaction of the diol (2a), prepared as described above with a phosphorus(III)-reagent, such as alkyl-N,N,N',N'-tetraisopropylphosphoramidite, carrying the desired group $R^{3'}$ in the presence of an activator such as tetrazole or dicyanoimidazole or the like, provides the cyclic phosphite ester (2b). Subsequent oxidation of the phosphite ester to the phosphate ester (2c) is then carried out using any convenient oxidation method known in the art, e.g. oxidation using a peroxide reagent such as m-chloroperbenzoic acid, tert- Formation of the cyclic phosphate ester (2Ab) is effected for instance by reaction of the of the diol (2a) with a phosphorylating agent carrying the desired amino acid ester and two leaving groups (2Aa), for instance two p-nitrophenol groups, in the presence of a base such as DBU or equivalent using a solvent such as MeCN or the like.

In a similar manner, the corresponding cyclic thiophosphate prodrug, i.e. U is S in compounds of the invention carrying a 3',5'-cyclic prodrug moiety, will be obtained by using the corresponding thio phosphoramidate as phosphorylating agent.

For the preparation of compounds of the invention wherein R2 is H and $R^1$ is a phosphoramidate, i.e. a prodrug moiety of formula (iv), advantage can be taken of the higher reactivity of the primary 5'-hydroxy group compared to the secondary 3'-hydroxy group, and the phosphoramidate can be introduced directly on the 3',5-diol without need of any special protecting group strategy. This method is illustrated in Scheme 3.

Condensation of nucleoside derivative (3a), prepared as described above, with a desired phosphoramidochloridate in an inert solvent such as an ether, e.g. diethyl ether or THF, or a halogenated hydrocarbon, e.g. dichloromethane, in the presence of a base such as a N-methylimidazole (NMI) or the like, provides the phosphoramidate derivative (3b).

Similarly, compounds of the invention wherein $R^2$ is H and $R^1$ is a thiophosphoramidate, i.e. a prodrug moiety of formula (iv) wherein U is S, are obtained by reacting the sugar (3a) with a thiophosphoramidochloridate.

The phosphoramidochloridate used in the above scheme can be prepared in a two-step reaction starting from phosphorus oxychloride ($POCl_3$). Scheme 4 illustrates the preparation of phosphoramidochloridates useful for the preparation of compounds of formula I wherein $R^1$ is a group of formula (iv) wherein U is O and $R^{24}$ is H, and to phosphoramidochloridates useful for the preparation of compounds of formula I wherein $R^1$ is a group of formula (iv-c) wherein U is O, and $R^{24}$ and $R^{15'}$ together with the atoms to which they are attached form a pyrrolidine ring.

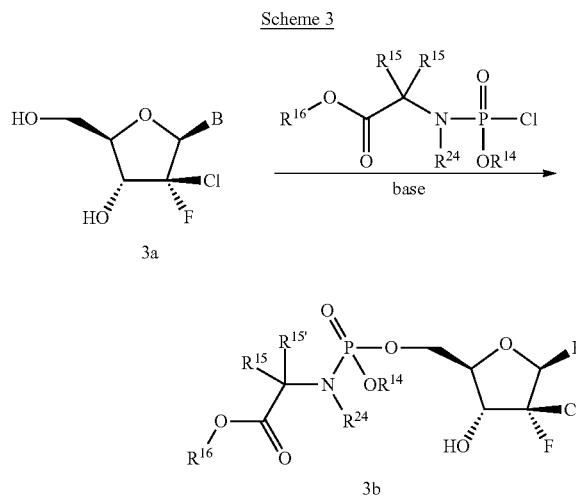

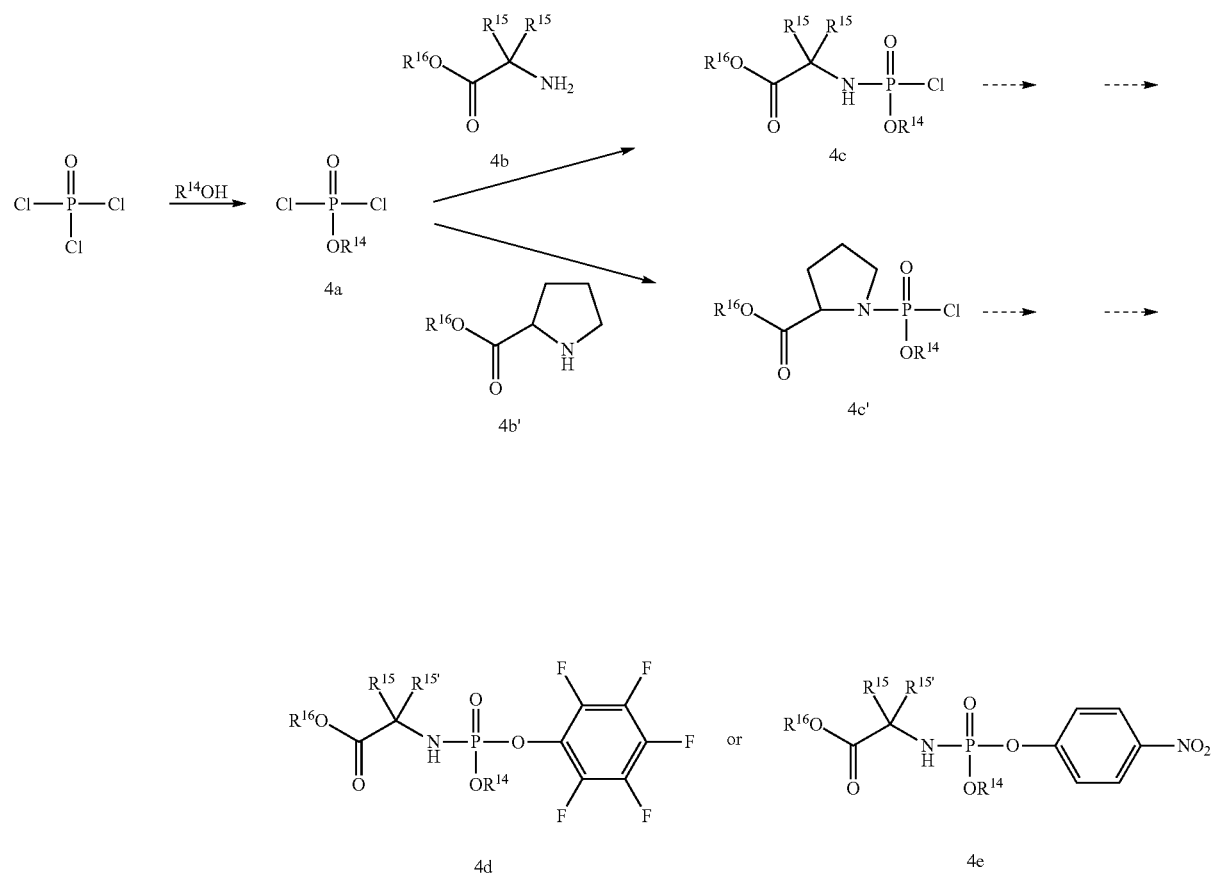

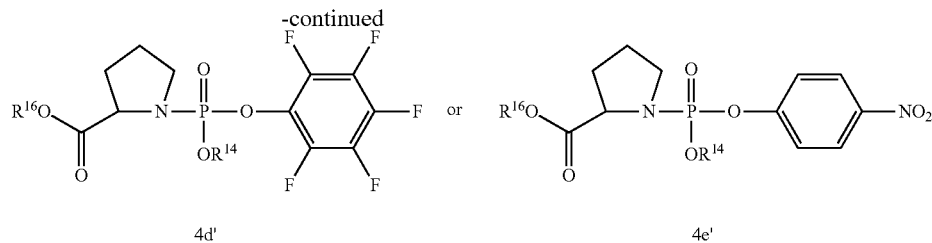

4d'    4e'

Condensation of POCl₃ with a desired alcohol $R^{14}OH$ in an inert solvent like Et₂O provides alkoxy or aryloxy phosphorodichloridate (4a). Subsequent reaction with an amino acid derivative (4b) or (4b') provides the chlorophosphoramidate (4c) or (4c') respectively. If desired, the obtained chlorophosphoramidates (4c) and (4c') may be converted to the corresponding phosphorylating agent having an activated phenol as leaving group, for instance pentaflurorophenol or p-NO₂-phenol as generally illustrated by fig 4d and 4e respectively. This conversion is conveniently performed by reaction of the chloro derivative (4c) or (4c') with the desired activated phenol in the presence of a base like triethylamine or similar.

Thiophosphoramidochloridates i.e. phosphorylating reagents useful for the preparation of compounds of formula (I) wherein $R^1$ is a group of formula (iv) and U is S, may be prepared using a similar strategy as generally outlined above, as illustrated in Scheme 5.

Scheme 5

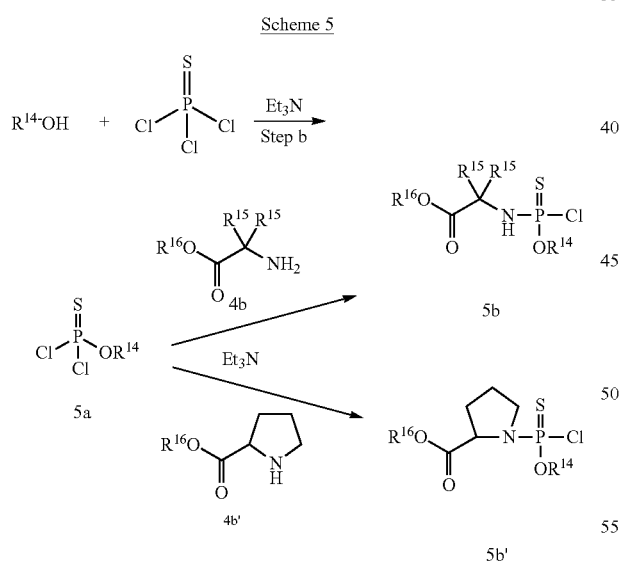

Reaction of thiophosphoryl chloride with a desired alcohol $R^{14}OH$ in the presence of a base such as Et₃N or the like, provides alkoxy or aryloxy thiophosphorodichloridate (5a). Subsequent reaction with an amino acid derivative (4b) or (4b') provides the thiophosphoramidochloridates (5b) or (5b') respectively.

A route to a phosphorylating agent useful for the preparation of compounds of formula (I) wherein $R^1$ is the group (v) and U is O is depicted in Scheme 6.

Scheme 6

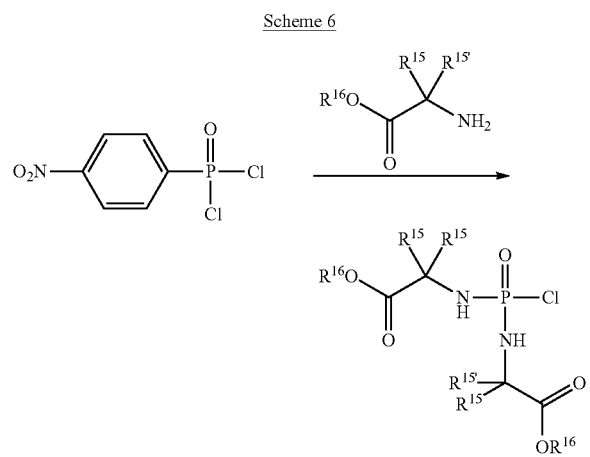

Reaction of a phosphorylating agent like 4-nitrophenyl dichlorophosphate, phosphoryl trichloride or similar with a suitable amine in the presence of Et₃N or the like in a solvent like DCM, provides the desired chlorophosphorodiamidate.

Compounds of formula (I) wherein $R^1$ is a prodrug moiety of group (i), $R^{12}$ and $R^{13}$ are both $R^{21}(=O)S$—(C₁-C₆alkylene)- and U is O, can be prepared according to literature procedures. For example, the method described in Bioorg. & Med. Chem. Let., Vol. 3, No 12, 1993, p. 2521-2526, as generally illustrated in Scheme 7A.

Scheme 7A

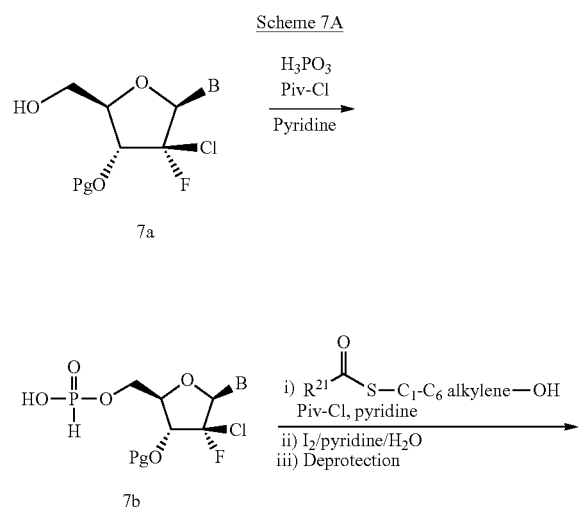

-continued

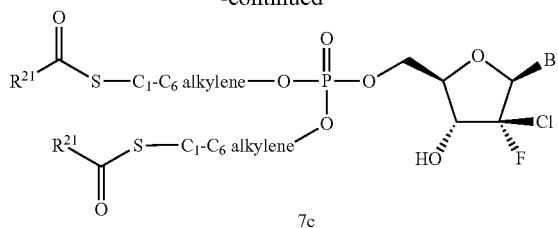

7c

Conversion of the 5'-hydroxy compound (7a) to the corresponding hydrogenphosphonate (7b) effected by treatment with phosphonic acid in pyridine in the presence of an activator such as pivaloyl chloride, followed by reaction with S-(2-hydroxyalkyl)alkanethioate and pivaloyl chloride in pyridine and subsequent oxidation using for instance conditions like iodine in pyridine/water provides the phosphotriester. Removal finally of protecting groups using standard methods, provides the nucleotide prodrug (7c).

Alternatively, nucleotide prodrug (7c) may be prepared by phosphorylation of the nucleoside (7a) with a phosphorylating agent already carrying the appropriate substituents.This method is described in WO2013/096679 and illustrated in Scheme 7B.

Scheme 7B

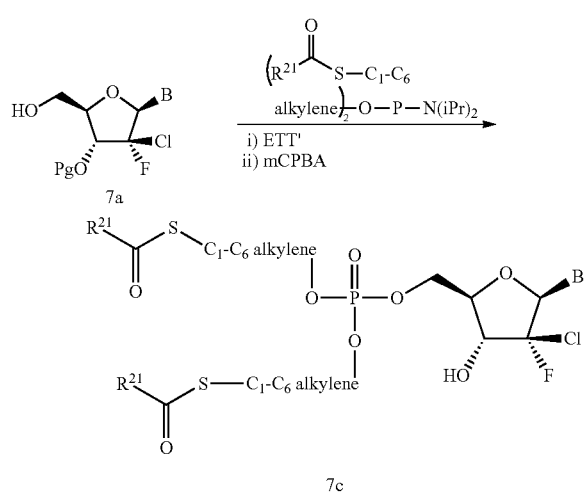

Reaction of nucleoside (7a) with the phosphorylating agent, in the presence of 5-ethylthiotetrazole (ETT), followed by oxidation using for instance mCPBA, provides the desired prodrug (7c). The phosphorylating agent is suitably prepared according to literature procedures as generally sketched out in Scheme 8.

Scheme 8

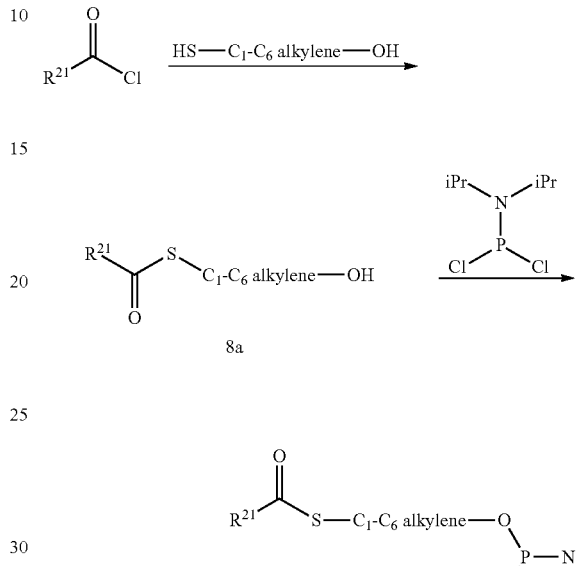

Reaction of the desired acylchloride $R^{21}C(=O)Cl$ with mercaptoalcanol of the desired configuration in the presence of a tertiary amine such as triethylamine or equivalent, followed by treatment of the afforded acyl thioalkanol derivative (8a) with 1,1-dichloro-N,N-diisopropylphosphinamine provides the phosphorylating agent (8b).

Compounds of formula I, wherein $R^1$ is a prodrug moiety of group (i) and $R^{12}$ and $R^{13}$ are of the formula $R^{21}C(=O)$ O—$C_1$-$C_6$alkylene- or $R^{21}OC(=O)O$—$C_1$-$C_6$alkylene- can be prepared according to the methods described in e.g. WO2013/096679 and references cited therein. The method is briefly illustrated in Scheme 9A.

Scheme 9A

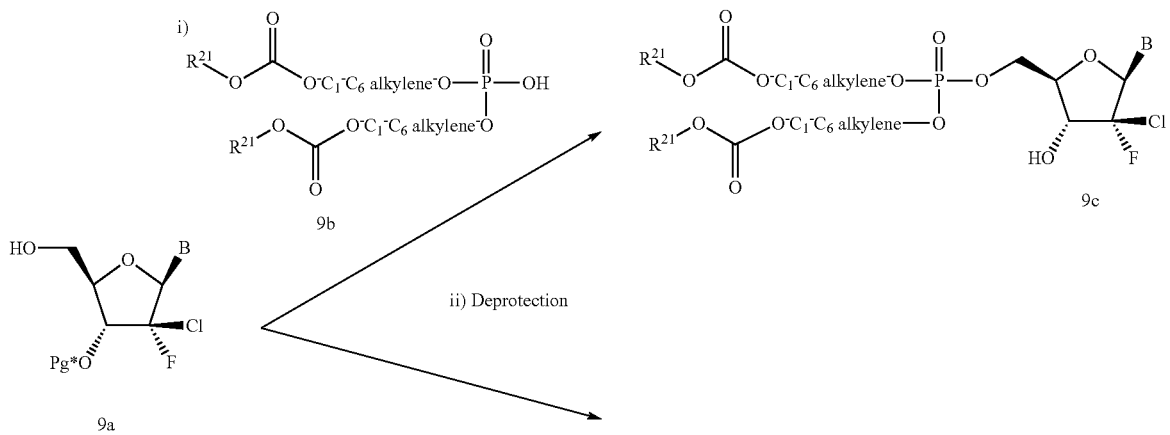

i) 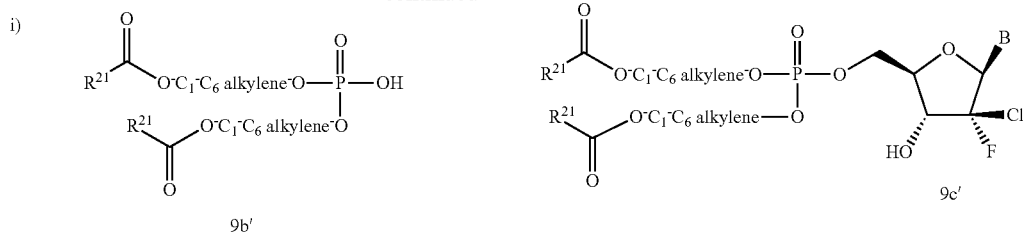

Pg* is H or a hydroxy protecting group

Coupling of the optionally protected nucleoside 9a with a suitable bisphosphate 9b or 9b', preferably in the form of the ammonium salt such as the triethylammonium salt or the like, in the presence of DIEA or the like, using suitable coupling conditions like BOP—Cl and 3-nitro-1,2,4-triazole in a solvent like THF, provides the prodrugs 9c and 9c' respectively.

In an alternative approach to compounds of formula I wherein $R^1$ is a prodrug moiety of group (i) and $R^{12}$ and $R^{13}$ are of the formula $R^{21}C(=O)O—C_1-C_6$alkylene- or $R^{21}OC(=O)O—C_1-C_6$alkylene-, the nucleoside 9a is reacted with phosphorus oxychloride in a first step and subsequently further reacted with the desired with an already substituted phosphorylating agent, as illustrated in Scheme 9B Scheme 9B ii) 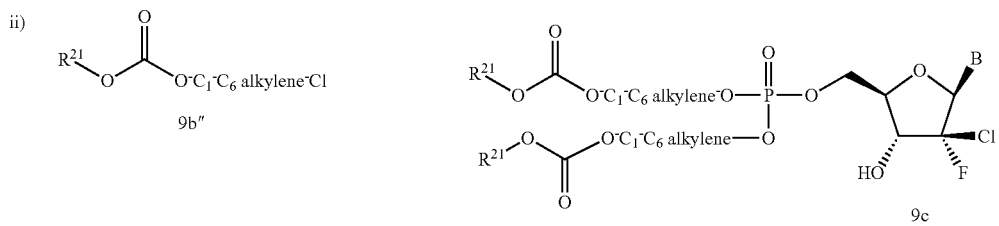

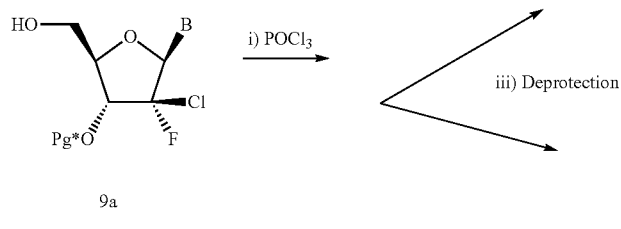

ii) 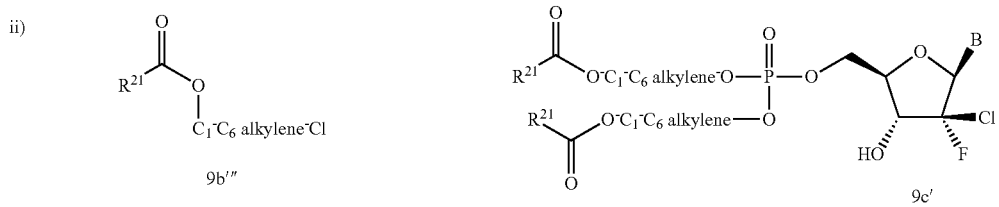

Pg* is H or a hydroxy protecting group

The phosphates 9c and 9c' are obtained by reaction of nucleoside 9a with phosphorus oxychloride in using a solvent such as triethyl phosphate, followed by reaction at elevated temperature with the desired chloroalkyl carbonate (9b'') or ester (9b''') in the presence of DIEA.

Compounds of formula I wherein $R^1$ is a prodrug moiety of group (i) wherein U is O, $R^{12}$ is H and $R^{13}$ is of the formula $R^{21}$—O—$C_1$-$C_6$alkylene- and $R^{21}$ is $C_1$-$C_{24}$alkyl can be prepared in line with methods described in e.g. J. Med. Chem., 2006, 49, 6, p. 2010-2013 and WO2009/085267 and references cited therein. A general method is illustrated in Scheme 10A.

Scheme 10A

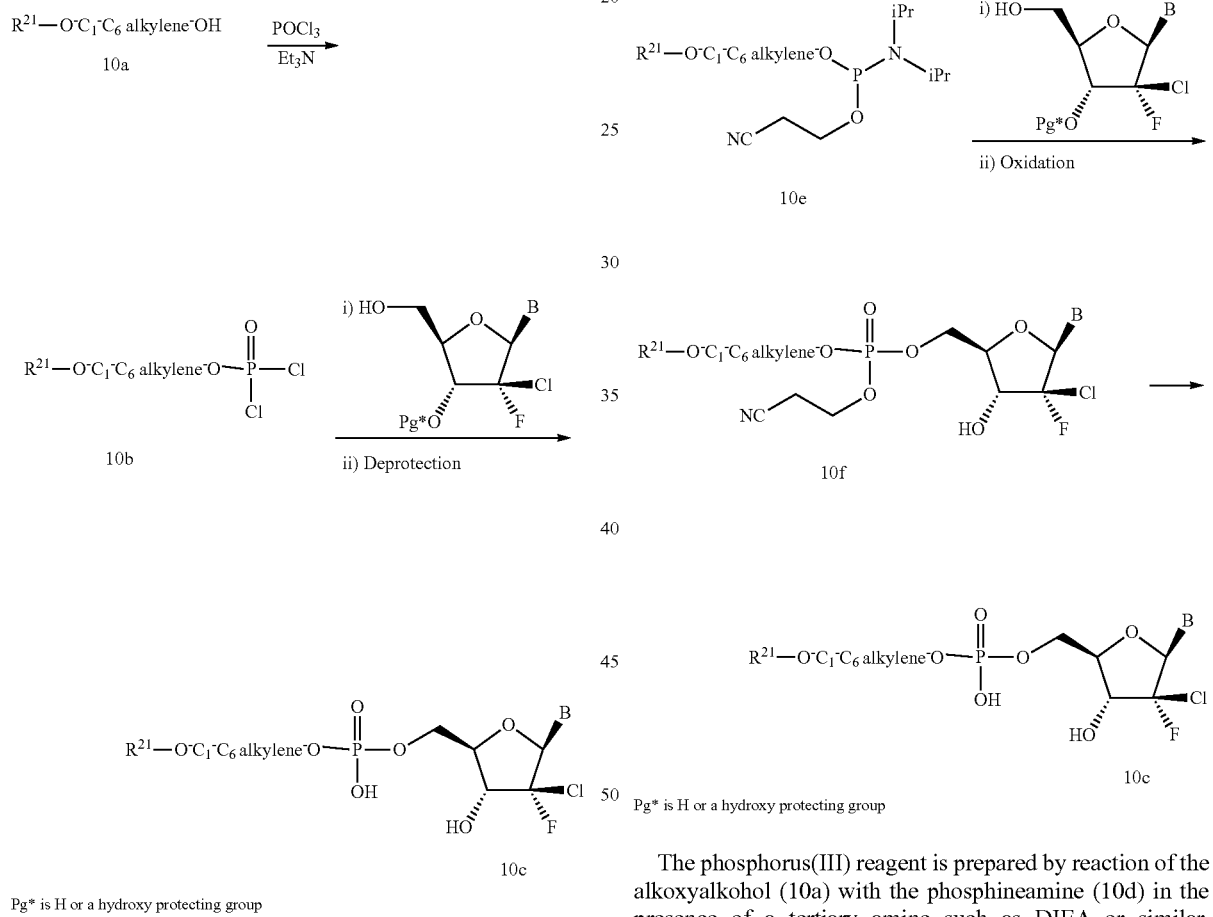

Pg* is H or a hydroxy protecting group

Formation of the phosphorylating agent (10b) performed by reaction of the appropriate alkoxyalkohol (10a) with phosphorus chloride in the present of triethylamine using for instance diethyl ether or the like as solvent, followed by phosphorylation of the optionally protected nucleoside and finally deprotection, provides the protide (10c).

In an alternative approach to compounds of formula I wherein $R^1$ is a prodrug moiety of group (i) wherein U is O, $R^{12}$ is H and $R^{13}$ is of the formula $R^{21}$—O—$C_1$-$C_6$alkylene- and $R^{21}$ is $C_1$-$C_{24}$alkyl, a phosphorus(III)-reagent may be used as phosphorylating agent as illustrated in Scheme 10B.

Scheme 10B

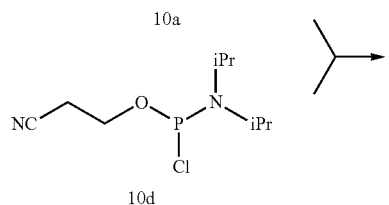

Pg* is H or a hydroxy protecting group

The phosphorus(III) reagent is prepared by reaction of the alkoxyalkohol (10a) with the phosphineamine (10d) in the presence of a tertiary amine such as DIEA or similar. Subsequent phosphorylation of the nucleoside with the afforded phosphoramidite derivative (10e) followed by oxidation using for instance a peroxide, such as tert-butoxy peroxide or the like, provides the nucleotide (10f). Hydrolysis of the cyanoethyl moiety and removal of protecting groups if present, provides the desired nucleotide (10c).

Compounds of formula I, wherein $R^1$ is a prodrug moiety of group (vi) and $R^{13}$ is $R^{21}$C(=O)O—$CH_2$— or $R^{21}$OC(=O)O—$CH_2$— can be prepared according to the methods described in e.g. WO2013/039920 and references cited therein. The method is briefly illustrated in Scheme 11A.

Scheme 11A

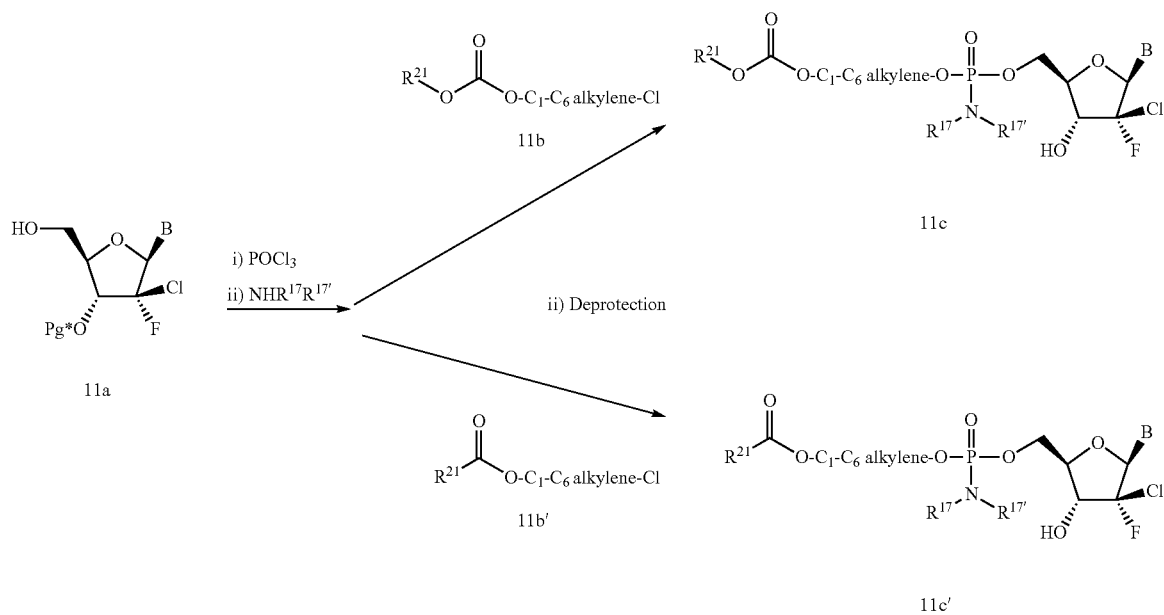

Pg* is H or a hydroxy protection group

The phosphoramidates 11c an 11c' are obtained by reaction of nucleoside 11a with phosphorus oxychloride in triethyl phosphate, followed by reaction with the desired amine $NHR^{17}R^{17'}$ in the presence of DIEA and finally reaction under elevated temperature with the chloroalkyl carbonate (11b) or ester (11b') in the presence of DIEA.

Compounds of formula I, wherein $R^1$ is a prodrug moiety of group (vi) and $R^{13}$ is $R^{21}C(=O)S-CH_2CH_2-$ can be prepared according to the method described in WO2008/082601 and references cited therein. The method is briefly illustrated in Scheme 12A.

Scheme 12A

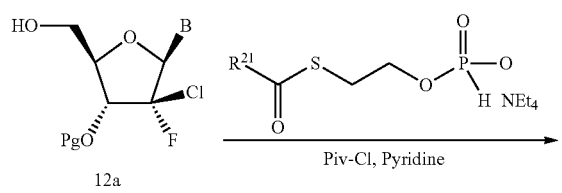

-continued

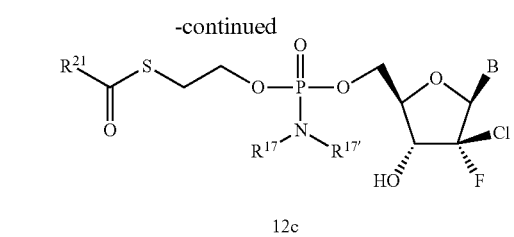

Phosphorylation of 5'-hydroxy compound (12a) with a suitable tetraalkyl ammonium salt, e.g. the tetraethylammmonium salt, of the desired hydrogen phosphonate, effected by activation with pivaloyl chloride in pyridine, provides the hydrogen phosphonate (12b). The amino group $NR^{17}R^{17'}$ is then introduced by reaction with the desired amine in carbontetrachloride under anhydrous conditions, followed by removal of the protecting groups, thus yielding the phosphoramidate (12c).

As an alternative, phosphoramidate (12c) can be achieved from the H-phosphonate (7b) of Scheme 7A by reaction with a desired S-(2-hydroxyethyl) alkanethioate $R^{21}C(C=O)SCH_2CH_2OH$, in the presence of a coupling agent such as PyBOP or the like, followed by amination and deprotection as described above. This route is illustrated in Scheme 12B.

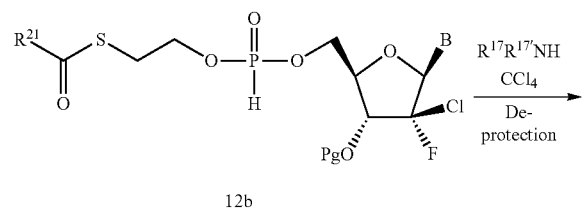

Scheme 12B

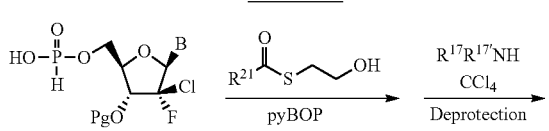

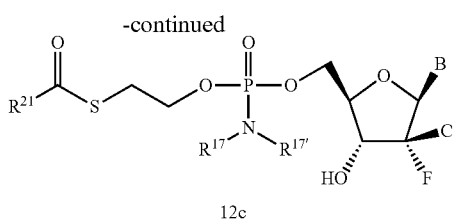

12c

As the skilled person will realise, the procedures illustrated in Schemes 12A and 12B will be applicable not only for the preparation of S-acylthioethanol derivatives, but also of derivatives having other alkylene configurations between the sulfur and oxygen atoms.

Compounds of the invention having an acyl prodrug moiety in the 5'-position and optionally also in the 3'-position, i.e. $R^1$ and optionally also $R^2$ are C(O=)$R^{30}$ or C(=O)$R^{31}NH_2$ can be obtained by subjection of a suitably 3'-protected compound to suitable acylating conditions, as illustrated in Scheme 13.

Scheme 13

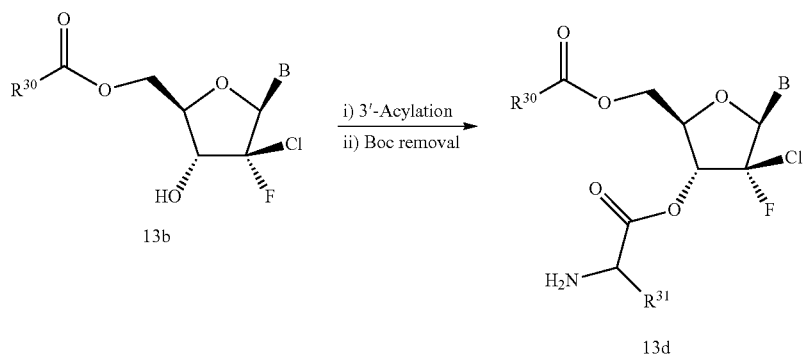

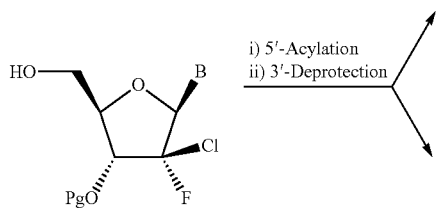

13a

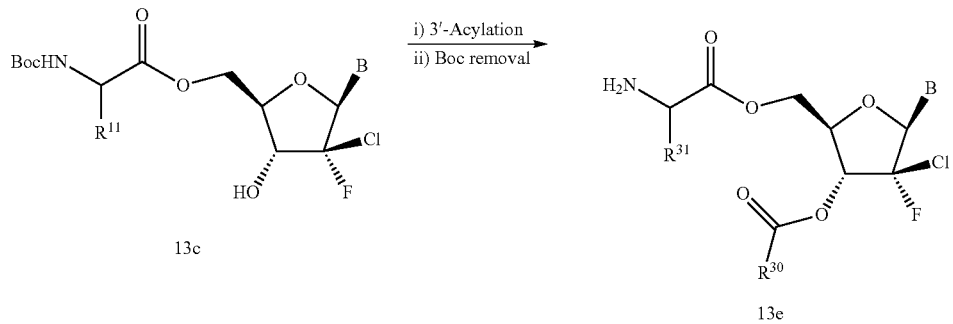

Nucleoside (13b) wherein the prodrug group in the 5'-position is an ester i.e. a group of the formula OC(=O)R$^{10}$, is obtained by reaction of the 5'-hydroxy compound (9a) with the appropriate acylating agent using standard methods, such as using an alkyl acid anhydride, R$^{30}$C(=O)OC(=O)R$^{30}$, in the presence of pyridine, or an alkyl acid chloride, R$^{30}$C(=O)Cl, or the like, whereas nucleosides (13d) carrying an amino acid ester in the 5'-position will be obtained by reaction of the 5'-hydroxy compound (13a) with an N-protected aliphatic amino acid in the presence of a suitable peptide coupling reagent such as EDAC or the like. Removal of the 3'-hydroxy protecting group then yields compounds of the invention wherein R$^1$ is H. On the other hand, subjection of the 3'-hydroxy compounds (13b) and (13c) to the acylation conditions described immediately above, yields the diacyl derivatives (13d) and (13e) respectively.

Compounds of the invention carrying an ester or amino acid ester prodrug moiety in the 5'- and/or 3'-position may be prepared as illustrated in Scheme 14.

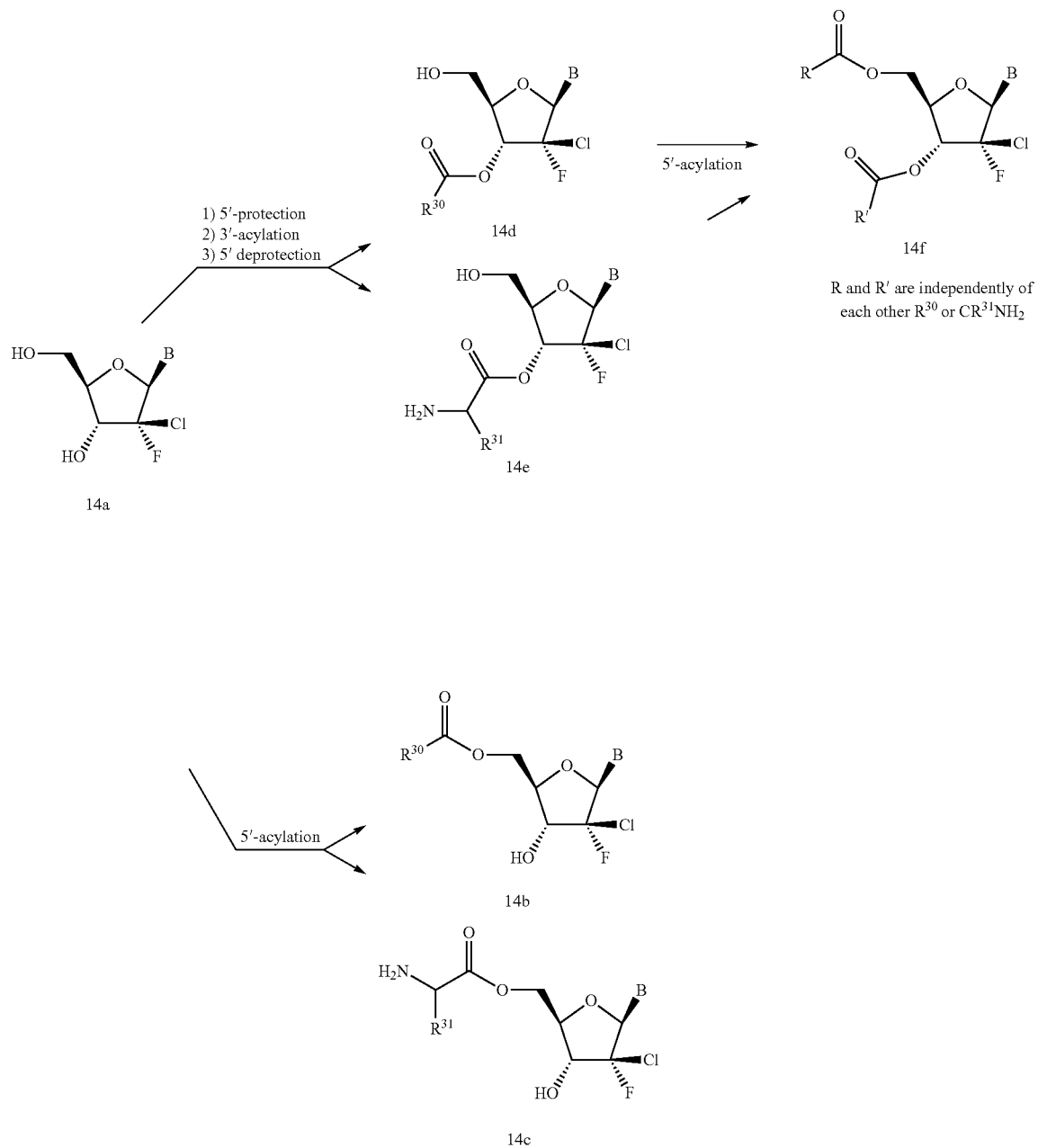

Due to the higher reactivity of the primary 5'-position of the diol (14a), this position can be selectively reacted with a suitable acylating agent to obtain 5'-acyl derivatives (14b) and (14c), or it can be protected with a suitable protecting group to allow for subsequent acylation of the 3'-position. Nucleosides (14b) wherein the prodrug group in the 5'-position is an ester i.e. a group of the formula OC(=O)R$^{30}$, are conveniently obtained by reaction with acylating agent such as an alkyl anhydride in the presence of pyridine, or an acid chloride or the like, whereas nucleosides (14c) carrying an amino acid ester in the 5'-position will be obtained by reaction of the diol (14a) with an N-protected aliphatic amino acid in the presence of a suitable peptide coupling reagent such as EDAC or the like. If an acyl prodrug group is desired in the 3'-position, a protection-acylation-deprotection sequence will be appropriate in order to get clean reactions with descent yields. Typically, a protecting group like a silyl, trityl or a monomethoxy trityl (MMT) group will be suitable to protect the 5'-hydroxy group. The use of these groups are extensively described in the literature, typically, conditions like reaction with the corresponding halide, such as the chloride in a solvent like pyridine is used for their introduction. Subsequent acylation performed as described above, followed by removal of the 5'-O-protecting group, and in case of the amino acid ester being introduced as an N-protected amino acid, the N-protecting group, using the appropriate conditions according to the protecting group used, such as acidic treatment in the case of a trityl or methoxy trityl protecting group, then provides the 3'-acylated derivatives (14d) and (14e). If desired, a phosphoramidate can be introduced in the 5'-position of the afforded 5'-hydroxy derivatives (14d) and (14e), for example using the procedure described herein above, or a mono-, di- or tri-phosphate may be introduced using standard literature phosphorylation procedures, or the 5'-position may be acylated using the method described above for acylation of the 3'-position.

Compounds of the invention having an acetal prodrug moiety in the 5'-position or in both the 5'- and 3'-positions, i.e. compounds of formula I wherein R$^1$ or both R$^1$ and R$^2$ is CR$^{32}$R$^{32'}$OC(=O)CHR$^{33}$NH$_2$ can be prepared from the 5'-hydroxy compound using for example the method described in Bioorg. Med. Chem. 11 (2003)2453-2461.

Compounds of the invention carrying a "HepDirect" prodrug moiety in the 5'-position, i.e. a compound of formula I wherein R$^1$ is the group (i), and R$^{12}$ and R$^{13}$ join to form a propylene group between the oxygen atoms to which they are attached, can be prepared according to the method described in J. Am. Chem. Soc., Vol. 126, No. 16, 2004, p. 5154-5163.

A route to compounds of formula I wherein B is the group (a) or (b), R$^2$ is H and R$^1$ is a triphosphate, i.e. a group of formula (iii), wherein U is O, is illustrated in Scheme 15.

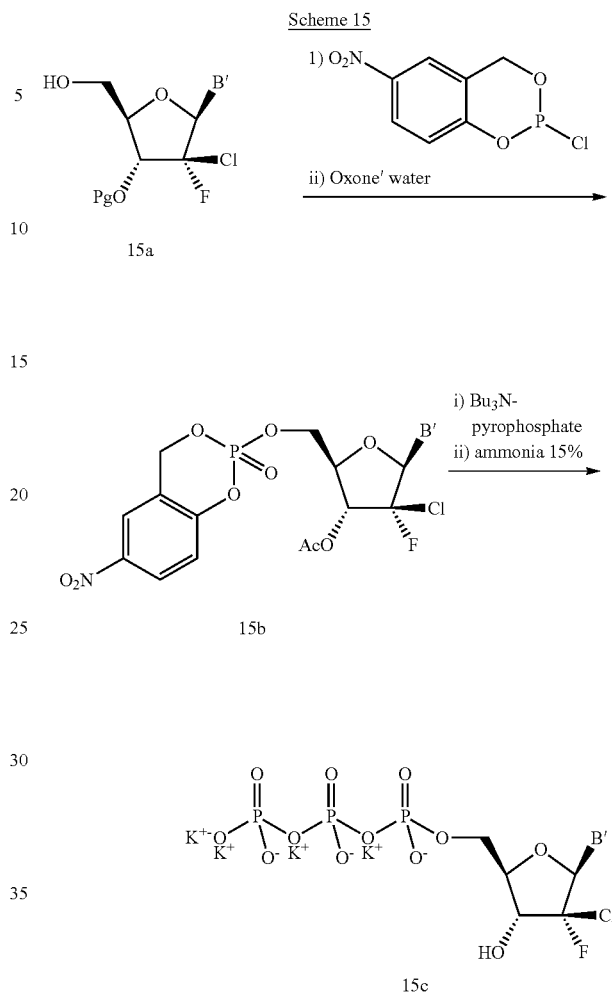

B' is the group (a) or (b) which is optionally protected.

A suitable phosphorylating agent for the preparation of the triphosphate of the compounds of formula (I) wherein B is the group (a) or (b) is 5-nitrocyclosalgenylchlorophosphite (I-6), which is prepared by reaction of phosphorous trichloride and 2-hydroxy-5-nitrobenzyl alcohol as detailed in the experimental part herein below.

Reaction of a suitably 3'-O-protected derivative of the nucleoside of the invention (15a) with nitrocyclosalgenyl-chlorophosphite (I-1) in the presence of Et$_3$N in an inert solvent like DCM or MeCN, followed by oxidation using for instance Oxone®, provides the cyclic phosphate tri-ester (15b). The triphosphate (15c) is then achieved by reaction with a pyrophosphate for instance tributylamine pyrophosphate followed by treatment with ammonia. In order to get the desired salt form, the triphosphate is subjected to the appropriate ion exchange procedure, for instance, if the potassium salt form is desired, the residue is passed through a column Dowex®-K$^+$.

A route to compounds of formula I wherein B is uracil, R$^2$ is H and R$^1$ is a thio-triphosphate, i.e. a group of formula (iii), wherein U is S, is illustrated in Scheme 16.

Scheme 16

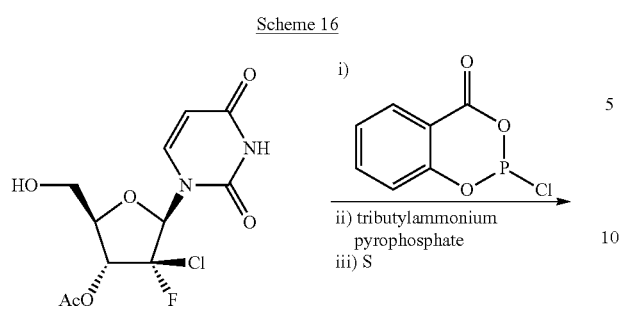

16a

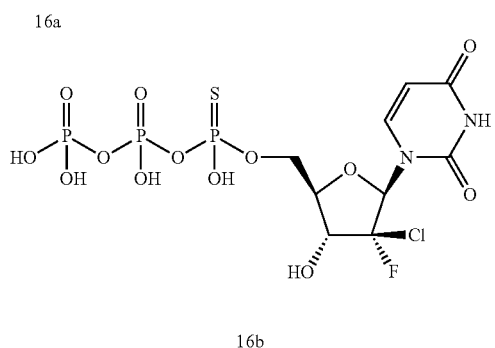

16b

A suitable agent for introduction of the first phosphate group in the preparation of a thio-triphosphate of the U-nucleoside of a compound of formula (I) is 2-chloro-4H-1,3,2-benzodioxaphosphorin-4-one, which is prepared according to literature procedures.

A suitably 3'-O-protected nucleoside is thus reacted with 2-chloro-4H-1,3,2-benzodioxaphosphorin-4-one in a solvent like pyridine/THF or equivalent followed by treatment with tributylammonium pyrophosphate in the presence of tributylamine in a solvent like DMF. The afforded intermediate is then transformed to the thiotriphosphate by treatment with a solution of sulfur in DMF. In order to get the desired salt form, the triphosphate is subjected to the appropriate ion exchange procedure, for instance, if the lithium salt form is desired, the residue is passed through a column Dowex®-Li$^+$.

An alternative route to the thio-triphosphate is illustrated in Scheme 17.

Scheme 17

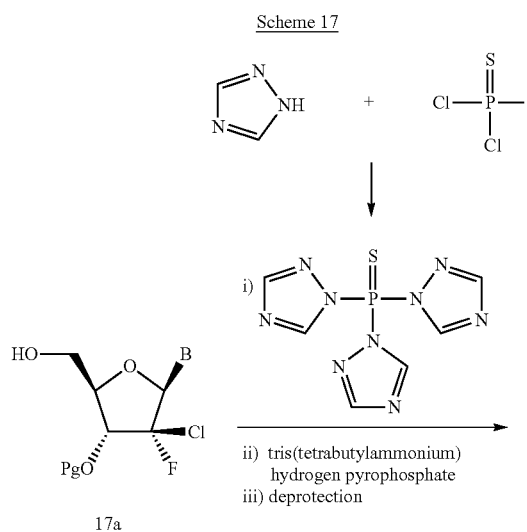

17a

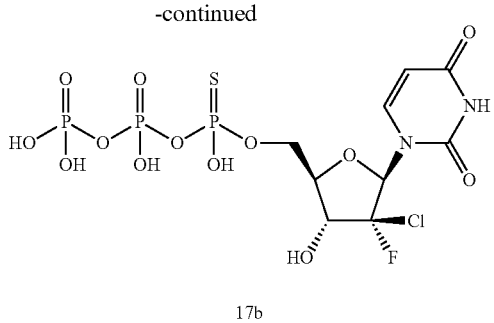

17b

In this method, a thiophosphate reagent is used in the phosphorylation step. The reagent is prepared by reaction of PSCl$_3$ and triazole in a solvent like MeCN or similar. The thus formed reagent is then coupled to the 3'-O-protected nucleoside 13a, whereafter a reaction with a pyrophosphate such as tris(tetrabutylammonium) hydrogen pyrophosphate is performed, thus providing the thio-triphosphate (17b).

The use of various protecting groups (PG) used in schemes above are known to the skilled person, and their utility and further alternatives are extensively described in the literature, see for instance Greene T. W., Wuts P. G. M. Protective groups in organic synthesis, 2nd ed. New York: Wiley; 1995.

The term "N-protecting group" or "N-protected" as used herein refers to those groups intended to protect the N-terminus of an amino acid or peptide or to protect an amino group against undesirable reactions during synthetic procedures. Commonly used N-protecting groups are disclosed in Greene. N-protecting groups include acyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, α-chlorobutyryl, benzoyl, 4-chlorobenzoyl, 4-bromobenzoyl, 4-nitrobenzoyl, and the like; sulfonyl groups such as benzenesulfonyl, p-toluenesulfonyl, and the like; carbamate forming groups such as benzyloxycarbonyl, p-chlorobenzyloxy-carbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenyl)-1-methylethoxycarbonyl, α,α-dimethyl-3,5-dimethoxybenzyloxycarbonyl, benzhydryloxycarbonyl, t-butoxycarbonyl, diisopropylmethoxycarbonyl, isopropyloxycarbonyl, ethoxycarbonyl, methoxycarbonyl, allyloxycarbonyl, 2,2,2-trichloroethoxycarbonyl, phenoxycarbonyl, 4-nitrophenoxycarbonyl, fluorenyl-9-methoxycarbonyl, cyclopentyloxycarbonyl, adamantyloxycarbonyl, cyclohexyloxycarbonyl, phenylthiocarbonyl, and the like; alkyl groups such as benzyl, triphenylmethyl, benzyloxymethyl and the like; and silyl groups such as trimethylsilyl and the like. Favoured N-protecting groups include formyl, acetyl, benzoyl, pivaloyl, t-butylacetyl, phenylsulfonyl, benzyl (Bz), t-butoxycarbonyl (BOC) and benzyloxycarbonyl (Cbz).

Hydroxy and/or carboxy protecting groups are also extensively reviewed in Greene ibid and include ethers such as methyl, substituted methyl ethers such as methoxymethyl, methylthiomethyl, benzyloxymethyl, t-butoxymethyl, 2-methoxyethoxymethyl and the like, silyl ethers such as trimethylsilyl (TMS), t-butyldimethylsilyl (TBDMS) tribenzylsilyl, triphenylsilyl, t-butyldiphenylsilyl, triisopropyl silyl and the like, substituted ethyl ethers such as 1-ethoxymethyl, 1-methyl-1-methoxyethyl, t-butyl, allyl, benzyl, p-methoxybenzyl, diphenylmethyl, triphenylmethyl and the like, aralkyl groups such as trityl, and pixyl (9-hydroxy-9-phenylxanthene derivatives, especially the chloride). Ester hydroxy protecting groups include esters such as formate, benzylformate, chloroacetate, methoxyacetate, phenoxyacetate, pivaloate, adamantoate, mesitoate, benzoate and the like. Carbonate hydroxy protecting groups include methyl vinyl, allyl, cinnamyl, benzyl and the like.

In one aspect, the present invention concerns a pharmaceutical composition comprising a therapeutically effective amount of a compound of formula I, and a pharmaceutically acceptable carrier. A therapeutically effective amount in this context is an amount sufficient to stabilize or to reduce viral infection, and in particular HCV infection, in infected subjects (e.g. humans). The "therapeutically effective amount" will vary depending on individual requirements in each particular case. Features that influence the dose are e.g. the severity of the disease to be treated, age, weight, general health condition etc. of the subject to be treated, route and form of administration.

In one aspect, the invention relates to the use of a compound of formula I, for the treatment of "treatment naive" patients, i.e. patients infected with HCV that are not previously treated against the infection.

In another aspect the invention relates to the use of a compound of formula I, the treatment of "treatment experienced" patients, i.e. patients infected with HCV that are previously treated against the infection and have subsequently relapsed.

In another aspect the invention relates to the use of a compound of formula I, the treatment of "non-responders", i.e. patients infected with HCV that are previously treated but have failed to respond to the treatment.

In a further aspect, the present invention concerns a pharmaceutical composition comprising a prophylactically effective amount of a compound of formula I as specified herein, and a pharmaceutically acceptable carrier. A prophylactically effective amount in this context is an amount sufficient to act in a prophylactic way against HCV infection, in subjects being at risk of being infected.

In still a further aspect, this invention relates to a process of preparing a pharmaceutical composition as specified herein, which comprises intimately mixing a pharmaceutically acceptable carrier with a therapeutically or prophylactically effective amount of a compound of formula I, as specified herein.

Therefore, the compounds of the present invention may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in addition salt form or solvate, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, particularly, for administration orally, rectally, percutaneously, or by parenteral injection. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, lubricants, binders, disintegrating agents and the like in the case of powders, pills, capsules, and tablets. Because of their ease in administration, tablets and capsules represent the most advantageous oral dosage unit forms, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. The compounds of the present invention may also be administered via oral inhalation or insufflation in the form of a solution, a suspension or a dry powder using any art-known delivery system.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, suppositories, powder packets, wafers, injectable solutions or suspensions and the like, and segregated multiples thereof The compounds of formula I show activity against HCV and can be used in the treatment and/or prophylaxis of HCV infection or diseases associated with HCV. Typically the compounds of formula I can be used in the treatment of HCV infection or diseases associated with HCV. Diseases associated with HCV include progressive liver fibrosis, inflammation and necrosis leading to cirrhosis, end-stage liver disease, and HCC. A number of the compounds of this invention may be active against mutated strains of HCV. Additionally, many of the compounds of this invention may show a favourable pharmacokinetic profile and have attractive properties in terms of bioavailability, including an acceptable half-life, AUC (area under the curve) and peak values and lacking unfavourable phenomena such as insufficient quick onset and tissue retention.

The in vitro antiviral activity against HCV of the compounds of formula I can be tested in a cellular HCV replicon system based on Lohmann et al. (1999) Science 285:110-113, with the further modifications described by Krieger et al. (2001) Journal of Virology 75: 4614-4624 (incorporated herein by reference), which is further exemplified in the examples section. This model, while not a complete infection model for HCV, is widely accepted as the most robust and efficient model of autonomous HCV RNA replication currently available. It will be appreciated that it is important to distinguish between compounds that specifically interfere with HCV functions from those that exert cytotoxic or cytostatic effects in the HCV replicon model, and as a consequence cause a decrease in HCV RNA or linked reporter enzyme concentration. Assays are known in the field for the evaluation of cellular cytotoxicity based for example on the activity of mitochondrial enzymes using fluorogenic redox dyes such as resazurin. Furthermore, cellular counter screens exist for the evaluation of non-selective inhibition of linked reporter gene activity, such as firefly luciferase. Appropriate cell types can be equipped by stable transfection with a luciferase reporter gene whose expression is dependent on a constitutively active gene promoter, and such cells can be used as a counter-screen to eliminate non-selective inhibitors.

Due to their antiviral properties, particularly their anti-HCV properties, the compounds of formula I, including any possible stereoisomers, the pharmaceutically acceptable addition salts or solvates thereof, are useful in the treatment of warm-blooded animals, in particular humans, infected with HCV. The compounds of formula I are further useful for the prophylaxis of HCV infections. The present invention furthermore relates to a method of treating a warm-blooded animal, in particular human, infected by HCV, or being at risk of infection by HCV, said method comprising the administration of an anti-HCV effective amount of a compound of formula I.

The compounds of the present invention may therefore be used as a medicine, in particular as an anti HCV medicine. Said use as a medicine or method of treatment comprises the systemic administration to HCV infected subjects or to subjects susceptible to HCV infection of an amount effective to combat the conditions associated with HCV infection.

The present invention also relates to the use of the present compounds in the manufacture of a medicament for the treatment or the prevention of HCV infection.

In a preferred embodiment, the present invention relates to the use of the compounds of formula I in the manufacture of a medicament for the treatment of HCV infection.

In general it is contemplated that an antiviral effective daily amount would be from about 0.01 to about 700 mg/kg, or about 0.5 to about 400 mg/kg, or about 1 to about 250 mg/kg, or about 2 to about 200 mg/kg, or about 10 to about 150 mg/kg body weight. It may be appropriate to administer the required dose as two, three, four or more sub-doses at appropriate intervals throughout the day. Said sub-doses may be formulated as unit dosage forms, for example, containing about 1 to about 5000 mg, or about 50 to about 3000 mg, or about 100 to about 1000 mg, or about 200 to about 600 mg, or about 100 to about 400 mg of active ingredient per unit dosage form.

The invention also relates to a combination of a compound of formula I, a pharmaceutically acceptable salt or solvate thereof, and another antiviral compound, in particular another anti-HCV compound. The term "combination" may relate to a product containing (a) a compound of formula I and (b) optionally another anti-HCV compound, as a combined preparation for simultaneous, separate or sequential use in treatment of HCV infections.

Anti-HCV compounds that can be used in such combinations include HCV polymerase inhibitors, HCV protease inhibitors, inhibitors of other targets in the HCV life cycle, and an immunomodulatory agents, and combinations thereof. HCV polymerase inhibitors include, NM283 (valopicitabine), R803, JTK-109, JTK-003, HCV-371, HCV-086, HCV-796 and R-1479, R-7128, MK-0608, VCH-759, PF-868554, GS9190, XTL-2125, NM-107, GSK625433, R-1626, BILB-1941, ANA-598, IDX-184, IDX-375, INX-189, MK-3281, MK-1220, ABT-333, PSI-7851, PSI-6130, GS-7977 (sofosbuvir), VCH-916. Inhibitors of HCV proteases (NS2-NS3 inhibitors and NS3-NS4A inhibitors) include BILN-2061, VX-950 (telaprevir), GS-9132 (ACH-806), SCH-503034 (boceprevir), TMC435350 (simeprevir), TMC493706, ITMN-191, MK-7009, BI-12202, BILN-2065, BI-201335, BMS-605339, R-7227, VX-500, BMS650032, VBY-376, VX-813, SCH-6, PHX-1766, ACH-1625, IDX-136, IDX-316. An example of an HCV NS5A inhibitor is BMS790052, A-831, A-689, NIM-811 and DEBIO-025 are examples of NS5B cyclophilin inhibitors.

Inhibitors of other targets in the HCV life cycle, including NS3 helicase; metalloprotease inhibitors; antisense oligonucleotide inhibitors, such as ISIS-14803 and AVI-4065; siRNA's such as SIRPLEX-140-N; vector-encoded short hairpin RNA (shRNA); DNAzymes; HCV specific ribozymes such as heptazyme, RPI.13919; entry inhibitors such as HepeX-C, HuMax-HepC; alpha glucosidase inhibitors such as celgosivir, UT-231B and the like; KPE-02003002; and BIVN 401.

Immunomodulatory agents include, natural and recombinant interferon isoform compounds, including α-interferon, β-interferon, γ-interferon, and ω-interferon, such as Intron A®, Roferon-A®, Canferon-A300®, Advaferon®, Infergen®, Humoferon®, Sumiferon MP®, Alfaferone®, IFN-beta®, and Feron®; polyethylene glycol derivatized (pegylated) interferon compounds, such as PEG interferon-α-2a (Pegasys®), PEG interferon-α-Th (PEG-Intron®), and pegylated IFN-α-con1; long acting formulations and derivatizations of interferon compounds such as the albumin-fused interferon albuferon α; compounds that stimulate the synthesis of interferon in cells, such as resiquimod; interleukins; compounds that enhance the development of type 1 helper T cell response, such as SCV-07; TOLL-like receptor agonists such as CpG-10101 (actilon), and isatoribine; thymosin α-1; ANA-245; ANA-246; histamine dihydrochloride; propagermanium; tetrachlorodecaoxide; ampligen; IMP-321; KRN-7000; antibodies, such as civacir and XTL-6865; and prophylactic and therapeutic vaccines such as InnoVac C and HCV E1E2/MF59.

Other antiviral agents include, ribavirin, amantadine, viramidine, nitazoxanide; telbivudine; NOV-205; taribavirin; inhibitors of internal ribosome entry; broad-spectrum viral inhibitors, such as IMPDH inhibitors, and mycophenolic acid and derivatives thereof, and including, but not limited to, VX-497 (merimepodib), VX-148, and/or VX-944); or combinations of any of the above.

Particular agents for use in said combinations include interferon-α (IFN-α), pegylated interferon-α or ribavirin, as well as therapeutics based on antibodies targeted against HCV epitopes, small interfering RNA (Si RNA), ribozymes, DNAzymes, antisense RNA, small molecule antagonists of for instance NS3 protease, NS3 helicase and NS5B polymerase.

In another aspect there are provided combinations of a compound of formula I as specified herein and an anti-HIV compound. The latter preferably are those HIV inhibitors that have a positive effect on drug metabolism and/or pharmacokinetics that improve bioavailability. An example of such an HIV inhibitor is ritonavir. As such, this invention further provides a combination comprising (a) a compound of formula I or a pharmaceutically acceptable salt or solvate thereof; and (b) ritonavir or a pharmaceutically acceptable salt thereof. The compound ritonavir, its pharmaceutically acceptable salts, and methods for its preparation are described in WO 94/14436. U.S. Pat. No. 6,037,157, and references cited therein: U.S. Pat. No. 5,484,801, U.S. Ser. No. 08/402,690, WO 95/07696, and WO 95/09614, disclose preferred dosage forms of ritonavir.

The invention also concerns a process for preparing a combination as described herein, comprising the step of combining a compound of formula I and another agent, such as an antiviral, including an anti-HCV or anti-HIV agent, in particular those mentioned above.

The said combinations may find use in the manufacture of a medicament for treating HCV infection in a mammal infected therewith, said combination in particular comprising a compound of formula I, as specified above and interferon-α (IFN-α), pegylated interferon-α, or ribavirin. Or the invention provides a method of treating a mammal, in particular a human, infected with HCV comprising the administration to said mammal of an effective amount of a combination as specified herein. In particular, said treating comprises the systemic administration of the said combination, and an effective amount is such amount that is effective in treating the clinical conditions associated with HCV infection.

In one embodiment the above-mentioned combinations are formulated in the form of a pharmaceutical composition that includes the active ingredients described above and a carrier, as described above. Each of the active ingredients may be formulated separately and the formulations may be co-administered, or one formulation containing both and if desired further active ingredients may be provided. In the former instance, the combinations may also be formulated as a combined preparation for simultaneous, separate or sequential use in HCV therapy. The said composition may take any of the forms described above. In one embodiment, both ingredients are formulated in one dosage form such as a fixed dosage combination. In a particular embodiment, the present invention provides a pharmaceutical composition comprising (a) a therapeutically effective amount of a compound of formula I, including a possible stereoisomeric form thereof, or a pharmaceutically acceptable salt thereof, or a pharmaceutically acceptable solvate thereof, and (b) a therapeutically effective amount of ritonavir or a pharmaceutically acceptable salt thereof, and (c) a carrier.

The individual components of the combinations of the present invention can be administered separately at different times during the course of therapy or concurrently in divided or single combination forms. The present invention is meant to embrace all such regimes of simultaneous or alternating treatment and the term "administering" is to be interpreted accordingly. In a preferred embodiment, the separate dosage forms are administered simultaneously.

In one embodiment, the combinations of the present invention contain an amount of ritonavir, or a pharmaceutically acceptable salt thereof, that is sufficient to clinically improve the bioavailability of the compound of formula I relative to the bioavailability when said compound of formula I is administered alone. Or, the combinations of the present invention contains an amount of ritonavir, or a pharmaceutically acceptable salt thereof, which is sufficient to increase at least one of the pharmacokinetic variables of the compound of formula I selected from $t_{1/2}$, $C_{min}$, $C_{max}$, $C_{ss}$, AUC at 12 hours, or AUC at 24 hours, relative to said at least one pharmacokinetic variable when the compound of formula I is administered alone.

The combinations of this invention can be administered to humans in dosage ranges specific for each component comprised in said combinations, e.g. the compound of formula I as specified above, and ritonavir or a pharmaceutically acceptable salt, may have dosage levels in the range of 0.02 to 5.0 g/day.

The weight ratio of the compound of formula I to ritonavir may be in the range of from about 30:1 to about 1:15, or about 15:1 to about 1:10, or about 15:1 to about 1:1, or about 10:1 to about 1:1, or about 8:1 to about 1:1, or about 5:1 to about 1:1, or about 3:1 to about 1:1, or about 2:1 to 1:1. The compound formula I and ritonavir may be co-administered once or twice a day, preferably orally, wherein the amount of the compound of formula I per dose is as described above; and the amount of ritonavir per dose is from 1 to about 2500 mg, or about 50 to about 1500 mg, or about 100 to about 800 mg, or about 100 to about 400 mg, or 40 to about 100 mg of ritonavir.

DETAILED DESCRIPTION OF THE EMBODIMENTS

Various embodiments of the invention and intermediates therefore will now be illustrated by the following examples. The Examples are just intended to further illustrate the invention and are by no means limiting the scope of the invention. The compound names were generated by ChemDraw Ultra software, Cambridgesoft, version 12.0.2.

In addition to the definitions above, the following abbreviations are used in the examples and synthetic schemes below. If an abbreviation used herein is not defined, it has its generally accepted meaning Bn Benzyl
Bz Benzoyl
BOP—Cl Bis(2-oxo-3-oxazolidinyl)phosphinic chloride
Bz Benzoyl
DCC Dicyclohexylcarbodiimide DCM Dichloromethane
DIEA Diisopropylethylamine
DMAP 4-Dimethylaminopyridine
DMF N,N-Dimethylformamide
DMPU 1,3-Dimethyl-3,4,5,6-tetrahydro-2-pyrimidinone
EDC 1-(3-Dimethylaminopropyl)-3-ethylcarbodiimide hydrochloride
ES Electrospray
$Et_3N$ Triethylamine
EtOAc Ethyl acetate
EtOH Ethanol
$Et_2O$ Diethyl ether
LC Liquid chromatography
HOAc Acetic acid
HPLC High performance liquid chromatography
MeCN Acetonitrile
MeOH Methanol
MS Mass spectrometry
NT 3-nitro-1,2,4-triazole
NTP Nucleoside triphosphate
Pg Protecting group
Ph Phenyl
SEM Standard error of the mean
TEST bis(triethoxysilyl)propyl-tetrasulfide
THF Tetrahydrofuran
TFA Trifluoroacetic acid
TFAA Trifluoroacetic anhydride
TIPS Triisopropylsilyl The following phenols were prepared and used in the preparation of intermediates to the compounds of the invention:

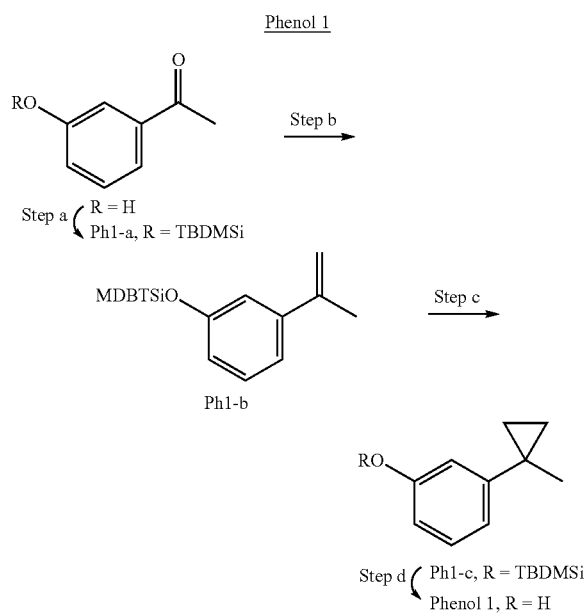

Phenol 1

Step a) 1-(3-((Tert-butyldimethylsilyl)oxy)phenyl)ethanone (Ph1-a)

Imidazole (4.46 g, 65.5 mmol) was added to a solution of 3-hydroxyacetophenone (4.46 g, 32.8 mmol) in DMF (6 mL). After 5 min, a solution of TBDMS-Cl (4.69 g, 31.1 mmol) in DMF (4 mL) was added. The reaction mixture was stirred at room temperature for 90 min, then poured into hexane containing 5% EtOAc (200 mL) and washed with 1M HCl (60 mL), water (60 mL), saturated sodium bicarbonate (2×60 mL), water (60 mL) and brine (60 mL). The organic layer was dried over $Na_2SO_4$, filtered and concentrated and the afforded residue was purified by flash chromatography on silica gel eluted with hexane/EtOAc, which gave the title compound (5.7 g, 69%).

Step b) Tert-butyldimethyl(3-(prop-1-en-2-yl)phenoxy)silane (Ph1-b)

Methyl(triphenylphosphonium)bromide (10.2 g, 28.4 mmol) was suspended in dry THF (30 mL) under nitrogen and the suspension was cooled to 0° C. n-Butyllithium (17.8 mL, 28.4 mmol) was added drop-wise to the mixture and the resulting solution was stirred at room temperature for 30 min. Ph1-a (5.7 g, 22.8 mmol) was added to the mixture and the reaction allowed to proceed at room temperature for 60 min. The reaction was quenched with aqueous sodium bicarbonate and extracted with diethyl ether (50 mL). The organic layer was washed with sodium bicarbonate solution, dried ($Na_2SO_4$), filtered and concentrated. The afforded residue was purified through a plug of silica-gel using eluted with hexane, which gave the title compound (3.9 g, 69%).

Step c) Tert-butyldimethyl(3-(1-methylcyclopropyl)phenoxy)silane (Ph1-c)

Diethylzinc in hexane (439.2 mmol) was added drop-wise under nitrogen during 10 minutes to a cooled (0° C.) solution of the olefin Ph1-b (3.9 g, 15.7 mmol) in 1,2-dichloroethane (60 mL). Diiodomethane (6.32 mL, 78.5 mmol) was added drop-wise and the resulting mixture was stirred at 0° C. for 30 min and then allowed to attain room temperature overnight. The mixture was poured into an ice-cold solution of ammonium chloride and extracted with diethyl ether. The organic layer was washed with saturated sodium bicarbonate, dried ($Na_2SO_4$), filtered and concentrated. The crude was taken into hexane and the remaining diiodomethane was discarded. The hexane layer was concentrated to a crude that was taken into the next step without further purification.

Step d) 3-(1-Methylcyclopropyl)phenol (Phenol 1)

Ph1-c (3.45 g, 13.1 mmol) was taken into 1M solution of tetrabutylammonium fluoride in THF (20 mL, 20 mmol) and the resulting solution was stirred at room temperature overnight. The reaction was quenched with 1M HCl (50 mL) and extracted with ethyl acetate (100 mL). The organic layer was washed with brine (2×50 mL), dried ($Na_2SO_4$), filtered and concentrated. The residue was purified by flash chromatography on silica gel eluted with a mixture of 2-propanol, EtOAc and hexane, which gave the title compound (0.56 g, 29%). MS 147.1 [M−H]⁻.

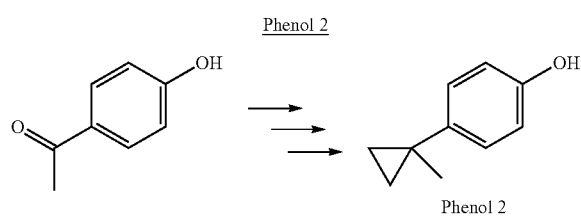

The title compound was prepared from 4-hydroxyacetophenone (6.0 g, 44.1 mmol) using the method described for the preparation of Phenol 1. Yield 53%.

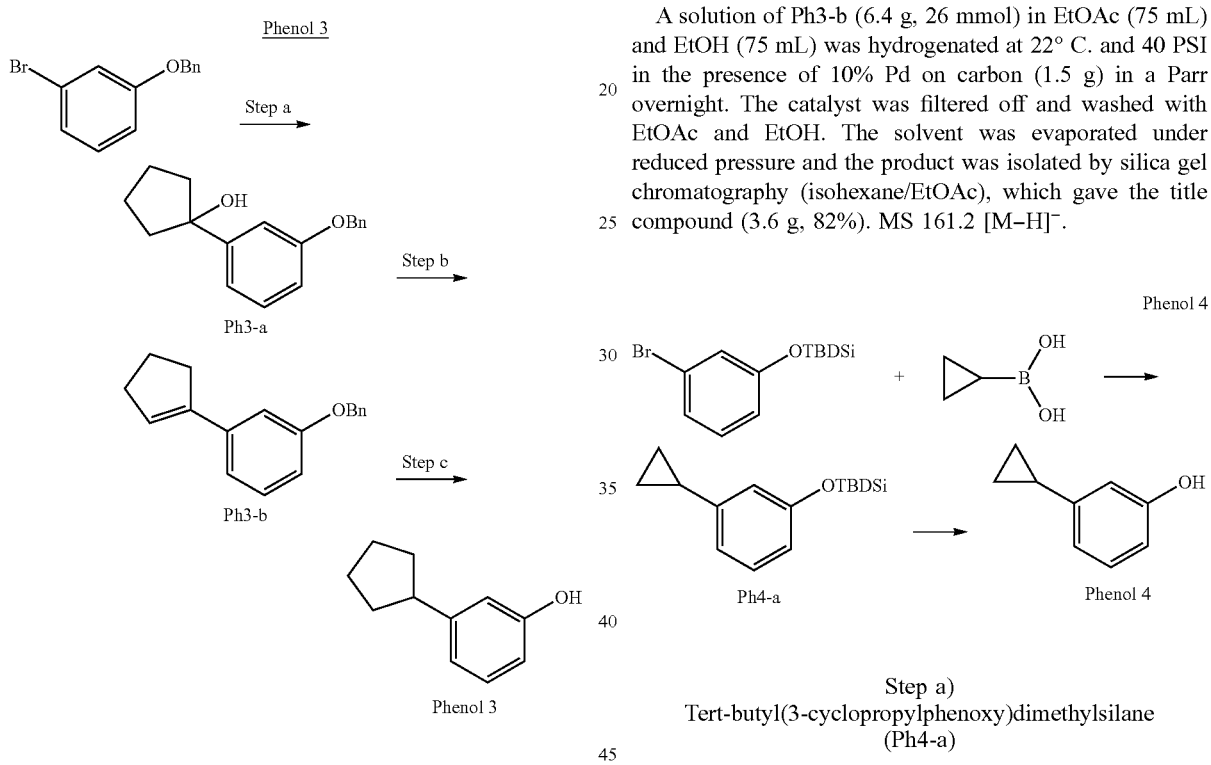

Step a) 1-(3-(benzyloxy)phenyl)cyclopentanol (Ph3-a)

Iodine, warmed up with magnesium, was added to a suspension of magnesium tunings (1.29 g, 52.8 mmol) in dry THF (50 mL). The mixture was refluxed and about 5% of a solution of 3-bromophenol (13.9 g, 52.8 mmol) was added. When the reaction had started, the solution of the bromide was added drop-wise and the mixture was then refluxed for one more hour. The mixture was cooled down to about 5° C. and a solution of the cyclopentanone (4.44 g, 52.8 mmol) in THF (50 mL) was added drop-wise. The mixture was stirred at rt for 72 h, then the reactio was quenched with cooled saturated ammonium chloride solution and extracted with diethyl ether (×3). The organic phase was washed with brine, dried ($Na_2SO_4$), filtered and concentrated. The product was purified by silica gel chromatography (isohexane/EtOAc), which gave the title compound (8.5 g, 54%).

Step b) 1-(benzyloxy)-3-(cyclopent-1-en-1-yl)benzene (Ph3-b)

p-Toluenesulfonic acid was added to a solution of Ph3-a (8.4 g, 28.2 mmol) in benzene (100 mL). The mixture was refluxed for three hours with a DMF trap, then cooled to rt, diluted with diethyl ether and washed with a saturated solution of sodium hydrogen carbonate and brine. The organic phase was dried ($Na_2SO_4$), filtered and concentrated. The product was purified by silica gel chromatography (isohexane/EtOAc), which gave the title compound (6.45 g, 91%). MS 249.4 [M−H]⁻.

Step c) 3-Cyclopentylphenol (Phenol 3)

A solution of Ph3-b (6.4 g, 26 mmol) in EtOAc (75 mL) and EtOH (75 mL) was hydrogenated at 22° C. and 40 PSI in the presence of 10% Pd on carbon (1.5 g) in a Parr overnight. The catalyst was filtered off and washed with EtOAc and EtOH. The solvent was evaporated under reduced pressure and the product was isolated by silica gel chromatography (isohexane/EtOAc), which gave the title compound (3.6 g, 82%). MS 161.2 [M−H]⁻.

Step a) Tert-butyl(3-cyclopropylphenoxy)dimethylsilane (Ph4-a)

A suspension of (3-bromophenoxy)(tert-butyl)dimethylsilane (5.46 g, 19 mmol), cyclopropylboronic acid (2.12 g, 24.7 mmol), potassium phosphate, tribasic (14.1 g, 66.5 mmol), tricyclohexylphosphine (0.53 g, 1.9 mmol) and Pd(OAc)₂ (0.21 g, 0.95 mmol) in toluene (80 mL) and water (4 mL) was stirred at 110° C. overnight. The slurry was diluted with diethyl ether and washed with water and brine. The organic phase was dried ($MgSO_4$), filtered and concentrated. The crude was purified by flash column chromatography (EtOAc/hexane) which gave the title compound (1.94 g, 41%).

Step b) 3-Cyclopropylphenol (Phenol 4)

1M tetrabutylammonium fluoride (10.1 ml, 10.1 mmol) was added to a solution of Ph4-a (1.94 g, 7.81 mmol) in THF (25 ml). The solution was stirred for 2 hours, then the solvent was evaporated and the residue dissolved in EtOAc and washed twice with concentrated $NH_4Cl$ (aq) and once with brine. The organic phase was dried ($MgSO_4$), filtered and concentrated. The crude was purified by flash column chromatography (hexane/ethyl acetate 9:1 with 1% isopropanol) which gave slightly impure title compound (1.24 g, 119%).

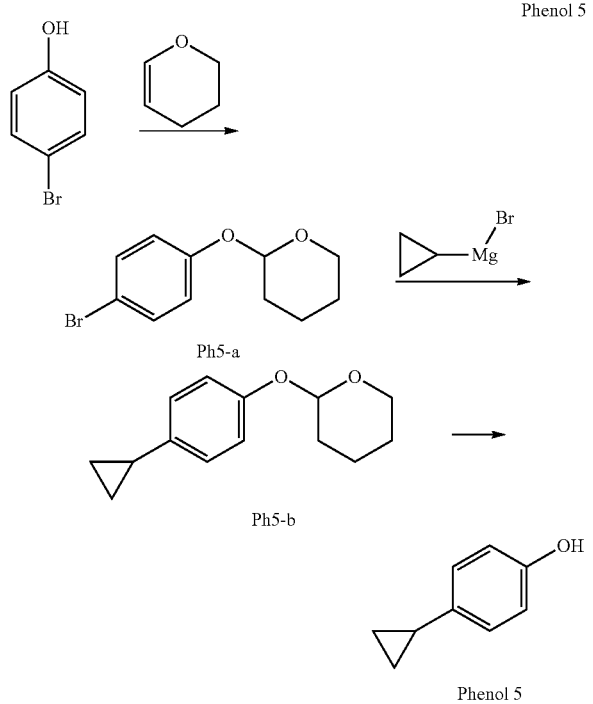

Phenol 5

Ph5-a

Ph5-b

Phenol 5

Step a)
2-(4-Bromophenoxy)tetrahydro-2H-pyran(Ph5-a)

4-Bromphenol (3.75 g, 21.7 mmol) was dissolved in 3,4-dihydro-2H-pyran (16 ml, 175 mmol), a catalytic amount of p-Toluenesulfonic acid (15 mg, 0.09 mmol) was added and the mixture was stirred at 22° C. for 45 min. The mixture was diluted with diethyl ether and washed with 1 M NaOH (aq) ×2, water, dried ($Na_2SO_4$) and concentrated which gave the title compound (5.57 g, 99%).

Step b)
2-(4-Cyclopropylphenoxy)tetrahydro-2H-pyran (Ph5-b)

A solution of 0.5 M cyclopropyl magnesium bromide in THF (6.5 ml, 3.25 mmol) was added during 15 min to a solution of Ph5-a (552.5 mg, 2.15 mmol), ZnBr (144 mg, 0.64 mmol), tri-tert-butylphosphine tetrafluoroborate (35.6 mg, 0.12 mmol) and Pd(OAc)$_2$ (29.5 mg, 0.13 mmol) in THF (4 ml). The mixture was stirred at 22° C. for 90 min then cooled on an ice bath and ice water (10 ml) was added. The mixture was extracted with EtOAc ×3 and the extracts washed with brine and then dried ($Na_2SO_4$), filtered and concentrated. The residue was purified by column chromatography on silica (petroleum ether/EtOAc) which gave the title compound (292 mg, 62%).

Step c) 4-Cyclopropylphenol (Phenol 5)

p-Toluenesulfonic acid monohydrate (18.9 mg, 0.1 mmol) was added to a solution of Ph5-b (2.28 g, 10.45 mmol) in MeOH (15 ml). The mixture was heated at 120° C. for 5 min in a microwave reactor, then concentrated and purified by column chromatography on silica (petroleum ether/EtOAc). The afforded solids were crystallized from petroleum ether which gave the title compound (1.08 g, 77%).

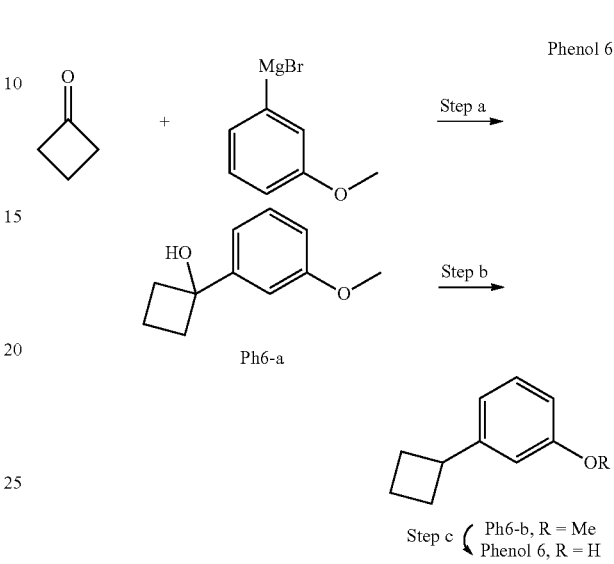

Ph6-a

Ph6-b, R = Me
Phenol 6, R = H

Step a) 1-(3-Methoxyphenyl)cyclobutanol (Ph6-a)

A 1 M solution of 3-methoxyphenyl magnesium bromide in THF (2.11 g, 99.8 mmol) was added dropwise between 0 and 10° C. to a stirred solution of cyclobutanone (6.66 g, 95 mmol) in diethyl ether (65 mL). The mixture was stirred for three hours at 0-10° C., then the mixture was added to an ice cooled solution of saturated $NH_4Cl$ (300 mL) and water (300 mL). The mixture was stirred for 10 min then extracted three times with diethyl ether. The organic phase was dried, ($Na_2SO_4$), filtered and concentrate. The afforded crude product was purified by silica gel chromatography (isohexane/EtOAc), which gave the title compound (16.9 g, 86%).

Step b) 1-cyclobutyl-3-methoxybenzene (Ph6-b)

10% Pd on carbon (2.5 g) was added to a solution of Ph6-a (15.4 g, 86.1 mmol) in ethanol (200 mL) and the mixture was hydrogenated in a Parr at 60 psi. After 18 h, additional 10% Pd on carbon (1.5 g) was added and the mixture was hydrogenated for further 18 hours at 60 psi. The catalyst was filtered of and washed with EtOH and EtOAc. The solution was concentrated under reduced pressure and the crude product was isolated by silica gel chromatography (isohexane/EtOAc), which gave the title compound (14.0 g, 77%).

Step c) 3-cyclobutylphenol (Phenol 6)

A solution of 1M boron tribromide (18.1 g, 72.2 mmol) in DCM was added dropwise at 0° C. to a solution of Ph6-b (10.6 g, 65.6 mmol) in dry DCM (65 mL). The mixture was stirred for 2.5 hours at −5° C., then the reaction was quenched with cooled saturated solution of $NH_4Cl$ and

4-(1-Methylcyclopentyl)phenol (Ph-8)

A solution of 1-methylcyclopentanol (2.00 g, 20.0 mmol) and phenol (2.07 g, 22.0 mmol) in pentane (50 mL) were added dropwise during 30 min to a suspension of fresh AlCl$_3$ (1.33 g, 10 mmol) in pentane (100 mL). The resulting mixture was stirred under N$_2$ at rt for 72 h, then the reaction mixture was poured into water/ice and HCl (12 M, 20 mmol, 1.66 mL). The organic phase was washed with water (50 mL) and brine (50 mL), dried (Na$_2$SO$_4$) filtered and concentrated. The crude was purified by column chromatography on silica (MeOH-DCM), which gave the title compound (426 mg, 12%).

extracted three times with DCM. The organic phase was dried (Na$_2$SO$_4$), filtered and concentrate. The afforded crude product was purified by silica gel chromatography (isohexane/EtOAc), which gave the title compound (9.73 g, 88%).

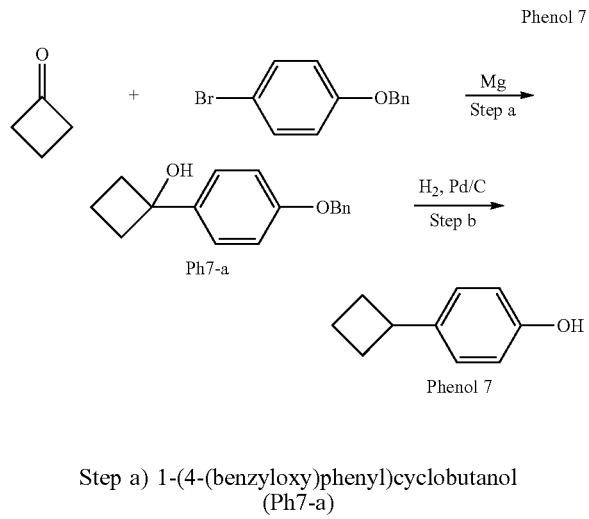

Phenol 7

Step a) 1-(4-(benzyloxy)phenyl)cyclobutanol (Ph7-a)

A solution of 1-(benzyloxy)-4-bromobenzene (2.63 g, 100 mmol) in diethyl ether:THF 1:1 (100 mL) was added dropwise at reflux during ≈1 h to a suspension of magnesium tunings (2.43 g) and a trace iodine in diethyl ether (50 mL). When the addition was completed, the mixture was refluxed for four hours, then cooled to ≈0° C. Dry THF (50 ml) was added followed by slow addition of a solution of cyclobutanone (7.01 g, 100 mmol) in diethyl ether (50 mL) and the mixture was left to attain rt. After stirring for two h, a cool saturated solution of NH$_4$Cl (500 ml) was added and the mixture was stirred for 15 minutes, then extracted twice with EtOAc. The organic phase was washed with brine, dried with sodium sulfate and evaporated under reduced pressure. The product was purified by column chromatography on silica gel, which gave the title compound (12.5 g, 42%).

Step b) 4-cyclobutylphenol (Phenol 7)

Pd 10% on carbon (2.55 g, 21.5 mmol) was added under argon to a solution of Ph7-a (12.4 g, 41.4 mmol) in abs EtOH (110 mL) the and the mixture was hydrogenated at 45 psi at rt for 18 h. The catalyst was filtered of, washed with ethanol and the solution was concentrated. The product was purified by silica gel chromatography (isohexane—EtOAc). Appropriate fractions were pooled and concentrated and the residue crystalized from petrol ether which gave the title compound (3.15 g, 51%).

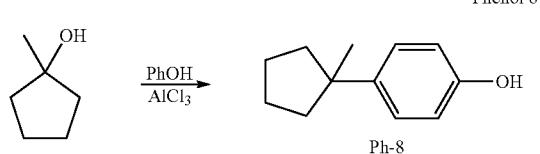

Phenol 8

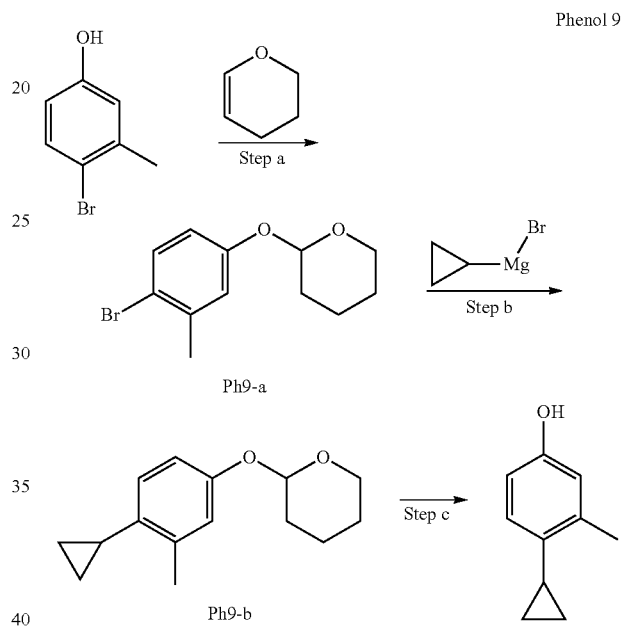

Step a) 2-(4-Bromo-3-methylphenoxy)tetrahydro-2H-pyran (Ph9-a)

pTs (16 mg, 0.086 mmol) was added to a solution of 4-bromo-3-methylphenol (4.0 g, 21.4 mmol) in 3,4-dihydro-2-H-pyran (16 mL, 175 mmol). The reaction mixture was stirred at room temperature for 1 h, then diluted with diethyl ether and washed with 1M NaOH (aq) and water. The organic phase was dried (Na$_2$SO$_4$) filtered and concentrated. The crude was purified by column chromatography on silica (EtOAc/heptane) which gave the title compound (3.32 g, 57%).

Step b) 2-(4-Cyclopropyl-3-methylphenoxy)tetrahydro-2H-pyran (Ph9-b)

Ph9-a (3.12 g, 11.5 mmol), ZnBr$_2$ (2.59 g, 11.5 mmol), tri-tert-butylphosphine tetrafluoroborate (0.2 g, 0.69 mmol) and Pd(OAc)$_2$ (258 mg, 1.15 mmol) were put in a flask and the flask was flushed with N$_2$ a couple of times. THF (10 mL) was added while stirring, followed by dropwise addition of 0.5 M cyclopropylmagnesium bromide in THF (35 mL, 17.4 mmol) during 5 minutes. The mixture was stirred at rt on, then filtered through a Celite plug, eluted with MeOH. The solution was concentrates and the crude was purified by column chromatography on silica (EtOAc/heptane) which gave the title compound (1.69 g, 57%).

Step c) 4-Cyclopropyl-3-methylphenol (Phenol 9)

Ph9-b (1.70 g, 7.30 mmol) was dissolved in MeOH (20 ml) and pTsxH$_2$O (318 mg, 1.67 mmol) was added. The mixture was stirred at 22° C. for 30 minutes, then concentrated. The crude was purified by column chromatography (EtOAc/heptane), which gave the title compound (704 mg, 65%).

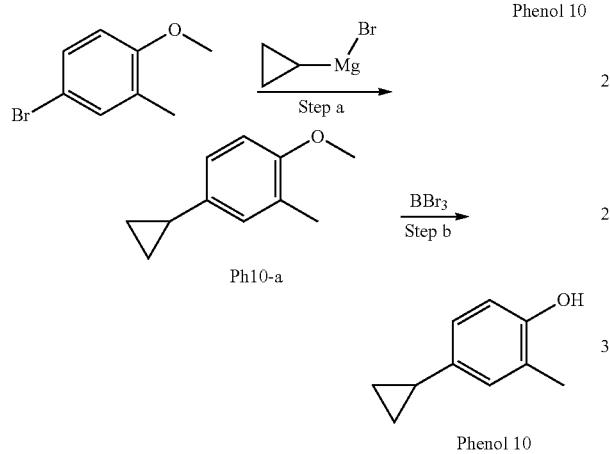

Step a) 4-cyclopropyl-1-methoxy-2-methylbenzene (Ph10-a)

4-Bromo-1-methoxy-2-methylbenzene (4.39 g, 21.9 mmol) was reacted with cyclopropylmagnesium bromide according to the procedure described in Ph9 step b, which gave the title compound (1.54 g, 43%).

Step b) 4-cyclopropyl-2-methylphenol (Phenol 10)

BBr$_3$ (5 mL, 5 mmol) was added under N$_2$ at 0° C. to a solution of Ph10-a (1.54 g, 9.49 mmol) in DCM (7.5 mL). The reaction was stirred for 2 h, then quenched with MeOH (3 mL) and concentrated. The crude was dissolved in EtOAc and washed with brine. The organic phase was dried (Na$_2$SO$_4$), filtered and concentrated. The crude product was purified by column chromatography on silica, which gave the title compound (826 mg, 59%). MS 147.11 [M−H]$^-$.

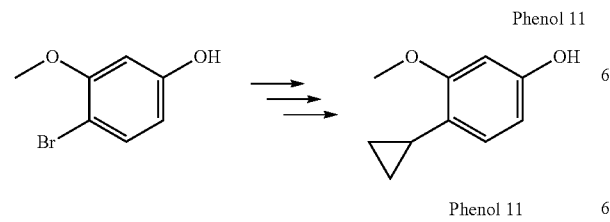

4-cyclopropyl-3-methoxyphenol (Phenol 11)

The title compound was prepared from 4-bromo-3-methoxyphenol (1.11 g, 5.49 mmol) according to the procedure described for the preparation of Phenol 9. Yield 40%.

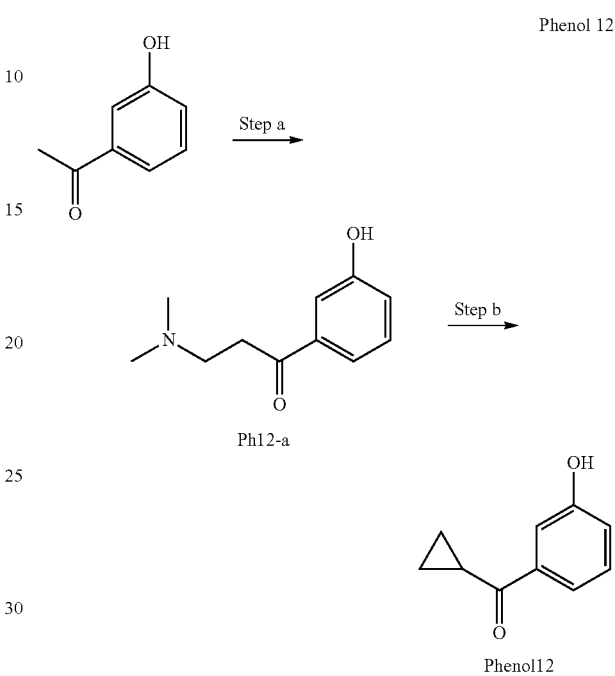

Step a) 3-(dimethylamino)-1-(3-hydroxyphenyl)propan-1-one (Ph12-a)

A few drops of HCl were added to a solution of 3-hydroxy acetophenone (4.08 g, 30 mmol), paraformaldehyde (4.05 g, 45 mmol) and dimethylamine hydrochloride (2.69 g, 33 mmol) in absolute EtOH (100 mL) and the reaction mixture refluxed for 18 h. Additional dimethylamine hydrochloride (0.55 eq., 1.22 g), paraformaldehyde (0.5 eq., 1.35 g) and HCl (0.5 mL) were added and the reaction mixture refluxed for additional 4 h, then cooled to rt. The precipitated white solid was collected and washed with cold EtOH (50 mL) and cold acetone (10 mL) and then freeze dried, which gave the title compound (2.59 g, 38%) that was used in the next step without further purification.

Step b) cyclopropyl(3-hydroxyphenyl)methanone (Phenol 12)

NaH (60% mineral oil dispersion) (1.13 g, 28.2 mmol) was added in portions at rt to a stirred suspension of trimethylsulfoxonium iodide (6.20 g, 28.2 mmol) in DMSO (100 mL). After 1 h, solid Ph12-a (2.59 g, 11.3 mmol) was added in portions under stirring and cooling. The reaction mixture was stirred at rt for 40 h, then poured into cold water (200 mL) and extracted with DCM (3×100 mL). The organic phase was washed with a saturated aqueous solution of NH$_4$Cl (2×100 mL), dried (Na$_2$SO$_4$), filtered and concentrated. The afforded crude was purified by column chromatography on silica (MeOH/DCM) which gave the title compound (883 mg, 48%).

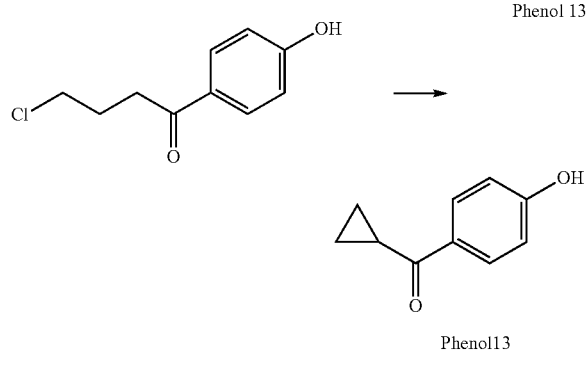

Phenol 13

Phenol13

Step a) cyclopropyl(4-hydroxyphenyl)methanone (Ph13)

p-Hydroxy-γ-chlorobutyrophenone (4.95 g) was added in portions during approximately 30 min to a solution of NaOH (8 mL, aq, 50% w/w), then NaOH (35 mL, aq, 25% w/w) was added followed by p-hydroxy γ-chlorobutyrophenone (4.95 g) in one portion. The temperature was lowered to 140° C. and NaOH (8 g) was added. After 90 min, $H_2O$ (10 ml) was added, and after additional 60 min, the reaction mixture was cooled, diluted with $H_2O$ and neutralized with HOAc (≈27-30 ml) to pH ≈7 The formed precipitate was filtered, washed with $H_2O$ and dried in vacuum. The solids were triturated in $CHCl_3$ (200 ml) at 40° C. during 10 min, then at RT overnight. The slurry was heated to 40° C. during 30 min, then filtered. The filtrate was dried ($MgSO_4$), filtered and concentrated to ≈70 ml. Hexane was added and an oil was formed that eventually became crystals. The slurry was filtered, solids washed with $CHCl_3$/hexane and dried, which gave the title compound (4.15 g, 51%).

Phenol 14

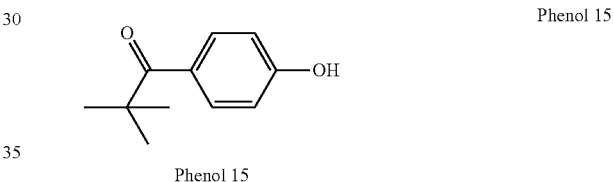

Ph14-a

Phenol 14

Step a) 3-(1-hydroxy-2,2-dimethylpropyl)phenol (Ph14-a)

t.Bu-MgBr (1.5 eq.) was added dropwise during 30 minutes to a cold (−10° C.) mixture of 3-hydroxybenzaldehyde (2.00 g, 16.4 mmol) in diethyl ether (20 mL). During the addition THF (20 mL) was added. The mixture was allowed to reach 23° C. and stirred for 6 hours. More t.Bu-MgBr (0.7 eq.) was added and the mixture was left stirring over night, then cooled and the reaction was quenched with aqueous saturated $NH_4Cl$. to give. EtOAc was added to the mixture followed by addition of 1 M aqueous HCl until a homogeneous mixture was obtained. The phases were separated and the organic phase was washed with brine, dried ($Na_2SO_4$), filtered and concentrated. The afforded crude was purified by column chromatography, which gave the title compound (1.1 g, 37%).

Step b) 1-(3-hydroxyphenyl)-2,2-dimethylpropan-1-one (Ph14)

To an oven dried round bottomed flask was added 3 Å MS and pyridinium chlorochromate (PCC) (1.97 g, 9.15 mmol) followed by dry DCM (5 mL). The mixture was stirred at 20° C. for 5 minutes whereafter a mixture of AA8019 (1.10 g, 6.10 mmol) in DCM (5 mL) was added slowly. After complete oxidation the mixture was filtered through a pad of Celite, washing the pad with diethyl ether. The filtrate was concentrated. The crude was purified by column chromatography which gave the title compound (402 mg, 37%). MS 179.25 [M+H]+.

Phenol 15

Phenol 15

1-(4-Hydroxyphenyl)-2,2-dimethylpropan-1-one (Ph15)

4-hydroxybenzaldehyde (3 g, 24.6 mmol) was reacted according to the procedure described for the preparation of Phenol 14, which gave the title compound (538 mg, 17%).

Amino acid 1

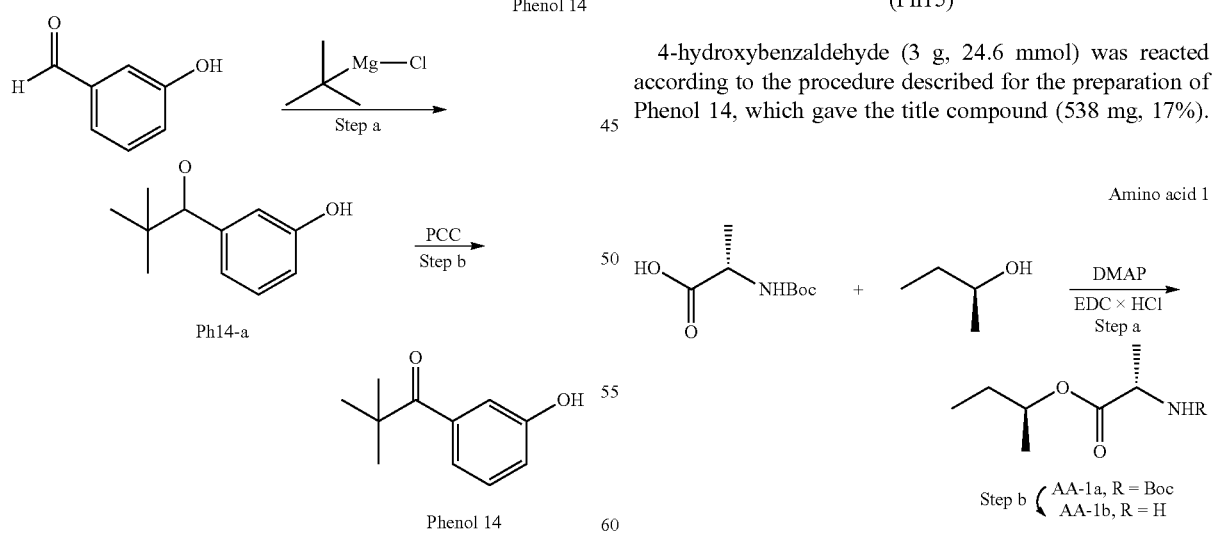

Step a) (S)—(S)-Sec-butyl 2-((tert-butoxycarbonyl)amino)propanoate (AA1-a)

L-Boc-Alanine (2.18 g, 11.5 mmol) was dissolved in dry DCM (40 mL) and the alcohol (R)-butan-2-ol (938 mg, 12.6 mmol) was added. The mixture was cooled to about 5° C. and EDC (3.31 g, 17.2 mmol) was added in one portion followed by portionwise addition of DMAP (140 mg, 1.15 mmol). The mixture was allowed to attain room temperature and stirred overnight, then diluted with ethyl acetate (~300 ml) and the organic phase was washed three times with a saturated solution of sodium hydrogen carbonate and once with brine. The organic phase was dried over sodium sulfate and concentrated under reduced pressure. The product was isolated by silica gel chromatography eluted with isohexane and 10% ethyl acetate, which gave the title compound (2.78 g, 98%).

Step b) (S)—(S)-Sec-butyl 2-aminopropanoate (AA1-b)

A mixture of AA1-a (2.77 g, 11.3 mmol) and p-toluene sulfonic acid mono hydrate (2.15 g, 11.3 mmol) in EtOAc (45 mL) was stirred for 16 h at 65° C., then concentrated under reduced pressure. The afforded residue was crystallised from diethyl ether, which gave the title compound (3.20 g, 89%).

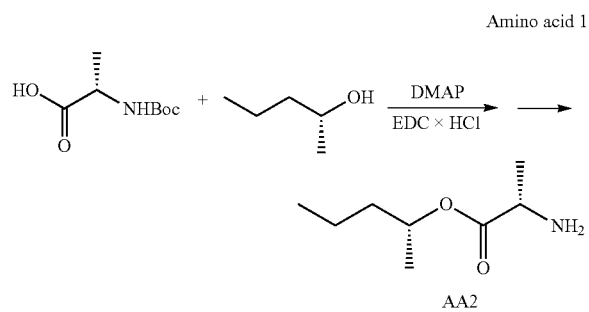

(S)—(R)-Pentan-2-yl 2-aminopropanoate (AA2)

The procedure described for the preparation of AA1 was followed but using (R)-pentan-2-ol instead of (R)-butan-2-ol, which gave the title compound (4.6 g).

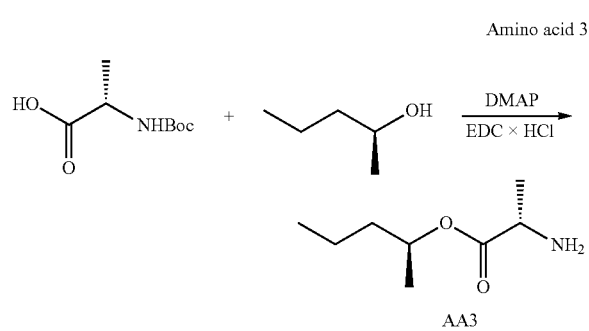

(S)—(S)-Pentan-2-yl 2-aminopropanoate (AA3)

The procedure described for the preparation of AA1 was followed but using (S)-pentan-2-ol instead of (R)-butan-2-ol, which gave the title compound (8.3 g).

The following intermediates were prepared and can be used in the preparation of compounds of the invention:

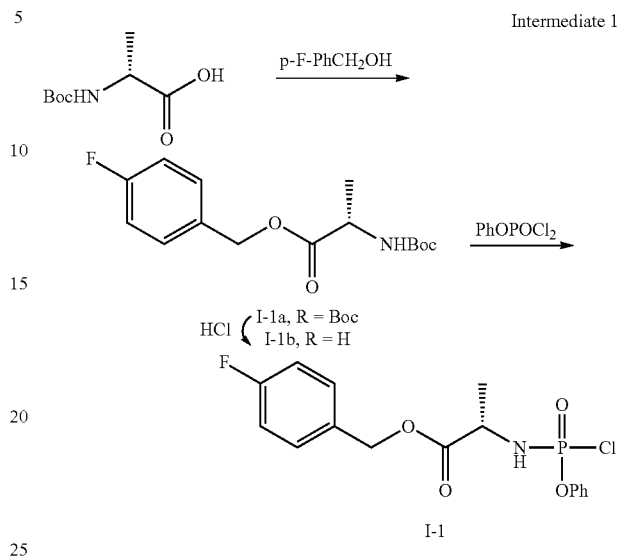

Step a) (R)-4-Fluorobenzyl 2-((tert-butoxycarbonyl)amino)propanoate (I-1a)

Boc-L-AlaOH (19.92 mmol), DMAP (1.99 mmol) and (4-fluorophenyl)methanol (23.9 mmol) were dissolved in $CH_2Cl_2$ (100 mL). To this solution was added triethylamine (23.9 mmol) followed by EDC (23.9 mmol) and the resulting reaction mixture was stirred overnight at room temperature under $N_2$. The reaction mixture was diluted with $CH_2Cl_2$ (100 mL), washed with saturated aqueous solution of $NaHCO_3$ (2×50 mL), saturated aqueous solution of NaCl (2×50 mL), dried ($Na_2SO_4$) and concentrated. The afforded residue was purified by column chromatography on silica gel eluted with n-hexane-EtOAc (95:5 to 60:40) which gave the title compound (4.44 g) as a white waxy solid. MS: 296 $[M-H]^-$.

Step b) (R)-4-fluorobenzyl 2-aminopropanoate (I-1b)

Compound I-1a (14.93 mmol) was dissolved in 4M HCl/dioxane (40 mL) and stirred at room temperature for 30 minutes and evaporated to dryness which gave the hydrochloride salt of the title compound (3.4 g) as a white powder. MS: 198 $[M+H]^+$.

Step c) (2R)-4-fluorobenzyl 2-((chloro(phenoxy)phosphoryl)amino)propanoate (I-1)

$PhOPOCl_2$ (4.28 mmol) was added dropwise at −78° C. to a solution of compound I-5b (4.28 mmol) in $CH_2Cl_2$. followed by dropwise addition of triethylamine (8.56 mmol). The resulting reaction mixture was stirred at −78° C. under Ar and allowed to attain room temperature overnight. The reaction mixture was evaporated on silica gel and purified by chromatography (n-hexane/EtOAc (88:12)-(0:100)). which gave the title compound (769 mg) as a mixture of stereoisomers at the phosphorus atom. $^{31}$P-NMR ($CDCl_3$) δ: 7.85 (s) and 7.54 (s).

Intermediate 2

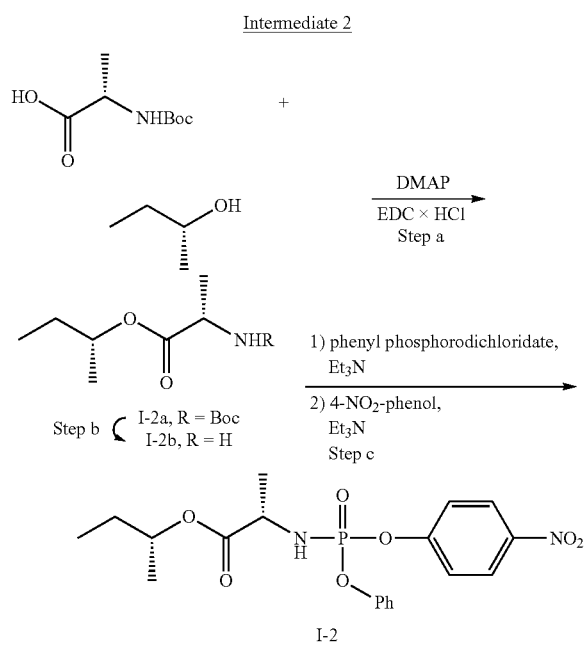

Step a) (S)—(R)-Sec-butyl 2-((tert-butoxycarbonyl)amino)propanoate (I-2a)

L-Boc-Alanine (2.18 g, 11.5 mmol) was dissolved in dry DCM (40 mL) and the alcohol (R)-butan-2-ol (938 mg, 12.6 mmol) was added. The mixture was cooled to about 5° C. and EDC (3.31 g, 17.2 mmol) was added in one portion followed by portionwise addition of DMAP (140 mg, 1.15 mmol). The mixture was allowed to attain room temperature and stirred overnight, then diluted with ethyl acetate (~300 ml) and the organic phase was washed three times with a saturated solution of sodium hydrogen carbonate and once with brine. The organic phase was dried over sodium sulfate and concentrated under reduced pressure. The product was isolated by silica gel chromatography eluted with isohexane and 10% ethyl acetate, which gave the title compound (2.78 g, 98%).

Step b) (S)—(R)-Sec-butyl 2-aminopropanoate (I-2b)

A mixture of I-10a (2.77 g, 11.3 mmol) and p-toluene sulfonic acid mono hydrate (2.15 g, 11.3 mmol) in EtOAc (45 mL) was stirred for 16 h at 65° C., then concentrated under reduced pressure. The afforded residue was crystallised from diethyl ether, which gave the title compound (3.20 g, 89%).

Step c) (2S)—(R)-Sec-butyl 2-(((4-nitrophenoxy)(phenoxy)phosphoryl)amino)propanoate (I-2)

Phenyl dichlorophosphate (1 eq) was added under nitrogen at −30° C. to a solution of Compound I-10b (3.15 g, 9.92 mmol) in DCM (75 ml), followed by dropwise addition of triethylamine (2 eq). The mixture was allowed to attain room temperature and stirred overnight, then cooled to about 5° C. and 4-nitrophenol (1 eq, 15 mmol) was added as a solid followed by dropwise addition of triethylamine (1 eq g, 15 mmol) and the mixture was stirred for 4 hours at room temperature, then concentrated under reduced pressure, diluted with ethyl acetate (40 ml) and ether (40 ml) and left at room temperature overnight. The triethylamine-HCl salt was filtered of and the filtrate was concentrated under reduced pressure. The afforded residue was purified by column chromatography on silica gel eluted with iso-hexane-ethyl acetate, which gave the title compound (4.19 g, 79%) as a mixture of stereoisomers at the phosphorus atom.

The following compounds were prepared as mixtures of stereoisomers at the phosphorus atom according to the procedure described for the preparation of I-2 using the appropriate alcohol:

| I-# | Structure | alcohol |
|---|---|---|
| I-3 | | cyclopropylmethanol |
| I-4 | | cyclopentylmethanol |
| I-5 | | pentan-3-ol |

| I-# | Structure | alcohol |
|---|---|---|
| 1-6 | 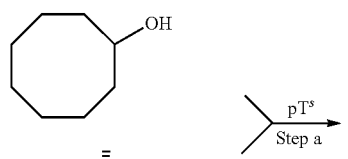 | 2-propylpentan-1-ol |

Intermediate 7

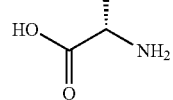

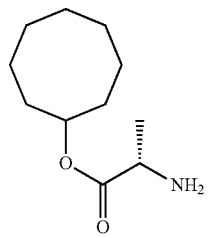

Step a) (S)-cyclooctyl 2-aminopropanoate (I-7a)

p-Toluenesulfonic acid monohydrate (3.6 g, 19.1 mmol) was added to a slurry of L-alanine (1.7 g, 19.1 mmol) and cyclooctanol (25 ml, 191 mmol) in toluene (100 ml). The reaction mixture was heated at reflux temperature for 25 h and water was removed from the reaction using a Dean-Stark trap. The mixture was concentrated under reduced pressure and the residue kept under vacuum over night. To the residue (27 g) was added diethyl ether (100 ml). The white precipitate was collected by filtration, washed with diethyl ether (3×50 ml) and dried under vacuum which gave the title compound (4.84 g, 68%).

Step b) (2S)-cyclooctyl 2-(((4-nitrophenoxy)(phenoxy)phosphoryl)amino)propanoate (I-7)

Compound I-7a was reacted according to the method described for the preparation of I-2 step c, which gave the title compound (4.7 g, 76%) as a mixture of stereoisomers at the phosphorus atom.

Intermediate 8

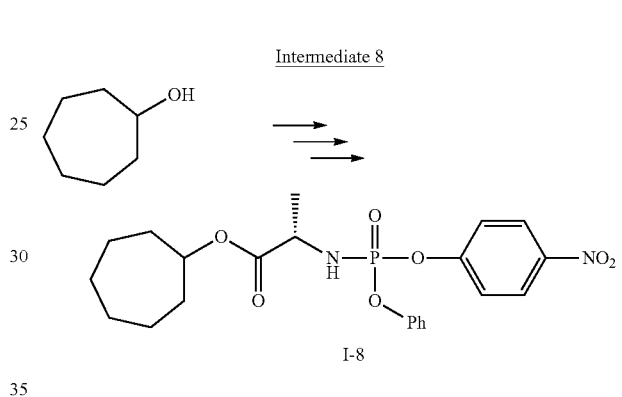

(2S)-cycloheptyl 2-(((4-nitrophenoxy)(phenoxy)phosphoryl)amino)propanoate (I-22)

The procedure described for the preparation of compound I-7 was followed but using cycloheptanol (27 ml, 224 mmol) instead of cyclooctanol, which gave the title compound (5.72 g, 55%) as a mixture of stereoisomers at the phosphorus atom.

Intermediate 9

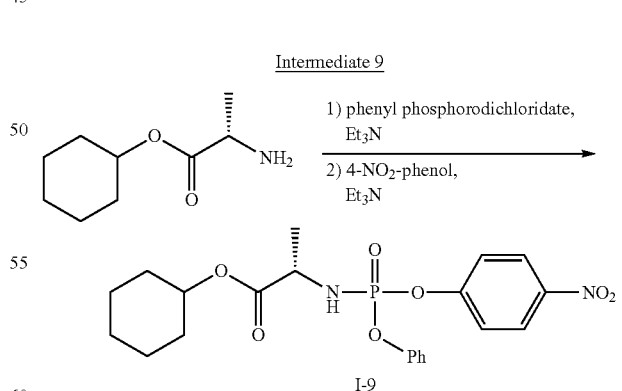

(2S)-Cyclohexyl 2-(((4-nitrophenoxy)(phenoxy)phosphoryl)amino)propanoate (I-23)

The procedure described for the preparation of I-2 step c was followed but using (S)-cyclohexyl 2-aminopropanoate instead of (S)-3,3-dimethylbutyl 2-aminopropanoate, which gave the title compound (10.6 g, 82%) as a mixture of stereoisomers at the phosphorus atom.

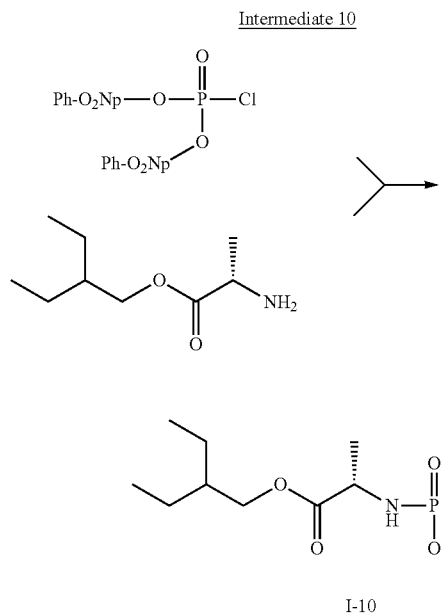

(S)-2-Ethylbutyl 2-((bis(4-nitrophenoxy)phosphoryl)amino)propanoate (I-10)

(S)-2-Ethylbutyl 2-aminopropanoate (5 g, 14.49 mmol) was added to a solution of bis(4-nitrophenyl) phosphorochloridate (6.14 g, 17.1 mmol) in DCM (50 ml), the mixture was cooled in an ice bath and Et$_3$N (4.77 mL, 34.2 mmol) was added drop wise. The cooling was removed after 15 min and the reaction mixture was stirred at 23° C. until complete reaction according to TLC. Diethyl ether was then added, the mixture was filtered and the filtrate was concentrated and purified by column chromatography on silica which gave the title compound (2.05 g, 82%).

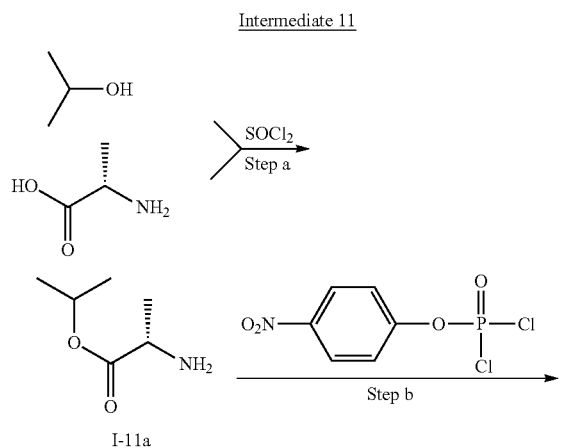

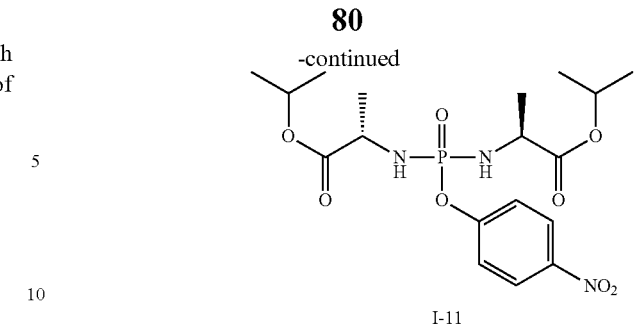

Step a) (S)-isopropyl 2-aminopropanoate (I-11a)

SOCl$_2$ (29 mL, 400 mmol) was added dropwise at 0° C. to a suspension of the HCl salt of L-alanine (17.8 g, 200 mmol) in isopropanol (700 mL). The suspension was stirred at room temperature over night, then concentrated, which gave the title compound (29.2 g, 87%).

Step b) (2S)-Isopropyl 2-(((((S)-1-isopropoxy-1-oxopropan-2-yl)amino)(4-nitrophenoxy)phosphoryl)-amino)propanoate (I-11)

A solution of 4-nitrophenyl dichlorophosphate (1.8 g 7 mmol) in DCM was added dropwise at −60° C. to a solution of the amine I-11a (2.35 g, 14 mmol) and triethylamine (7.7 mL, 56 mmol) in DCM. The reaction mixture was allowed to attain room temperature, stirred over night, concentrated and then diluted with ethyl acetate and ether and left at room temperature overnight. The triethylamine-HCl salt was filtered of, the filtrate was concentrated under reduced pressure and the afforded residue was purified by chromatography on silica gel eluted with iso-hexane-ethyl acetate, which gave the title compound (1.6 g, 50%).

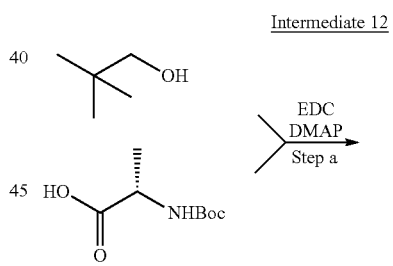

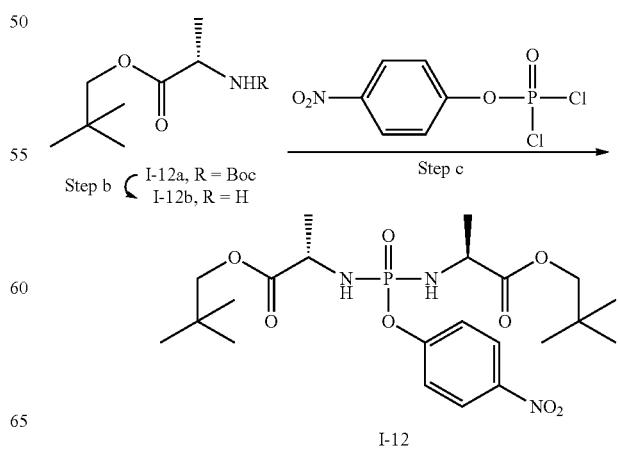

Step a) (S)-Neopentyl 2-((tert-butoxycarbonyl)amino)propanoate (I-12a)

EDAC and DMAP was added in portions at −5° C. to a solution of Boc-alanine (18.9 g, 100 mmol) and neopentylalcohol (13.0 mL, 120 mmol) in DCM (200 mL). The reaction mixture was allowed to attain room temperature and stirred for 72 h. EtOAc (700 mL) was added and the organic phase was washed three times with a saturated solution of NaHCO₃ and once with brine, then concentrated. The afforded residue was purified by column chromatography eluted with hexane-EtOAc 90/10 to 80/20, which gave the title compound (21 g, 81%).

Step b) (S)-Neopentyl 2-aminopropanoate (I-12b)

p-Toluene sulfonic acid (15.6 g, 82.0 mmol) was added at −65° C. to a solution of the Boc protected amine I-12a (21.1 g, 82.0 mmol) in EtOAc (330 mL). The reaction mixture was stirred at −65° C. for 8 h, then left to attain room temperature overnight. The mixture was then filtered and concentrated which gave the title compound (21 g, 78%).

(2S)-Neopentyl 2-(((((S)-1-(neopentyloxy)-1-oxopropan-2-yl)amino)(4-nitrophenoxy)-phosphoryl)amino)propanoate (I-12)

4-Nitrophenol dichlorophosphate was added dropwise during 1 h at −50° C. to a solution of the amine I-12b (3.90 g, 24.5 mmol) in DCM (100 mL). The reaction mixture was allowed to attain room temperature, stirred overnight, concentrated and then diluted with diethyl ether and left at room temperature overnight. The mixture was filtered, the filtrate was concentrated under reduced pressure and the afforded residue was purified by chromatography on silica gel eluted with iso-hexane-ethyl acetate, which gave the title compound (4.8 g, 77%).

Intermediate 13

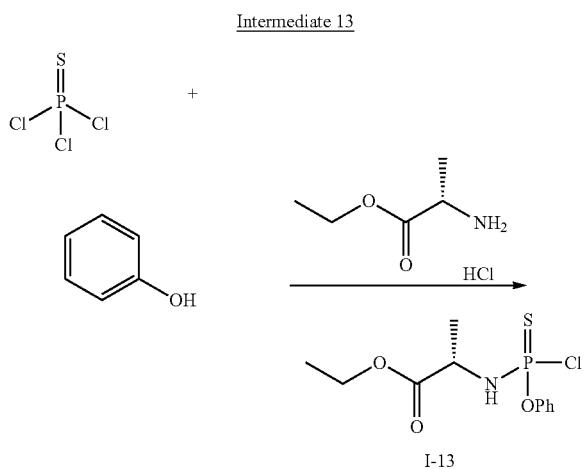

I-13

(2S)-Ethyl 2-((chloro(phenoxy)phosphorothioyl)amino)propanoate (I-13)

Thiophosphoryl chloride (0.27 mL, 2.62 mmol) was added at −35° C. under N₂ to a solution of phenol (247 mg, 2.62 mmol) in a mixture of dry DCM (8.8 mL) and dry THF (4.4 mL). After 5 min, triethylamine (365 μL, 2.62 mmol) was added dropwise and the reaction mixture was stirred at −35° C. for 3 h. Alanine ethyl ester×HCl (403 mg, 2.62 mmol) was added and the reaction mixture was stirred for 5 min at −35° C. whereafter triethylamine (731 μL, 5.24 mmol) was added dropwise. The temperature was slowly allowed to reach rt overnight (17 h). The reaction mixture was diluted with Et₂O, filtered and concentrated under reduced pressure. Flash chromatography (hexane:EtOAc 8:1) of the afforded crude product gave the title compound (659 mg, 82%) as a mixture of stereoisomers at the phosphorus atom as a clear oil. MS 306.18 [M−H]⁻.

Intermediate 14

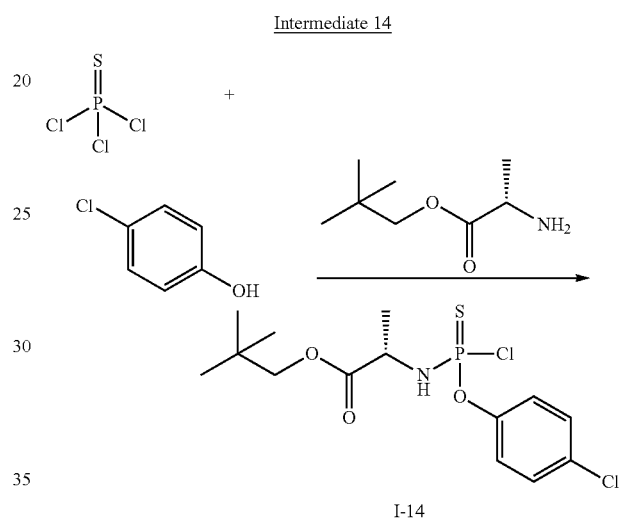

I-14

(2S)-Neopentyl 2-((chloro(4-chlorophenoxy)phosphorothioyl)amino)propanoate (I-14)

4-Chlorophenol (381 μL, 3.87 mmol) was added under nitrogen in one to a solution at −30° C. of thiophosphoryl chloride (400 μL, 3.87 mmol) in DCM followed by dropwise addition of triethylamine (1.62 mL, 11.6 mmol). The reaction was stirred for 2 h while the temperature was allowed to reached +5° C. The pTs salt of (S)-neopentyl 2-aminopropanoate (1.28 g, 3.87 mmol) was added and the mixture was cooled to −30° C. Triethylamine (1.62 L, 11.6 mmol) was added dropwise and the reaction allowed to reach room temperature and stirred over the week-end. The mixture was concentrated onto silica-gel and the residue purified by flash chromatography using hexanes/ethyl acetate: 7/1 which gave the title compound as a mixture of stereoisomers at the phosphorus atom (807 mg, 54%). MS 368.34 [M+H]⁺.

Intermediate 15

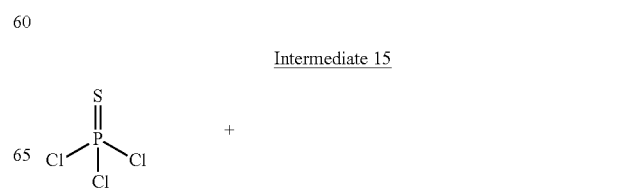

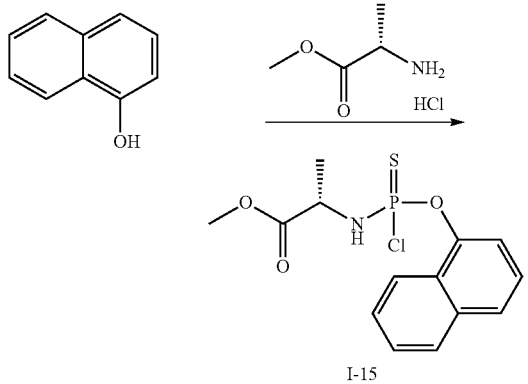

I-15

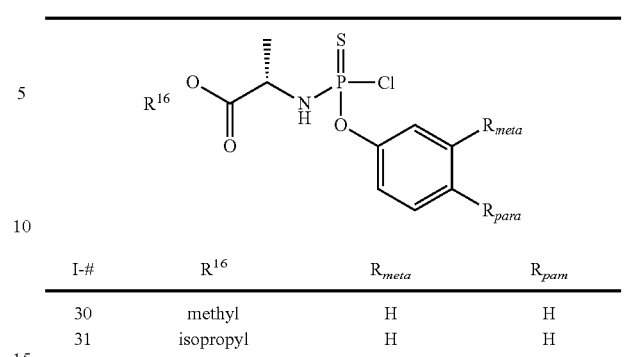

| I-# | $R^{16}$ | $R_{meta}$ | $R_{para}$ |
|---|---|---|---|
| 30 | methyl | H | H |
| 31 | isopropyl | H | H |

(2S)-methyl 2-((chloro(naphthalen-1-yloxy)phosphorothioyl)amino)propanoate (I-15)

Thiophosphoryl chloride (1 eq) was added at −35° C. under $N_2$ to a solution of naphthol (1 eq) in a mixture of dry DCM (10 mL) and dry THF (5 mL). After 5 min, triethylamine (1 eq) was added dropwise and the reaction mixture was stirred at −35° C. for 3 h. (S)-methyl 2-aminopropanoate (1 eq) was added and the reaction mixture was stirred for 5 min at −35° C. whereafter triethylamine (2 eq) was added dropwise. The temperature was slowly allowed to reach rt overnight. The reaction mixture was diluted with $Et_2O$, filtered and concentrated under reduced pressure. Flash chromatography (hexane:EtOAc 8:1) of the afforded crude product gave the title compound as a mixture of stereoisomers at the phosphorus atom. Yield 8.0% MS 564.24 $[M+H]^+$.

The following intermediates were prepared as a mixture of stereoisomers at the phosphorus atom according to the method described for Intermediate 13 using the appropriate phenol and amino acid ester.

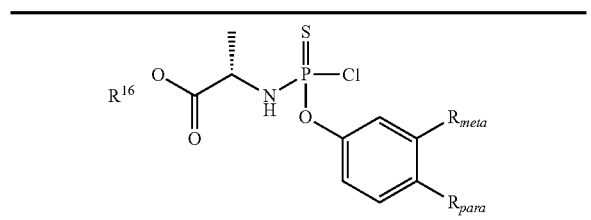

| I-# | $R^{16}$ | $R_{meta}$ | $R_{para}$ |
|---|---|---|---|
| 16 | (2S)-2-ethylbutyl | cyclopropyl | H |
| 17 | ethyl | cyclopropyl | H |
| 18 | (S)-2-pentyl | cyclopropyl | H |
| 19 | isopropyl | H | cyclopropyl |
| 20 | ethyl | H | cyclopropyl |
| 21 | methyl | H | cyclopropyl |
| 22 | isobutyl | H | cyclopropyl |
| 23 | isopropyl | H | H |
| 24 | methyl | methylcyclopropyl | H |
| 25 | isopropyl | cyclopropyl | H |
| 26 | isobutyl | cyclopropyl | H |
| 27 | n-butyl | cyclopropyl | H |
| 28 | methyl | cyclopropyl | H |
| 29 | isopropyl | cyclobutyl | H |

Intermediate 32

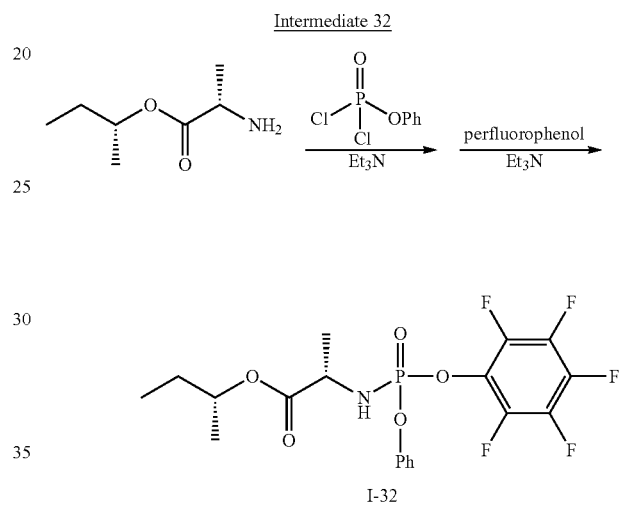

I-32

(2S)—(R)-sec-butyl 2-(((perfluorophenoxy)(phenoxy)phosphoryl)amino)propanoate (I-32)

$Et_3N$ (10.9 mL, 78.1 mmol) was added dropwise at −70° C. under nitrogen during 15 minutes to a stirred solution of the pTs salt of (S)—(R)-sec-butyl 2-aminopropanoate (12.0 g, 37.7 mmol) in DCM (50 mL). To this mixture was added a solution of phenyl dichlorophosphate (5.61 mL, 37.7 mmol) in DCM (50 mL) during 1 h. The reaction mixture was stirred at −70° C. for additional 30 minutes, then allowed to warm to 0° C. during 2 h and stirred for 1 h. A solution of pentafluorophenol (6.94 g, 37.7 mmol) and $Et_3N$ (5.73 mL, 41.1 mmol) in DCM (30 mL) was added to the mixture during 20 minutes. The crude mixture was allowed to stir at 0° C. for 18 h, and was then concentrated. The residue was taken in THF (100 mL), insolubles were filtered off and washed several times with THF. The solvent was evaporated and the residue triturated with tert-butyl methyl ether. Insolubles were filtered off and washed with tert-butyl methyl ether. The combined filtrate was concentrated and the crude solid sonicated with n-hexane/EtOAc (80:20; 100 mL). The solid was filtered, washed with n-hexane/EtOAc (80:20) which gave the pure P-stereoisomer of the title compound as a white solid (2.3 g, 13%).

Intermediate 33

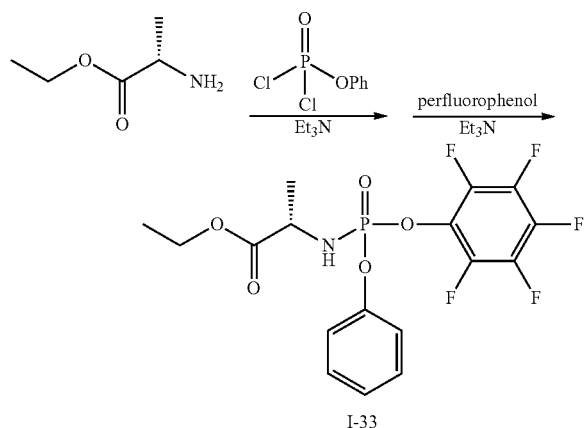

(2S)-ethyl 2-(((perfluorophenoxy)(phenoxy)phosphoryl)amino)propanoate (I-33)

The title compound was prepared as a single stereoisomer at the phosphorus atom according to the method described for 1-32, but starting from the HCl salt of (S)-ethyl 2-aminopropanoate (11.0 g, 71.1 mmol). Yield 8.56 g, 27%.

Intermediate 34

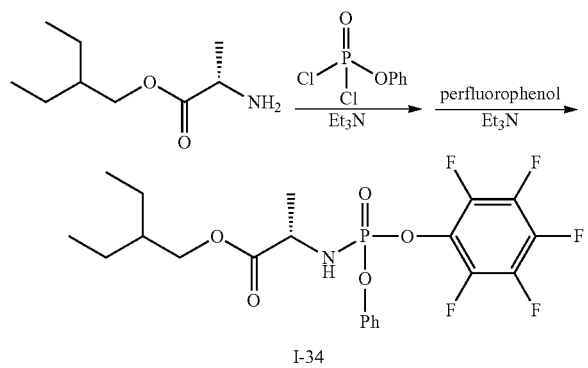

(2S)-2-ethylbutyl 2-(((perfluorophenoxy)(phenoxy)phosphoryl)amino)propanoate (I-34)

The title compound was prepared as a single stereoisomer at the phosphorus atom according to the method described for 1-32, but starting from the pTs salt of (S)-2-ethylbutyl 2-aminopropanoate (18.8 g, 54.4 mmol). Yield 27.0 g, 99%. LC-MS 496.44 [M+H]$^+$.

Intermediate 35

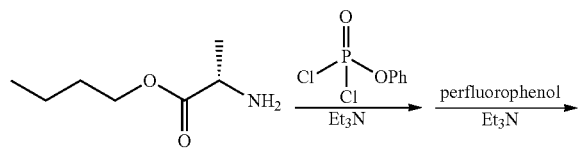

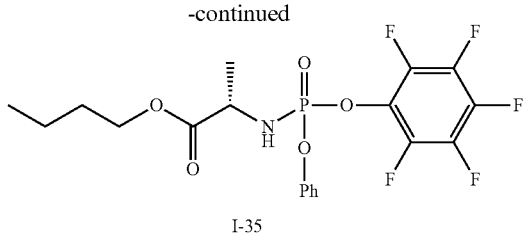

(2S)-butyl 2-(((perfluorophenoxy)(phenoxy)phosphoryl)amino)propanoate (I-35)

Phenyl dichlorophosphate (12.4 mL, 83.1 mmol) was added to a cooled (−20° C.) slurry of (S)-butyl 2-aminopropanoate (26.4 g, 83.1 mmol) in DCM (200 mL). The mixture was stirred for 10 min then Et$_3$N (25.5 mL, 183 mmol) was added dropwise for 15 min. The mixture was stirred at −20° C. for 1 h then at 0° C. for 30 min. The mixture was kept cooled in an ice-bath and pentafluorophenol (15.3 g, 0.08 mol) was added followed by a dropwise addition of Et$_3$N (11.6 mL, 0.08 mol). The mixture was stirred over night and slowly taken to 20° C. Diethyl ether was added and the mixture was filtered through Celite, concentrated and purified by column chromatography on silica gel eluted with petroleum ether/EtOAc (9:1→8:2). Appropriate fractions were pooled, concentrated and crystallized from petroleum ether/EtOAc which gave the pure P-stereoisomer of the title compound as a white solid (2.23 g, 5.8%).

Intermediate 36

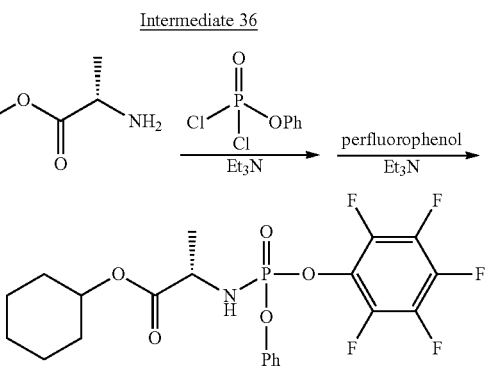

(2S)-Cyclohexyl 2-(((perfluorophenoxy)(phenoxy)phosphoryl)amino)propanoate (I-36)

Phenyl dichlorophosphate (11.1 mL, 74.4 mmol) was added in one portion at −15° C. to a solution of L-alanine cyclohexyl ester (25.5 g, 74.4 mmol) in DCM (250 mL). The resulting mixture was stirred for 10 min, then triethylamine (2.2 eq.) was added over a period of 10 min and the reaction was allowed to proceed cold for 30 min at −15° C. and then at room temperature for 72 h. The reaction was cooled on ice and pentafluorophenol (13.7 g, 74.4 mmol) was added, followed by addition of triethylamine (1 eq.) over 10 min. The reaction was allowed to attain rt and was stirred for 30 min. Insoluble material was filtered off through a pad of Celite and the filter cake was washed with DCM (100 mL).

The solvent was evaporated and the residue dried in vacuum, then taken into EtOAc (200 mL) and stirred for 20 min. Insoluble material was filtered off through a pad of Celite and the cake washed with EtOAc (75 mL) and the solution was left at 5° C. overnight. The formed crystals were dissolved in EtOAc and the solution was washed with 2 M NaOH (×1), 2 M HCl (×1) dried (Na$_2$SO$_4$) and concentrated, which gave (2.37 g, 6%) almost pure diastereoisomer of the title compound (de=~90%).

Intermediate 37

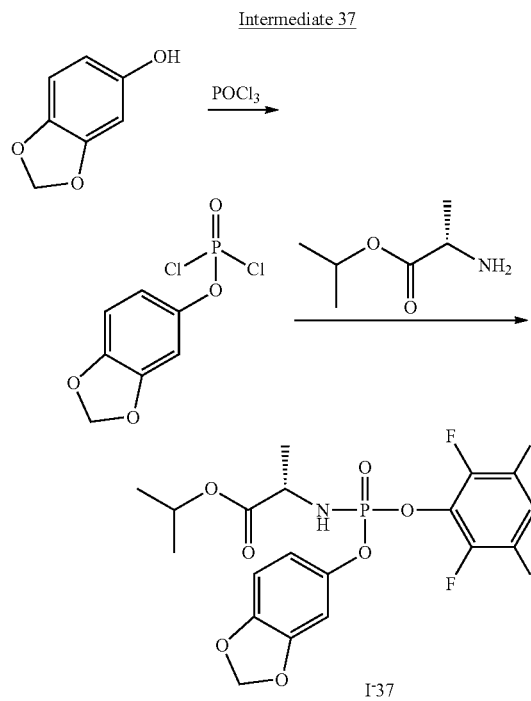

(2S)-Isopropyl 2-(((benzo[d][1,3]dioxol-5-yloxy) (perfluorophenoxy)phosphoryl)amino)propanoate (I-37)

POCl$_3$ (1.79 ml, 19.2 mmol) was added under N$_2$ at −78° C. to a solution of sesamol (2.65 g, 19.2 mmol) in DCM (60 mL), followed by drop wise addition of Et$_3$N (2.67 ml, 19.2 mmol). The mixture was stirred for 4 h at −20 to −30° C. The mixture was cooled to −78° C. and a solution of (S)-isopropyl 2-aminopropanoate (3.22 g, 19.2 mmol) in DCM (10 mL) was added dropwise, followed by addition of Et$_3$N (5.62 ml, 40.3 mmol) over 15 min. The reaction mixture was allowed to attain rt and stirred over night. The temperature of the reaction mixture was then lowered to 0° C. and pentafluorophenol (3.53 g, 19.2 mmol) was added in one portion followed by dropwise addition of Et$_3$N (2.67 ml, 19.2 mmol). The obtained slurry was stirred at 0° C. When the reaction was completed as judged by LC-MS, the mixture was filtered and the solid was washed with cold DCM. The filtrate was concentrated and redissolved in tert-butyl ether, filtered again and then concentrated. EtOAc: Hexane 20:80 was added and the obtained slurry heated gently until a clear solution was obtained. The solution allowed to reach rt and then put at −20° C. After 1 hour crystals was formed, filtered off, washed several times with hexane and then dried under vacuum, yield: 1.8 g. The mother liquid was concentrated and the crystals formed filtered off and dried under vacuum, yield: 5.5 g. Total yield: 7.3 g, 69% of the title compound as a single stereoisomer at the phosphorus atom. MS ES+ 498.06 [M+H]$^+$.

The following intermediates were prepared as single stereoisomers at the phosphorus atom according to the method described for Intermediate 37 using the appropriate phenol and amino acid ester.

[Structure of I-#]

| I-# | R$_{ortho}$ | R$_{meta}$ | R$_{para}$ | Yield | MS |
| --- | --- | --- | --- | --- | --- |
| 38 | methoxy | H | H | 62% | na |
| 39 | H | H | methoxy | 63% | na |
| 40[1] | H | cyclopropyl | H | 27% | 494.2 [M + H]$^+$ |
| 43 | H | cyclobutyl | H | 20% | 508.0 [M + H]$^+$ |
| 44[1] | H | 1-methylcyclopropyl | H | 11% | 508.0 [M + H]$^+$ |
| 45[1] | H | H | 1-methylcyclopropyl | 41% | 506.5 [M + H]$^−$ |

[1] Pentafluorophenol was added at −78° C. not at 0° C. as in I-37

Intermediate 41

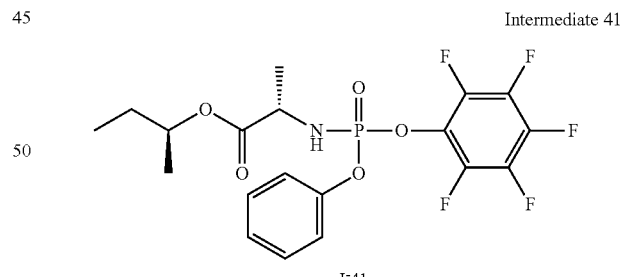

(2S)—(S)-Sec-butyl 2-(((perfluorophenoxy)(phenoxy)phosphoryl)amino)propanoate (I-41)

The title compound was prepared as a single stereoisomer at the phosphorus atom according to the method described for I-32, but starting from (S)—(S)-sec-butyl 2-aminopropanoate (12.0 g, 37.8 mmol) instead of (S)—(R)-sec-butyl 2-aminopropanoate. Yield: 3.33 g, 19%.

Intermediate 42

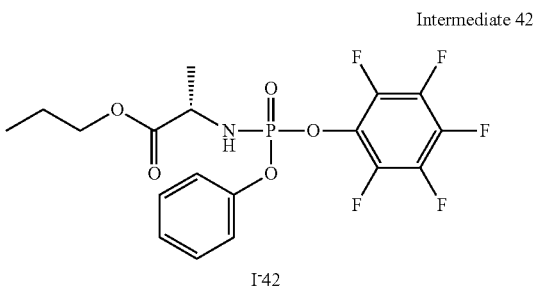 [SMILES: CCCOC(=O)[C@H](C)NP(=O)(Oc1ccccc1)Oc1c(F)c(F)c(F)c(F)c1F]

I-42

(2S)-Propyl 2-(((perfluorophenoxy)(phenoxy)phosphoryl)amino)propanoate (I-42)

The title compound was prepared as a single stereoisomer at the phosphorus atom according to the method described for I-35, but starting from the HCl salt of (S)-propyl 2-aminopropanoate (5.62 g, 33.53 mmol)) instead of the pTs salt (S)—(R)-sec-butyl 2-aminopropanoate. The product was recrystallized from isopropyl ether. Yield: 5.8 g (38%). LC-MS ES+ 454.1 [M+H]$^+$.

Intermediate 46

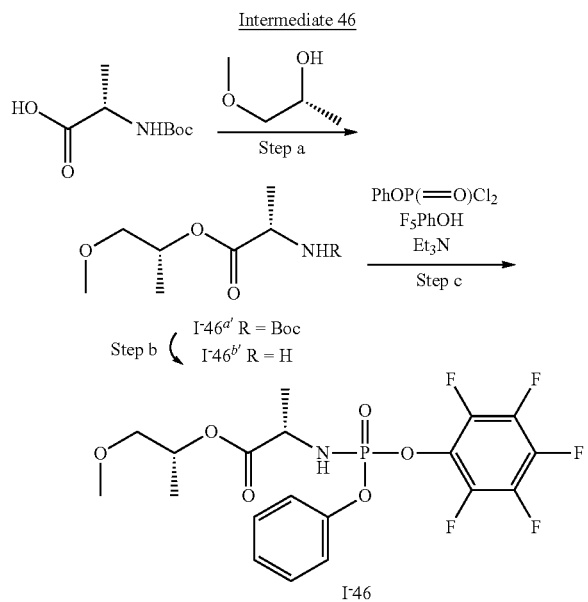

I-46

Step a) (S)—(R)-1-Methoxypropan-2-yl 2-((tert-butoxycarbonyl)amino)propanoate (I-46a)

EDC (6.08 g, 0.03 mol) and 4-(dimethylamino)pyridine (0.48 g, 0.004 mol) were added to a solution of Boc-L-alanine (5 g, 0.03 mol) and (R)-(−)-1-methoxy-2-propanol (2.59 ml, 0.03 mol) at 0° C. The reaction mixture was left stirring on a melting ice-water bath and was then stirred at room temperature for 72 h.

The reaction mixture was concentrated to ~½ the volume, diluted with ethyl acetate (400 mL) and washed with saturated aqueous NH$_4$Cl (200 ml), 10% aqueous citric acid (50 mL) and saturated aqueous NaHCO$_3$ (200 mL). The organic layer was dried (Na$_2$SO$_4$), filtered and concentrated.

The crude product was purified by silica gel column chromatography (Biotage SNAP ultra 100 g, gradient of 5-30% ethyl acetate in heptane) which gave the title compound as a clear oil (5.90 g, 85%).

Step b) (S)—(R)-1-methoxypropan-2-yl 2-aminopropanoate (I-46b)

A solution of I-46a (5.88 g) in 4M HCl in dioxane (50 mL) was stirred for 90 min, then concentrated and the residue freeze dried from dioxane (25 mL), which gave the title compound as the hydrochloride (5.19 g, 99%).

Step c) (2S)—(R)-1-Methoxypropan-2-yl 2-(((perfluorophenoxy)(phenoxy)phosphoryl)amino)-propanoate (I-46)

Triethylamine (9.25 mL, 66.4 mmol) was added dropwise to a cooled (0° C.) solution of (S)—(R)-1-methoxypropan-2-yl 2-aminopropanoate hydrochloride (5.18 g, 22.1 mmol) in DCM (35 mL). The mixture was cooled to −78° C. and a solution of phenyl dichlorophosphate (3.29 mL, 22.1 mmol) in DCM (20 mL) was added. The mixture was stirred for 10 min then Et$_3$N (25.5 mL, 183 mmol) was added dropwise for 15 min. The mixture was stirred at −78° C. for 5 min then at 0° C. for 2 h. Pentafluorophenol (4.07 g, 22.1 mmol) and Et$_3$N (3.39 mL, 23.3 mmol) in DCM (20 mL) was added dropwise then the reaction mixture was slowly left to attain room temperature and was stirred over night. The mixture was concentrated and THF (50 mL) was added. Solids filtered off and washed with THF (3×25 mL) The filtrate was concentrated and the residue dissolved in tert-butyl methyl ether (50 ml) with help of sonification. Heptane (50 ml) was added and the product precipitated from the solution upon standing at room temperature for 1 h. More heptane was added (50 ml) and the solid was removed by filtration. The precipitate was washed with tert-butyl methyl ether/heptane 1:2 (50 ml) and heptane (50 ml). The precipitate was dried under vacuum which gave the title compound as pure isomer according to NMR. (4.32 g, 40%). LC-MS ES+ 484.34 [M+H]$^+$.

Intermediate 47

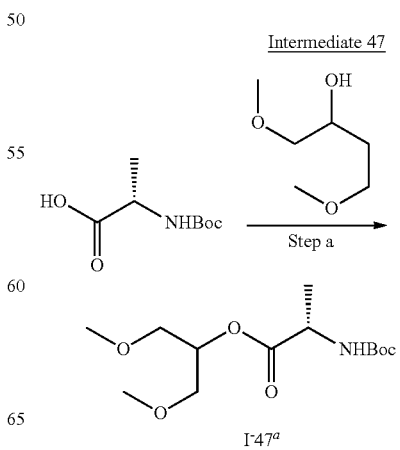

I-47$^a$

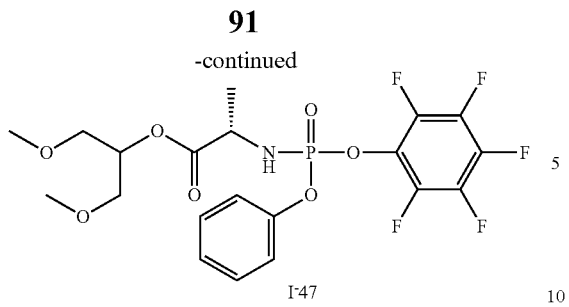

I-47

Step a) (S)-1,3-Dimethoxypropan-2-yl 2-((tert-butoxycarbonyl)amino)propanoate (I-47-a)

EDC (2.79 g, 14.5 mmol), crystalline 4-(dimethylamino)pyridine (229 mg, 1.88 mmol) and Et$_3$N (5.27 ml, 37.8 mmol) were added to a solution of Boc-L-alanine (2.42 g, 12.8 mmol) and 1,3-dimethoxypropan-2-ol (1.52 g, 12.6 mmol). The reaction mixture was stirred at room temperature for 72 h, then diluted with EtOAc and washed with, NaHCO$_3$ (aq, ×2), 0.1M HCl (aq, ×2), dried (Na$_2$SO$_4$) and concentrated. The afforded crude product was used as is in the next step.

Step b) (2S)-1,3-Dimethoxypropan-2-yl 2-(((perfluorophenoxy)(phenoxy)phosphoryl)-amino)propanoate (I-47)

I-47a (3. g, 10.8 mmol) was stirred in 4M HCl in THF (15 mL, 60 mmol) at 22° C. for 2 h then concentrated and co-evaporated twice with toluene. The afforded oil that was dissolved in DCM (40 ml) and phenyl dichlorophosphate (1.62 mL, 10.8 mmol) was added. The mixture was cooled on an ice bath and after 15 min Et$_3$N (3.32 mL, 23.8 mmol) was added slowly. The mixture was stirred at 4° C. for 18 h, then slowly taken to 22° C. The mixture was again cooled to 0° C. and pentafluorophenol (2.01 g, 10.9 mmol) was added followed by a dropwise addition of Et$_3$N (1.51 mL, 10.8 mmol). The mixture was stirred at 0° C. for 1 h then at 22° C. for 5 h. The mixture was filtered, and the solids washed with EtOAc ×3 (total 150 mL). The combined organic phases were washed with NaHCO$_3$ (aq, ×2) and brine, then dried (Na$_2$SO$_4$). The solution was put through a short silica column eluted with p.ether/EtOAc (8:2) appropriate fractions were collected and concentrated and the afforded oil dissolved in diisopropyl ether and treated with heptane to give a light cloudy solution that solidified on standing. The mixture was left at 4° C. for 72 h, then the solids were collected by filtration which gave the title compound as a single stereoisomer at the phosphorus atom (333 mg, 6%). LC ES+ 514.0 [M+H]$^+$.

Intermediate 48

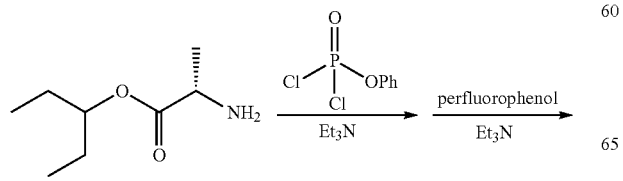

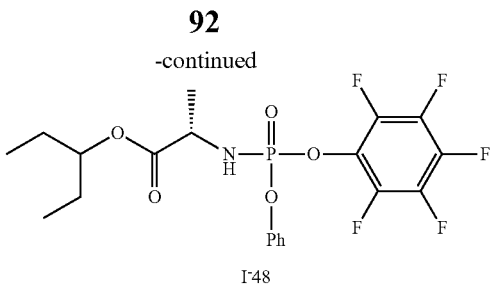

I-48

(2S)-Pentan-3-yl 2-(((perfluorophenoxy)(phenoxy)phosphoryl)amino)propanoate (I-48)

The title compound was prepared as a single stereoisomer at the phosphorus atom according to the method described for I-32, but starting from the HCl salt of (S)-pentan-3-yl 2-aminopropanoate (3.25 g, 16.6 mmol)) instead of the pTs salt (S)—(R)-sec-butyl 2-aminopropanoate. Yield: 8.0 g (18%). LC-MS ES+ 482.4 [M+H]$^+$.

Intermediate 49

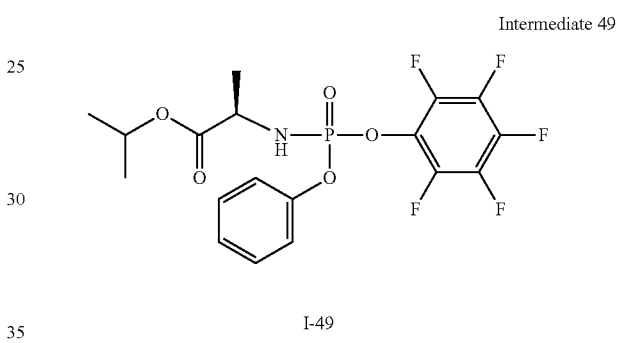

I-49

The title compound was prepared as a single stereoisomer at the phosphorus atom according to the procedure described in WO 2014/078427.

Intermediate 50

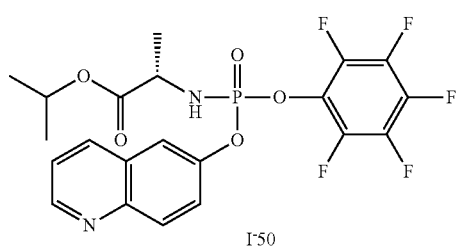

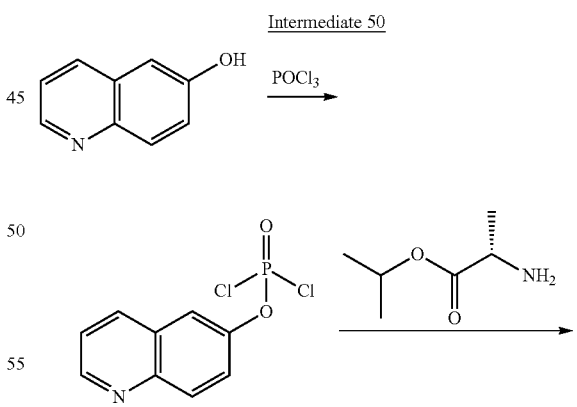

I-50

(2S)-Isopropyl 2-(((perfluorophenoxy)(quinolin-6-yloxy)phosphoryl)amino)propanoate (I-50)

Phosphorus oxychloride (1.5 mL, 16.4 mmol) was added to DCM (40 ml) and the mixture was cooled in a dry-ice/EtOH bath. 6-Hydroxyquinoline (2.38 g, 16.4 mmol) was added followed by drop wise addition of Et₃N (2.28 mL, 16.4 mmol) in DCM (5 mL). The mixture was stirred with cooling for 3 h then isopropyl alanine (2.75 g, 16.4 mmol) was added followed by drop wise addition of Et₃N (4.57 ml, 32.8 mmol). The mixture was stirred with cooling for 5 h. Pentafluorophenol (3.02 g, 16.4 mmol) was added followed by Et₃N (2.28 ml, 16.4 mmol) and the mixture was stirred for 72 h. The mixture was diluted with EtOAc (200 mL) and washed with 0.1 M HCl (aq) ×2, dried (Na₂SO₄) and concentrated. The residue was purified by silica using petroleum ether/EtOAc (1:1) to give a beige solution that solidified in EtOAc/p-Ether. The solid was collected by filtration which gave the title compound as a single stereoisomer at the phosphorus atom (787 mg, 9.5%).

Intermediate 51

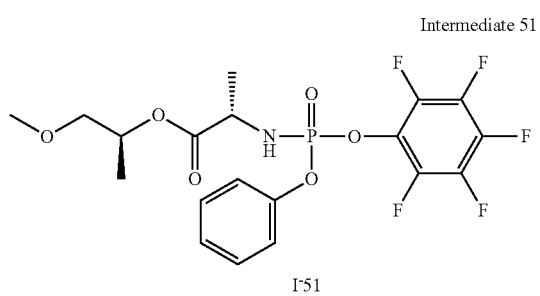 [SMILES: COC[C@H](C)OC(=O)[C@H](C)NP(=O)(Oc1ccccc1)Oc1c(F)c(F)c(F)c(F)c1F]

I-51

(2S)—(S)-1-Methoxypropan-2-yl 2-(((perfluorophenoxy)(phenoxy)phosphoryl)amino)propanoate (I-51)

The title compound was prepared as a single isomer at the phosphorus atom according to the method described for I-46, but starting from (S)-(+)-1-methoxy-2-propanol (0.87 mL, 8.89 mmol) instead of (R)-(−)-1-methoxy-2-propanol. Yield: 604 mg, 14%. LC-MS (ES−) 481.5 [M−H]⁻.

Intermediate 52

(S)-Isopropyl 2-(((S)-(perfluorophenoxy)(phenoxy)phosphoryl)amino)propanoate (I-52)

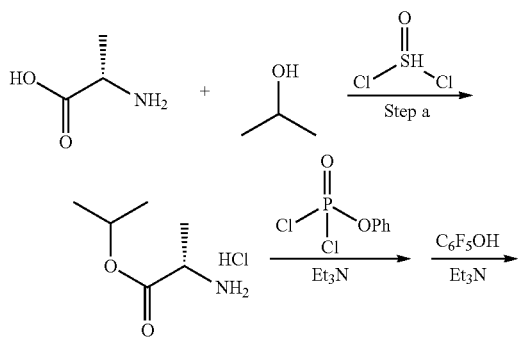

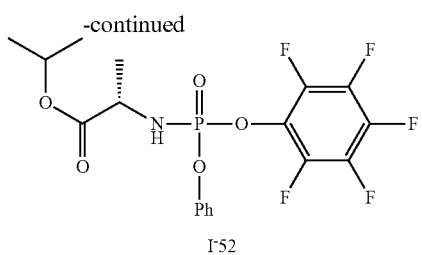

I-52

Step a) L-Alanine isopropylester hydrochloride

Thionylchloride (80.2 g, 0.674 mol, 1.5 eq) was added with cooling to 2-propanol (400 mL) at −7 to 0° C. over a period of 30 minutes, followed by addition of L-alanine (40.0 g, 0.449 mol) at 0° C. A flow indicator and a scrubber with a mixture of 27.65% sodium hydroxide (228 g) and water (225 g) were attached to the outlet. The reaction mixture was stirred at 67° C. for two hours, then at 70° C. for one hour and at 20-25° C. over night. The reaction mixture was distilled at 47-50° C. under reduced pressure (250-50 mBar) from a 60° C. bath. When the distillation became very slow, toluene (100 mL) was added to the residual oil, and the distillation at 48-51° C. under reduced pressure (150-50 mBar) from a 60° C. bath was continued until it became very slow. t-butylmethylether (tBME)(400 mL) was added to the residual oil, and the two-phase system ws seeded under efficient stirring at 34-35° C. When crystallization was observed the mixture was cooled to 23° C. over a period of one hour, and the precipitate isolated by filtration. The filter cake was washed with tBME (100 mL) and dried to constant weight under reduced pressure without heating, which gave the title compound (67.7 g, 90%) as white solids.

Step b) (S)-Isopropyl 2-(((S)-(perfluorophenoxy)(phenoxy)phosphoryl)amino)propanoate (I-52)

Phenyl dichlorophosphate (62.88 g, 0.298 mol, 1.0 eq) was added under nitrogen to a solution of L-alanine isopropylester hydrochloride (50.0 g, 0.298 mol) in DCM (310 mL) at 0° C.—the addition was completed by wash with DCM (39 mL). The mixture was cooled and triethylamine (63.35 g, 0.626 mol, 2.1 eq) was added over a period of 70 minutes with cooling keeping the temperature not higher than −14° C., the addition was completed by wash with DCM (39 mL). The mixture was stirred for one hour at −15 to −20° C., then heated to −8° C. and a solution of pentafluorophenol (60.38 g, 0.328 mol, 1.1 eq) and triethylamine (33.19 g, 0.328 mol, 1.1 eq) in DCM (78 mL) was added over a period of 42 minutes with cooling keeping the temperature not higher than 0° C.—the addition was completed by wash with DCM (39 mL). The mixture was stirred for one hour at 0° C. and then over night at +5° C. The formed precipitate was removed by filtration, and the filter cake washed with DCM (95 mL). The combined filtrates were washed at 5° C. with water (2×190 mL). The organic phase was distilled at 32-38° C. at reduced pressure (650-600 mBar), and distillation was continued until a residual volume of approx. 170 mL partly crystallized mass was obtained. Ethyl acetate (385 mL) was added, and the resulting clear solution was distilled at 43-45° C. under reduced pressure (300-250 mBar). Distillation was continued until a residual volume of approx. 345 mL was obtained. The clear solution was cooled to 36° C., and crystallization is induced by addition of seed crystals of (S)-isopropyl 2-(((S)-(perfluorophenoxy)(phenoxy)phosphoryl)amino)propanoate (20 mg) prepared as described in J. Org. Chem., 2011, 76, 8311-8319. The mixture was cooled to 27° C. over a period of one hour, then n-heptane (770 mL) was added over a period of 47 minutes, and the mixture was stirred for an additional period of 37 minutes. Triethylamine (6.03 g, 0.2 eq) was added, and the mixture was stirred at 23-25° C. over night. The precipitate was isolated by filtration. The filter cake was washed with ethyl acetate:n-heptane (1:9, 80 mL) and dried to constant under reduced pressure (below 0.1 mBar) without heating, which gave the title compound (75.64 g, 56%) as a single stereoisomer at the phosphorus atom as a white crystalline material.

$^1$H NMR (CDCl$_3$, 300 MHz) δ 7.38-7.32 (m, 2H), 7.27-7.24 (m, 2H), 7.23-7.19 (m, 1H), 5.10-4.98 (m, 1H), 4.20-4.08 (m, 1H), 4.03-3.96 (m, 1H), 1.46 (dd, 7.2, 0.6 Hz, 3H), 1.26-1.23 (2×d, 6H);

$^{13}$CNMR (CDCl$_3$, 100 MHz) δ 172.7 (d, J=8.8 Hz), 150.4 (d, J=7.1 Hz), 143.4-143.0 (m), 141.0-140.2 (m), 140.0-139.8 (m), 137.6-137.2 (m), 136.8-136.2 (m), 130.0 (d, J=0.82 Hz), 125.8 (d, J=1.4 Hz), 120.3 (d, J=5.0 Hz), 69.8, 50.6, (d, J=1.9 Hz), 21.8 (d, J=1.9 Hz), 21.2 (d, J=4.4 Hz);

The crystallization properties and NMR spectral data of the title compound were in agreement with published data (J. Org. Chem., 2011, 76, 8311-8319), thus confirming the S stereochemistry of the phosphorus atom of the title compound.

Example 1

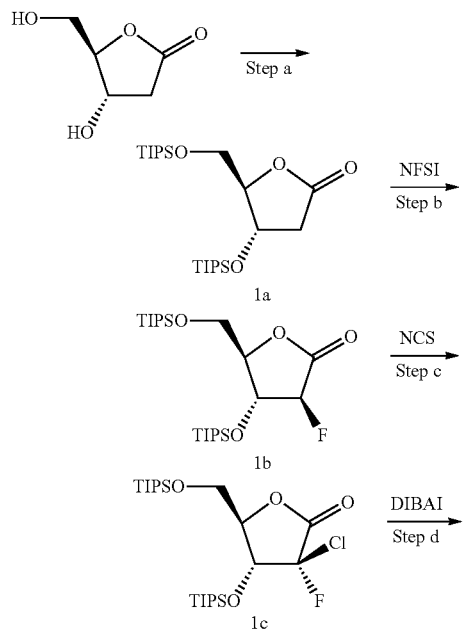

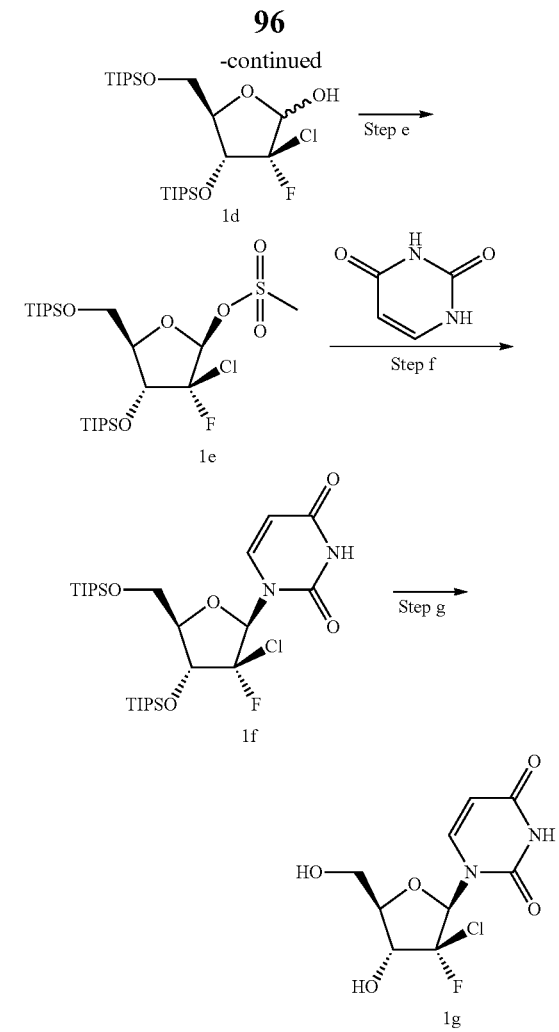

Step a) (4S,5R)-4-((triisopropylsilyl)oxy)-5-(((triisopropylsilyl)oxy)methyl)dihydrofuran-2(3H)-one (1a)

TIPS-chloride (16.4 g, 85 mmol) was added drop wise to an ice cooled stirred solution of (4S,5R)-4-hydroxy-5-(hydroxymethyl)dihydrofuran-2(3H)-one (3.30 g, 25.0 mmol) and imidazole (10.2 g, 150 mmol) in DMF (35 mL). The mixture was stirred for 1 h at 0° C. then at rt for 40 h. The reaction was quenched with water and the mixture extracted three times with EtOAc. The organic phase was dried (Na$_2$SO$_4$), filtered and concentrated, and the product was isolated by silica gel column chromatography eluted with a gradient of isohexane and 0 to 10% EtOAc. Mixed fractions were purified again by silica gel column chromatography eluted with toluene, which gave the title compound (11.1 g, 94%).

Step b) (3S,4R,5R)-3-fluoro-4-((triisopropylsilyl)oxy)-5-(((triisopropylsilyl)oxy)methyl)-dihydrofuran-2(3H)-one (1b)

A 1M solution of lithium bis(trimethylsilyl) amide (2.18 g, 13.0 mmol) was added dropwise during 10 min to a solution at −70° C. of 1a (4.45 g, 10.0 mmol) and NFSI (4.73 g, 15.0 mmol) in dry THF (50 mL). The mixture was stirred for 90 min at −70° C., then added to a saturated solution of ammonium chloride and cracked ice. The mixture was extracted three times with EtOAc, the organic phase was dried (Na₂SO₄), filtered and concentrated, and the product was isolated by silica gel chromatography eluted with a gradient of isohexane and 0 to 5% EtOAc. Yield 4.63 g, 67%.

Step c) (3S,4R,5R)-3-chloro-3-fluoro-4-((triisopropylsilyl)oxy)-5-(((triisopropylsilyl)oxy)methyl)-dihydrofuran-2(3H)-one (1c)

A 1M solution of lithium bis(trimethylsilyl) amide was added drop wise during 10 min to a solution at −70° C. of 1b (3.08 g, 6.65 mmol) and N-chlorosuccinimide (1.07 g, 7.99 mmol) in dry THF (25 mL). The mixture was stirred for 90 min at −70° C., then added to a saturated solution of ammonium chloride and cracked ice. The mixture was extracted three times with EtOAc, the organic phase was dried (Na₂SO₄), filtered and concentrated, and the product was isolated by silica gel chromatography eluted with a gradient of isohexane and 0 to 5% EtOAc. Yield 2.40 g, 73%.

Step d) (3S,4R,5R)-3-chloro-3-fluoro-4-((triisopropylsilyl)oxy)-5-(((triisopropylsilyl)oxy)methyl)-tetrahydrofuran-2-ol (1d)

A 1M solution of MAL (2.23 g, 15.7 mmol) in DCM was added dropwise under argon to solution at −70° C. of 1c (5.20 g, 10.5 mmol) in dry toluene (50 mL). The mixture was stirred for 2 h at −70° C., then the temperature was raised to −30° C. and the reaction was quenched with 2 mL MeOH and then added to a mixture of Rochelle salt and crashed ice. The mixture was stirred for 30 minutes and then extracted three times with EtOAc. The organic phase was dried (Na₂SO₄), filtered and concentrated under reduced pressure. The product was isolated by silica gel column chromatography eluted with a gradient of isohexane and 0 to 10% EtOAc. Yield 5.22 g, 85%.

Step e) (2S,3S,4R,5R)-3-chloro-3-fluoro-4-((triisopropylsilyl)oxy)-5-(((triisopropylsilyl)oxy)methyl) tetrahydrofuran-2-yl methanesulfonate (1e)

Mesyl chloride (688 mg, 6.00 mmol) was slowly added to a cooled solution of 1d (2.00 g, 4.01 mmol) and TEA (608 mg, 6.00 mmol) in DCM (20 mL). The mixture was stirred for three hours at RT, then diluted with EtOAc (80 mL), washed with saturated NaHCO₃ (aq), HCl, water and with brine. The organic phase was dried (Na₂SO₄), filtered and concentrated. The crude product was dried in vacuo and then was used in the next step without further purification.

Step f) 1-((2R,3S,4R,5R)-3-chloro-3-fluoro-4-((triisopropylsilyl)oxy)-5-(((triisopropylsilyl)oxy)methyl)tetrahydrofuran-2-yl)pyrimidine-2,4(1H,3H)-dione (1f)

A suspension of uracil (699 mg, 6.24 mmol) and ammonium sulfate (25.8 mg, 0.195 mmol) in hexamethyldisilazane (HDMS) (40 mL) was refluxed overnight. The solvent was removed in vacuo and the residue was dissolved in DCM (60 mL). The 1e (2.25 g, 3.90 mmol) was added under argon and then the TMS triflate was added slowly. The mixture was stirred for 10 minutes at RT and then refluxed for 4 hours. The mixture was added to cooled sodium hydrogen carbonate solution and extracted three times with EtOAc. The organic phase was washed with brine and dried over sodium sulfate. The solution was evaporated under reduced pressure and the mixture was purified by silica gel chromatography with isohexane and 20 to 50% ethyl acetate, which gave the two compounds diTIPS (1.29 g, 56%) and monoTIPS (390 mg, 23%).

Step g) 1-((2R,3S,4R,5R)-3-chloro-3-fluoro-4-hydroxy-5-(hydroxymethyl)tetrahydrofuran-2-yl)pyrimidine-2,4(1H,3H)-dione (1g)

A solution of 1f (1.27 g, 2.14 mmol) in 80% acetic acid was stirred at 80° C. for 18 h, then concentrated and co-evaporated with toluene. The residue was dissolved in dry THF (10 mL), triethylamine trihydrofluoride was added (1.38 g, 8.56 mmol) and the mixture was evaporated onto silica and purified by silica gel column chromatography eluted with DCM including κ to 10% MeOH. The mixed fractions were purified by HPLC on a Hypercarb column eluted with 10 to 20% acetonitrile and 10 mmol ammonium acetate, which gave the title compound (19 mg, 3.2%). MS 281.2 [M+H]t ¹H NMR (500 MHz, DMSO) δ 10.39 (s, 1H), 7.87 (d, J=8.1 Hz, 1H), 6.74 (s, 1H), 6.22 (d, J=16.1 Hz, 1H, 7), 5.73 (d, J=8.1 Hz, 1H), 5.52 (s, 1H), 4.21 (dd, J=19.6, 9.2 Hz, 1H), 3.87-3.77 (m, 2H), 3.64 (dd, J=12.7, 2.8 Hz, 1H).

¹³C NMR (126 MHz, DMSO) δ 162.76, 150.26, 139.06, 115.71, 113.71, 102.28, 86.98, 86.69, 81.01, 73.28, 73.14, 58.19.

Example 2

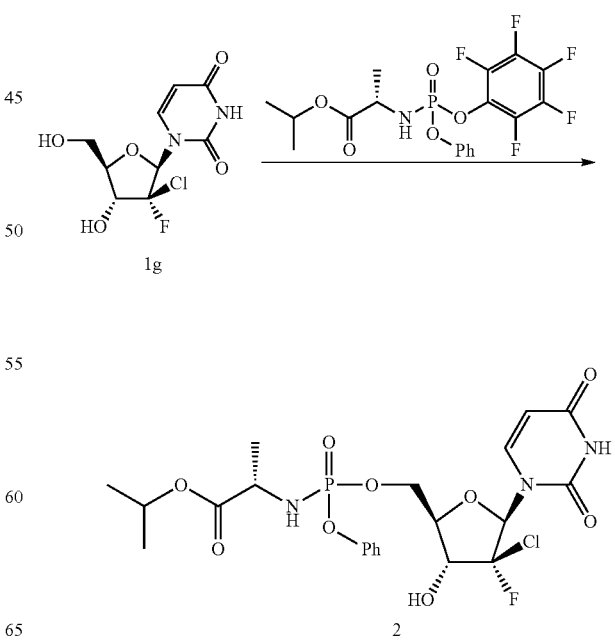

(2S)-isopropyl 2-(((((2R,3R,4S,5R)-4-chloro-5-(2,4-dioxo-3,4-dihydropyrimidin-1(2H)-yl)-4-fluoro-3-hydroxytetrahydrofuran-2-yl)methoxy)(phenoxy)phosphoryl)amino)propanoate (2)

A 1M solution of tert-butyl magnesium chloride (0.22 mL, 0.22 mmol) was slowly added under argon to a solution of sugar 1g (28 mg, 0.1 mmol) in THF (1.5 mL). The suspension was stirred for one h at 0° C., then DMPU (0.5 mL) was added followed by addition of a solution of (2S)-isopropyl 2-(((perfluorophenoxy)(phenoxy)phosphoryl)amino)propanoate (57 mg, 0.12 mmol) (prepared as described in WO2011/123672) in THF (0.5 mL) at 0° C. during ~5 min. The mixture was stirred for 5 h at 0° C., then allowed to attain RT and was quenched with saturated ammonium chloride solution. The mixture was extracted three times with EtOAc. The organic phase was dried (Na$_2$SO$_4$), concentrated under reduced pressure and the product was isolated by HPLC. (Gemini NX 30 mm 20 to 60% acetonitrile 10 mmol ammonium acetate Gradient 17 minutes and flow 40 ml per minute. The title compound was isolated as a single isomer at the phosphorus atom. Yield 22 mg, 40%. MS ES+ 550.4 [M+H]$^+$, ES− 547.9 [M−H]$^-$.

$^1$H NMR (500 MHz, DMSO) δ 1.15 (d, 6H), 1.23 (d, 3H), 3.80 (tq, 1H), 4.04 (m, 1H), 4.31 (m, 3H), 4.86 (hept, 1H), 5.63 (dd, 1H), 6.09 (dd, 1H), 6.24 (d, 1H), 6.66 (d, 1H), 7.21 (m, 3H), 7.38 (m, 2H), 7.58 (d, 1H), 11.63 (m, 1H).

$^{13}$C NMR (126 MHz, DMSO) δ 19.64 (d), 21.26, 21.30, 49.67, 64.32, 67.89, 74.42 (d), 78.81, 87.60 (m), 102.27, 113.96 (d), 119.96 (d), 124.52, 129.56, 139.91, 150.01, 150.53 (d), 162.52, 172.45 (d).

$^{31}$P NMR (162 MHz, DMSO) δ 3.76.

$^{19}$F NMR (376 MHz, DMSO) δ −119.05.

Example 3

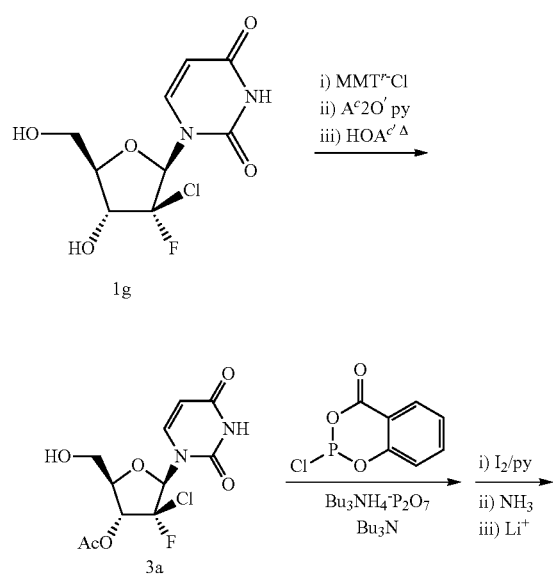

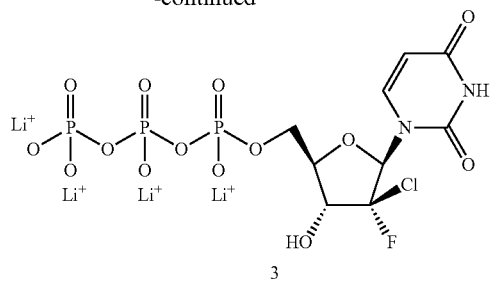

3

Step a) (2R,3R,4S,5R)-4-chloro-5-(2,4-dioxo-3,4-dihydropyrimidin-1(2H)-yl)-4-fluoro-2-(hydroxymethyl)tetrahydrofuran-3-yl acetate (3a)

4-methoxytrityl chloride (133 mg, 0.43 mmol) was added to a solution of compound 1f (81 mg, 0.29 mmol) in pyridine (25 mL). The resulting mixture was stirred at room temperature for 40 h, the diluted with DCM and washed with NaHCO$_3$. The organic phase was concentrated and the residue purified by column chromatography on silica gel, which gave the title compound (144 mg, 90%).

The afforded compound was dissolved in dry pyridine (1.4 mL), Ac$_2$O (29 µL, 0.31 mmol) was added and the solution was stirred at rt. After 2 h, MeOH was added, the mixture was concentrated and extracted with DCM (×3) and the combined organic layers were washed with sat. aq. NaHCO$_3$, Na$_2$SO$_4$, concentrated and co-evaporated once with THF.

The residue was taken up in 80% HOAc (35 mL) and stirred at 45° C. for 3 h, then concentrated. The residue was purified by column chromatography on silica gel, which gave the title compound (69 mg, 33%).

Step b) Lithium ((2R,3R,4S,5R)-4-chloro-5-(2,4-dioxo-3,4-dihydropyrimidin-1(2H)-yl)-4-fluoro-3-hydroxytetrahydrofuran-2-yl)methyl triphosphate (3b)

A freshly prepared solution of 2-chloro-1,3,2-benzodioxaphosphin-4-one (64 mg, 0.31 mmol) in anhydrous THF (280 µL) was added under nitrogen to a stirred solution of compound 3a (78 mg, 0.24 mmol) in a mixture of anhydrous pyridine (560 µL) and anhydrous THF (560 µL). The mixture was stirred at room temperature under nitrogen for 15 minutes, then a previously prepared solution of tributylammonium P$_2$O$_7$ (146 mg, 0.27 mmol) and tributylamine (127 µL, 0.53 mmol) in anhydrous DMF (560 µL) was added under nitrogen. The afforded solution was stirred for additional 15 minutes at room temperature under nitrogen, then I$_2$ (123 mg, 0.48 mmol) was added as a solution in pyridine/water (98/2, v/v) (1.1 mL) and the reaction mixture was stirred for 15 minutes. Excess iodine was destroyed by addition of ~19 drops of a 5% aqueous solution of Na$_2$SO$_3$ and the reaction solution was concentrated. The residue was taken in water/acetonitrile (95:5) (5 mL) and left shaking at room temperature for 30 minutes. Concentrated ammonia (10 mL) was added and the reaction mixture stirred for 1½ h at room temperature, then concentrated and the residue dissolved in water/acetonitrile (95:5, 5 mL) and freeze dried.

The crude material ~430 mg, was dissolved in 10% MeCN/water (3 mL) and filtered and purified by HPLC on a Gilson instrument using a Phenomenex Luna 5μ NH$_2$ (150×21.2 mm) column, Solvent A: 95% water:5% acetonitrile: 0.05M ammonium bicarbonate Solvent B: 95% water:5% acetonitrile: 0.8M ammonium bicarbonate Gradient: 0% B to 50% B in 30 min.

The NTP fractions were pooled and concentrated, the residue was dissolved in 10% MeCN/water and freeze dried. The afforded solids were taken up in 10% MeCN/water, insolubles were filtered off through 0.45 μm frit filters and the clear filtrate was evaporated to dryness, dissolved in water/acetonitrile (95:5), passed through Dowex-Li$^+$ and freeze-dried which gave the title compound (39.3 mg, 28%).

$^1$H NMR (500 MHz, D$_2$O) δ 7.87 (d, J=8.2 Hz, 1H), 6.41 (d, J=15.9 Hz, 1H, 1), 5.98 (d, J=8.2 Hz, 1H), 4.56 (dd, J=19.1, 9.4 Hz, 1H, 5), 4.35 (dddd, J=42.1, 12.3, 5.1, 2.2 Hz, 3H), 4.19 (d, J=9.4 Hz, 1H, 8).

$^{13}$C NMR (126 MHz, D$_2$O) δ 165.94, 151.67, 140.78, 114.54, 112.55, 103.12, 87.95, 87.62, 79.45, 79.38, 73.16, 73.02, 62.60, 62.56.

Example 4

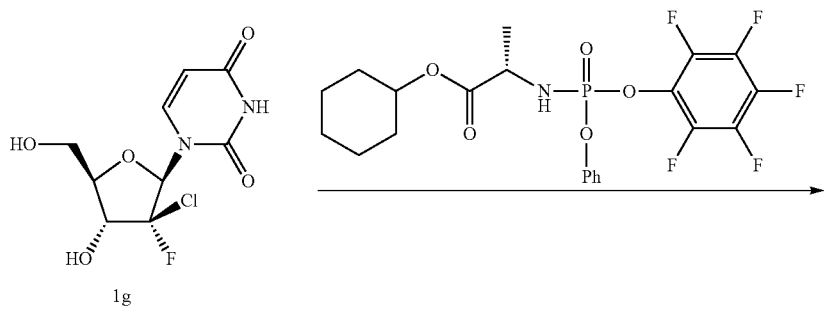

1g

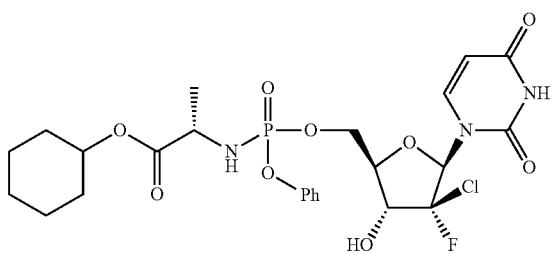

4

(2S)-cyclohexyl 2-(((((2R,3R,4S,5R)-4-chloro-5-(2,4-dioxo-3,4-dihydropyrimidin-1(2H)-yl)-4-fluoro-3-hydroxytetrahydrofuran-2-yl)methoxy)(phenoxy)phosphoryl)amino)propanoate (4)

t.BuMgCl (13.7 mg, 0.12 mmol) was added under N$_2$ at 0° C. to a solution of nucleoside 1g (15 mg, 0.053 mmol) in dry THF (2 mL). The resulting suspension was stirred for 1 h at 0° C., then DMPU (0.5 ml) was added followed by dropwise addition of a solution of (2S)-cyclohexyl 2-(((perfluorophenoxy)(phenoxy)phosphoryl)amino)propanoate (33 mg, 0.067 mmol) in THF (0.5 mL) keeping the temperature at 0° C. After 4 h, NH$_4$Cl (sat. aq.) was added and the mixture was extracted three times with EtOAc. The combined organic extracts were washed with water and brine, then dried (Na$_2$SO$_4$) and concentrated under reduced pressure. The afforded residue was purified using Biotage (SNAP 25 g) eluted with a gradient of DCM/MeOH followed by further purification using Waters Gemini nx C18 colon, pH 7. Appropriate fractions were pooled, concentrated and co-evaporated from water, then freeze dried from MeCN and water, which gave the title compound as a single stereoisomer at the phosphorus atom as a white powder, (9.9 mg, 31.4%). LC-MS 590.09 [M+H]$^+$.

The following compounds were synthesised as single stereoisomers at the phosphorus atom by phosphorylation of nucleoside 1g with the indicated phosphorylating agent using the procedure of Example 4:

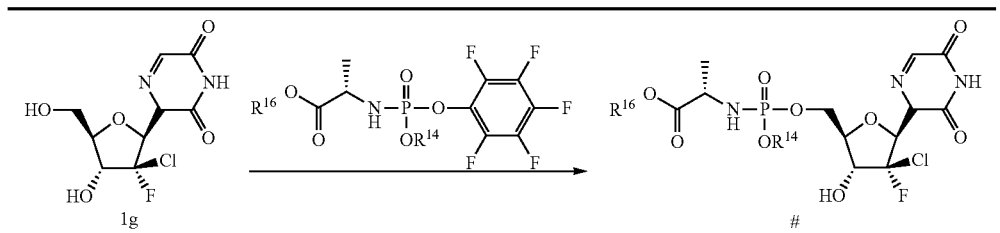

| Ex | Structure | P-agent | Yield | MS (ES) |
|---|---|---|---|---|
| 5 | 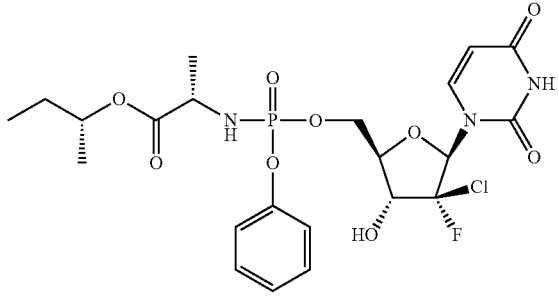 | 1-32 | 4.6 mg, 15% | 564.1 [M+H]$^+$ |
| 6 | 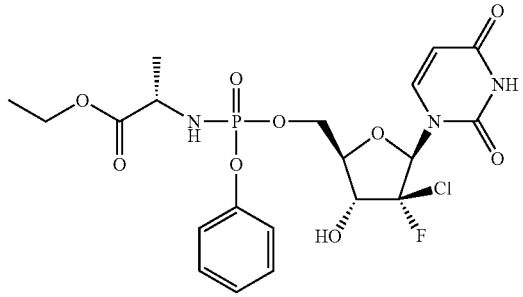 | 1-33 | 11 mg, 38% | 536.08 [M+H]$^+$ |

-continued
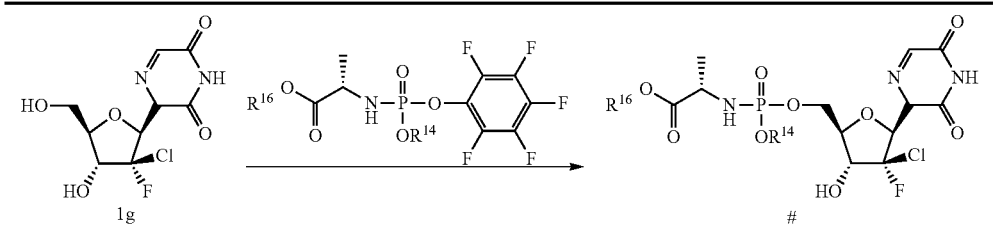
| Ex | Structure | P-agent | Yield | MS (ES) |
|---|---|---|---|---|
| 7 | 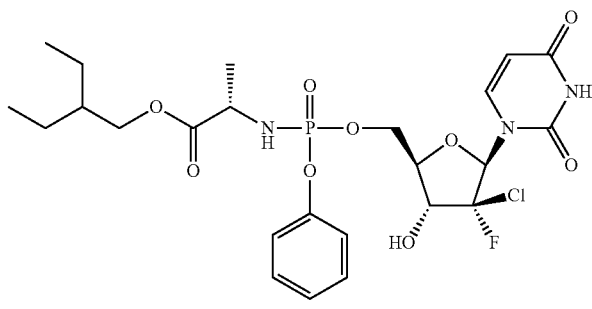 | 1-34 | 5.3 mg, 23%. | 589.93 [M +H]+ |
| 8 | 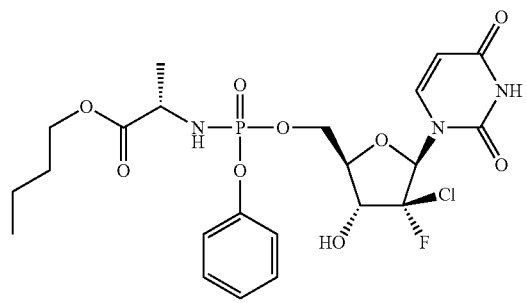 | 1-35 | 12 mg, 39% | 564.32 |
| 9 | 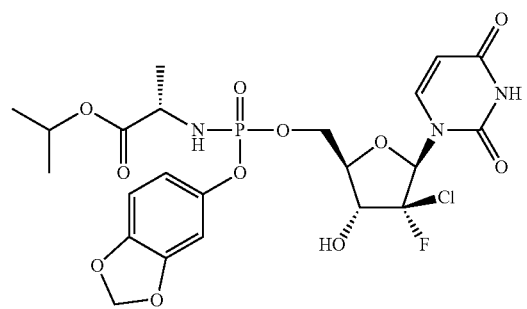 | 1-37 | 4.5 mg, 19% | 594.0 [M +H]+ |
| 10 | 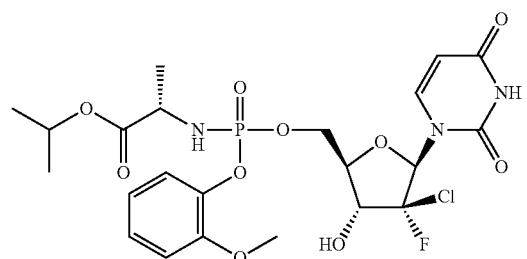 | 1-38 | 9.0 mg, 34% | 580.0 [M +H]+ |

-continued
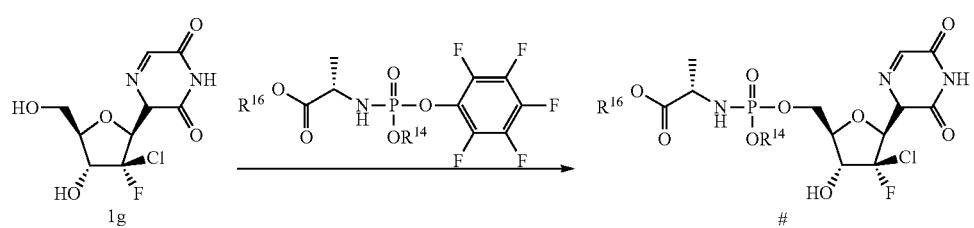
| Ex | Structure | P-agent | Yield | MS (ES) |
|---|---|---|---|---|
| 11 | 11 | 1-39 | 12 mg, 43% | 580.1 [M+H]+ |
| 12 | 12 | 1-40 | 5 mg, 7.7% | 590.0 [M+H]+ |
| 13 | 13 | 1-41 | 6.5 mg, 14% | 564.0 [M+H]+ |
| 14 | 14 | 1-42 | 2.1 mg, 4.5% | 549.9 [M+H]+ |

-continued
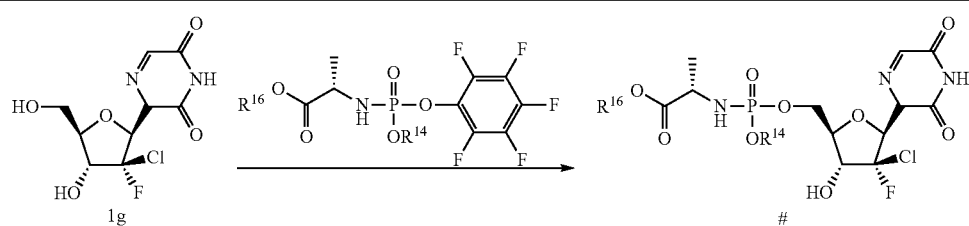
| Ex | Structure | P-agent | Yield | MS (ES) |
|---|---|---|---|---|
| 15 | 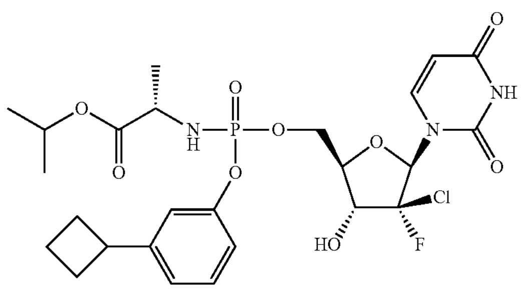 | 1-43 | 17 mg, 32% | 604.0 [M+H]+ |
| 16 | 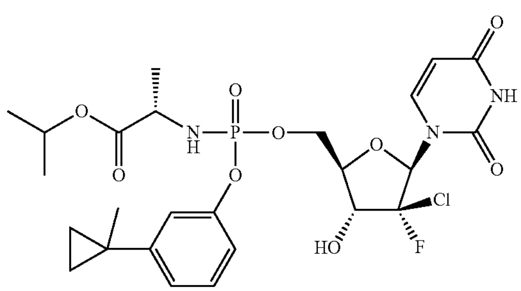 | 1-44 | 16 mg, 29% | 604.0 [M+H]+ |
| 17 | 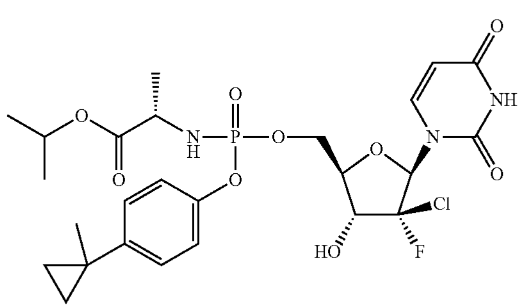 | 1-45 | 9.7 mg, 18% | 604.0 [M+H]+ |

Example 18

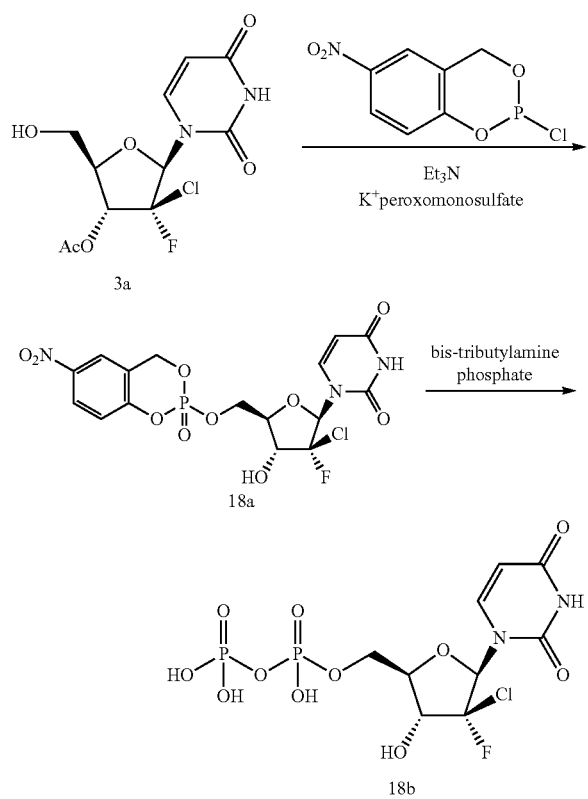

Step a) 1-((2R,3S,4R,5R)-3-Chloro-3-fluoro-4-hydroxy-5-(((6-nitro-2-oxido-4H-benzo[d][1,3,2]dioxaphosphinin-2-yl)oxy)methyl)tetrahydrofuran-2-yl)pyrimidine-2,4(1H,3H)-dione (18a)

Nucleoside 3a (69 mg, 0.21 mmol) was dissolved in a mixture of acetonitrile/dichloromethane: 2.7/1.3 (~4 mL) and the solution was cooled to −20° C. under nitrogen. To the solution was added Et$_3$N (77 μL, 0.56 mmol) followed by 2-chloro-6-nitro-4H-benzo[d][1,3,2]dioxaphosphinine (125 mg, 0.54 mmol) prepared as a solution in DCM (1.34 mL; 2 mmol was diluted to 5 mL to get stock solution). The cooling bath was removed and the reaction stirred at room temperature. After 1½ h, the reaction was cooled to −5° C. and a solution of Oxone®, (0.855 mmol) in water (4.0 mL) was added and the two-phase system was vigorously stirred for 15 min. The mixture was then extracted with EtOAc, the phases were separated and the organic phase was washed with cold water (2×), dried (Na$_2$SO$_4$). concentrated and co-evaporated from heptane/DCM, LCMS 536 [M+H]. This crude material was taken to next step.

Step b) ((2R,3R,4S,5R)-4-chloro-5-(2,4-dioxo-3,4-dihydropyrimidin-1(2H)-yl)-4-fluoro-3-hydroxytetrahydrofuran-2-yl)methyl trihydrogen diphosphate (18b)

Compound 18a was co-evaporated once with dry DMF, then dissolved in dry DMF (2.2 mL) and bis-tributylamine phosphate (0.25 mmol, 0.5 mL, 0.5M in DMF) was added under nitrogen. The solution was stirred ~17 h at room temperature, then concentrated in vacuum and a few mL of water was added followed by addition of conc. ammonia (25-30 mL) and a THF (1-2 mL) and this mixture was stirred at room temperature. After 2 h, most of the NH$_3$ was removed by evaporation and the residue was extracted with DCM (4×40 mL). The water layer was concentrated and the residue dissolved in 10% MeCN/Milli Q water. Insolubles were filtered off and the filtrate was concentrated to dryness.

The afforded residue was dissolved in 10% MeCN/water (1.5 mL), loaded onto an active carbon column (0.85×3.00 cm) and eluted with 10% MeCN/Milli Q water. Appropriate fractions were pooled, concentrated, co-evaporated with MeCN (×2) and finally dried on a freeze dryer. The crude residue (76 mg) was dissolved in 10% MeCN/Milli Q water (1 mL) and purified by semi-preparative HPLC on a Luna NH$_2$ column on Gilson machine using a gradient (30 mL/min) from 0% B to 30% B over 20 min (Solvent A: 0.05M ammonium bicarbonate, 5% acetonitrile; Solvent B: 0.8M ammonium bicarbonate, 5% acetonitrile). Appropriate fractions were pooled and concentrated to dryness, the residue dissolved in Milli Q water with some MeCN and freeze dried. The fluffy residues were taken up in 10% MeCN in Milli Q water, the suspension was filtered through a 0.2 μm filter and the clear filtrates were pooled and freeze dried, which gave the title compound (28.6 mg, 36%). LCMS ES$^-$ 438.8 [M−H]$^-$.

Example 19

Alternative Route to Compound 1g

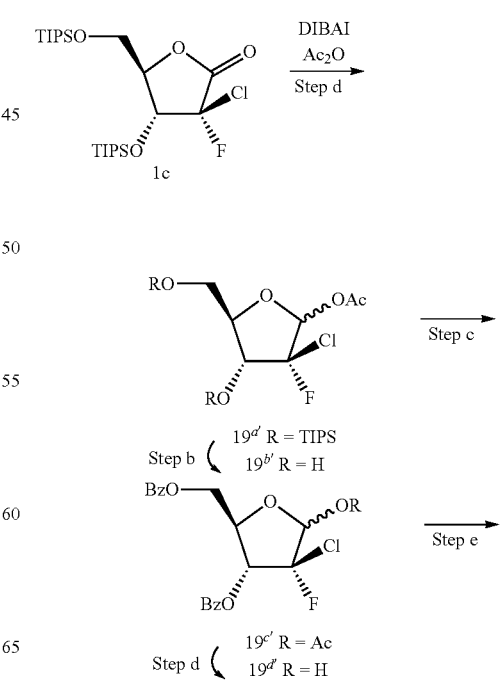

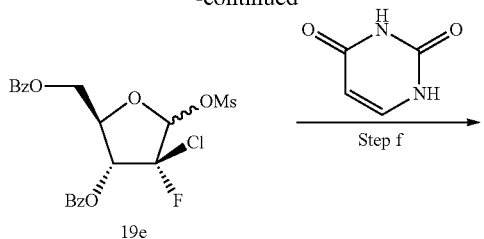

19e

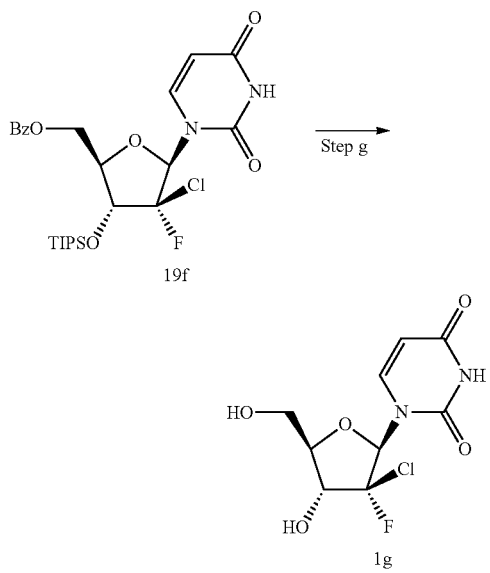

19f

1g

Step a) (3S,4R,5R)-3-Chloro-3-fluoro-4-((triisopropylsilyl)oxy)-5-(((triisopropylsilyl)oxy)methyl)-tetrahydrofuran-2-yl acetate (19a)

A 1M solution of Li(O-t-Bu)$_3$AlH in THF (39 mL, 39 mmol) was added dropwise under argon at −35° C. to solution of compound 1c (16.3 g, 32.8 mmol) in THF (120 mL). The mixture was stirred for 1 h at −35° C., then at rt for 1 h. The mixture was cooled to −25° C., DMAP (4.00 g, 32.8 mmol) was added and the mixture was stirred for 15 minutes, then acetic anhydride (33.5 g, 328 mmol) was added drop wise and the mixture was stirred 2 h. The mixture was allowed to come to 0° C. and EtOAc (200 mL) and water (200 mL) were added. The phases were separated and the water phase was extracted with EtOAc (×2). The combined organic phases were washed with water (×2) and with brine (×1). The organic phase was dried (Na$_2$SO$_4$), filtered and concentrated under reduced pressure. The residue was co-evaporated twice with toluene and the product was purified by chromatography on silica gel with eluted with isohexane and 2 to 6% EtOAc, which gave the title compound (17.1 g, 96%).

Step b) (3S,4R,5R)-3-Chloro-3-fluoro-4-hydroxy-5-(hydroxymethyl)tetrahydrofuran-2-yl acetate (19b)

Triethylamine tri hydrofluoride (20.5 g, 126 mmol) was added to a stirred solution of compound 19a (17.0 g, 31.4 mmol) in acetonitrile (115 mL) and THF (23 mL). The mixture was stirred for 72 h at rt, 20 h at 50° C. and then at rt overnight. The solution was concentrated on silica (60 g) and purified by silica gel chromatography eluted with a gradient of isohexane and EtOAc, which gave the title compound (68.0 g, 85%).

Step c) (2R,3R,4S)-5-Acetoxy-2-((benzoxy)methyl)-4-chloro-4-fluorotetrahydrofuran-3-yl benzoate (19c)

Triethylamine (10.8 g, 107 mmol) was added to a stirred solution of compound 19b (6.80 g, 26.8 mmol) under ice cooling followed by drop wise addition of benzoyl chloride (9.41 g, 66.9 mmol).

The mixture was allowed to attain rt and stirred overnight. EtOH (5 mL) was added and the mixture was stirred for 30 minutes, then concentrated in vacuo. Water was added and the mixture was extracted with EtOAc (×3). The organic phase was washed with water and brine, dried (Na$_2$SO$_4$), filtered and concentrated under reduced pressure. The product was purified by silica gel chromatography eluted with a gradient of isohexane and EtOAc, which gave the title compound (10.1 g, 86%).

Step d) ((2R,3R,4S)-3-(Benzoyloxy)-4-chloro-4-fluoro-5-hydroxytetrahydrofuran-2-yl)methyl benzoate (19d)

Ethanolamine (1.55 g, 25.4 mmol) was added to a stirred solution of compound 19c (10.1 g, 23.0 mmol) in EtOAc (100 mL) and DMSO (50 mL). The mixture was stirred at rt for 72 h, then diluted with diethyl ether (300 mL) and EtOAc (300 mL) and washed with water (×4). The combined water phases were extracted with EtOAc then the EtOAc phase was washed with brine (×2). The combined organic phases were dried (Na$_2$SO$_4$), filtered and concentrated under reduced pressure. The product was purified by silica gel chromatography eluted with a gradient of DCM with and EtOAc, which gave the title compound (7.50 g, 82%).

Step e) ((2R,3R,4S)-3-(benzoyloxy)-4-chloro-4-fluoro-5-((methylsulfonyl)oxy)tetrahydrofuran-2-yl)methyl benzoate (19e)

Et$_3$N (3.54 mL, 25.4 mmol) was added at −15° C. under N$_2$ to a solution of compound 19d (8.36 g, 21.2 mmol) in dry DCM (100 mL) followed by addition of MsCl (1.97 mL, 25.4 mmol). The reaction mixture was stirred at −15° C. for 2 h, then poured into HCl (80 mL, 1M, aq.). The phases were separated and the aqueous layer was extracted with DCM. The combined organic extracts were washed with NH$_4$Cl (sat. aq.) dried (MgSO$_4$) and concentrated under reduced pressure to give the title compound (9.86 g, 98%) as a clear oil.

Step f) ((2R,3R,4S,5R)-3-(benzoyloxy)-4-chloro-5-(2,4-dioxo-3,4-dihydropyrimidin-1(2H)-yl)-4-fluoro-tetrahydrofuran-2-yl)methyl benzoate (19f)

Uracil (3.09 g, 27.5 mmol) and ammonium sulfate (48.5 mg, 0.367 mmol) was heated to reflux under $N_2$ in HMDS (49.3 mL, 236 mmol) for 16 h. The reaction mixture was cooled to rt, concentrated under reduced pressure and dried in vacuo. The residue in dry DCE (50 mL) was added under $N_2$ to a solution of compound 19e (8.68 g, 18.4 mmol) in dry DCE (75 mL). TMSOTf (6.12 g, 27.5 mmol) was slowly added under $N_2$ to the solution. After the addition, the reaction mixture was heated to 80° C. for 5 h and then at 65° C. for 16 h.

The reaction mixture was cooled to rt, quenched with $NaHCO_3$ (sat. aq.), filtered and extracted twice with DCM. The combined organic extracts were dried ($MgSO_4$) and concentrated under reduced pressure. EtOAc and DCM was added and the formed precipitate was collected by filtration which gave the pure β-isomer (660 mg, 7.4%). The filtrate was evaporated onto silica and purified by flash chromatography (hex:EtOAc 2:1-1:1), which gave the title compound as a mixture with the α-isomer, α:β>5:95 (942 mg, 11%).

Step e) 1-((2R,3S,4R,5R)-3-chloro-3-fluoro-4-hydroxy-5-(hydroxymethyl)tetrahydrofuran-2-yl)pyrimidine-2,4(1H,3H)-dione (19g)

Compound 19f (670 mg, 1.37 mmol) was suspended in $NH_3$ (7N in MeOH). After 30 min, EtOH (5 mL) was added and the suspension was stirred at rt. After an additional hour, the suspension went into solution and then reaction mixture was stirred at rt for 15 h. The solvents were evaporated under reduced pressure and the afforded residue was purified by flash chromatography (DCM:MeOH 10:1) which gave the title compound (380 mg, 99%) as a white solid. LC-MS ES− 279.31 [M−H]−.

The following compounds were synthesised as single stereoisomers at the phosphorus atom by phosphorylation of nucleoside 1g with the indicated phosphorylating agent using the procedure of Example 4:

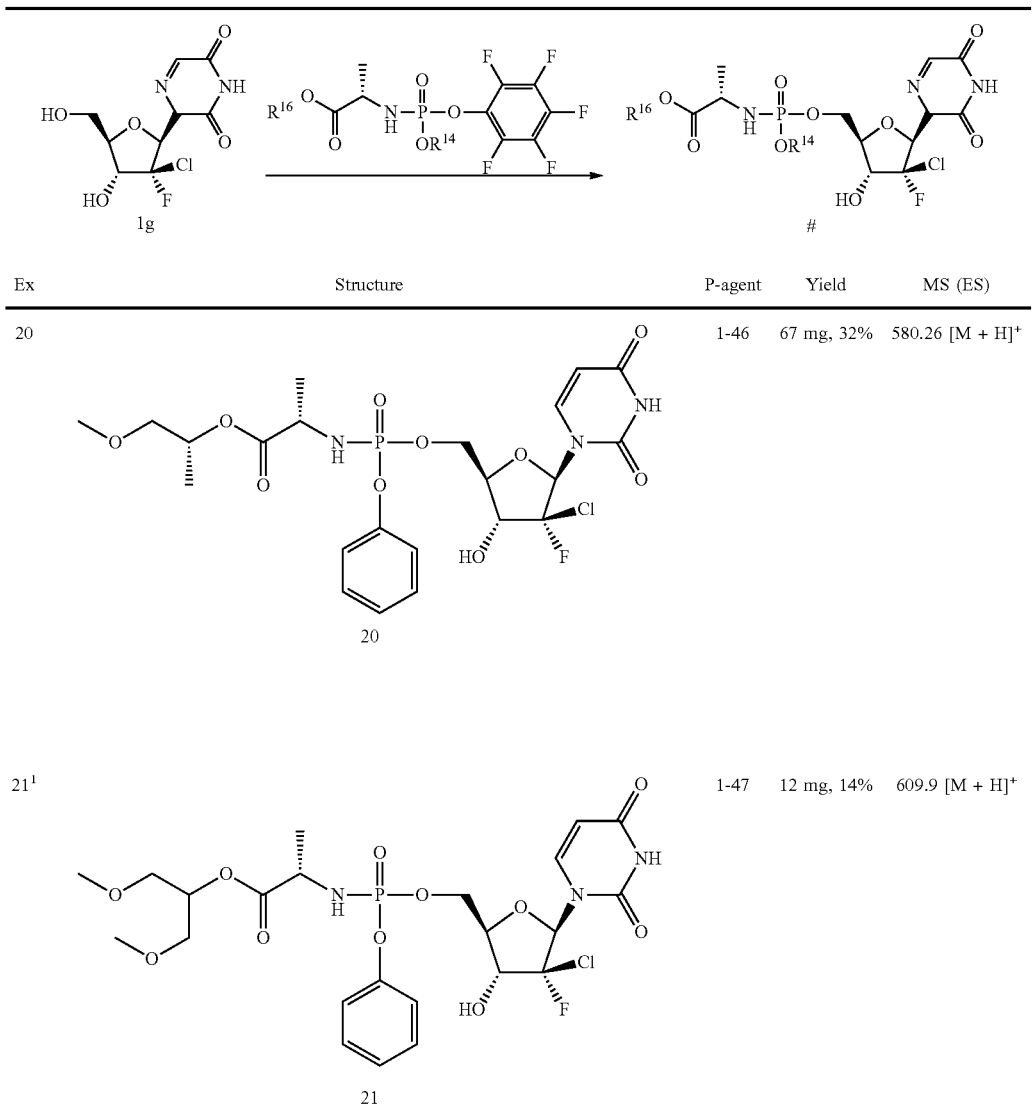

| Ex | Structure | P-agent | Yield | MS (ES) |
|---|---|---|---|---|
| 20 | 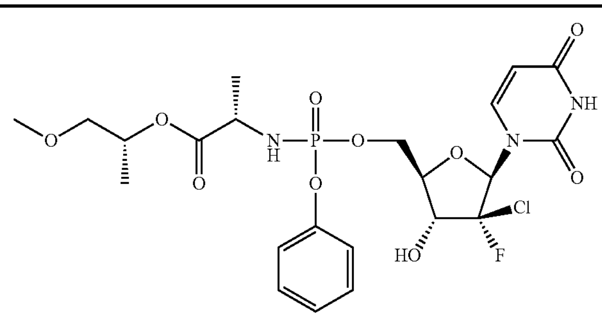 | 1-46 | 67 mg, 32% | 580.26 [M + H]+ |
| 21[1] | 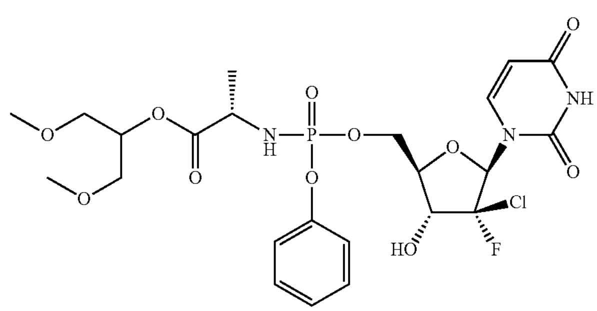 | 1-47 | 12 mg, 14% | 609.9 [M + H]+ |

-continued
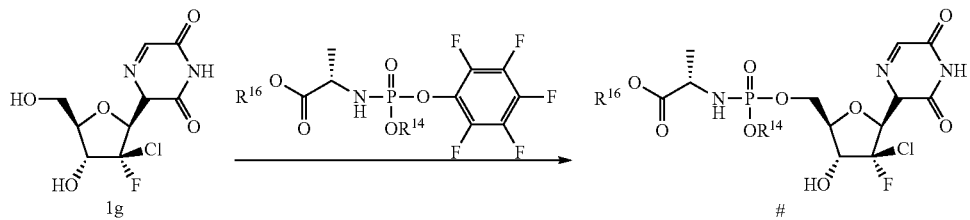
| Ex | Structure | P-agent | Yield | MS (ES) |
|---|---|---|---|---|
| 22 | 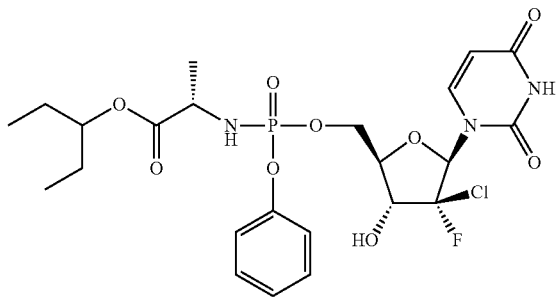 | 1-48 | 54 mg, 24% | 578.0 [M + H]⁺ |
| 23[2] | 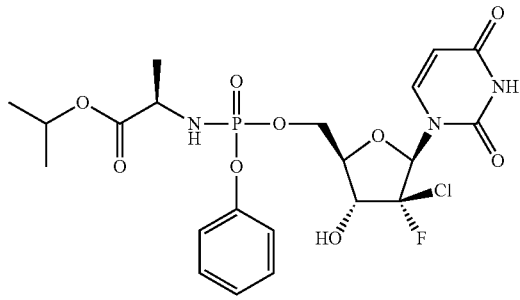 | 1-49 | 7.1 mg, 12% | 549.94 [M + H]⁺ |
| 24 | 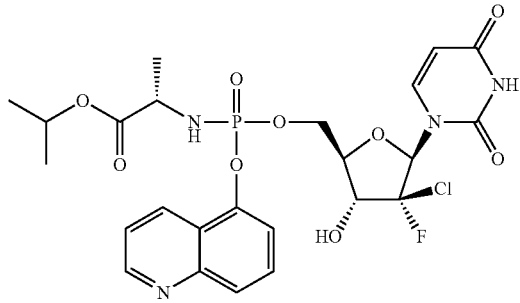 | 1-50 | 31 mg, 28% | 601.2 [M + H]⁺ |

-continued

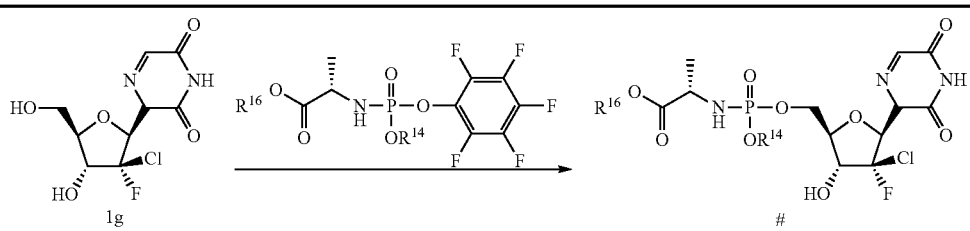

| Ex | Structure | P-agent | Yield | MS (ES) |
|---|---|---|---|---|
| 25 | 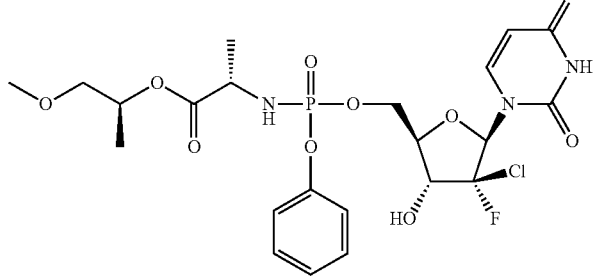 25 | 1-51 | 37 mg, 18% | 580.1 [M + H]+ |

¹No DMPU present in reaction mixture
²An additional 0.8 Eq of the phosphorylating agent (1-49) was added after 18 h

Example 26

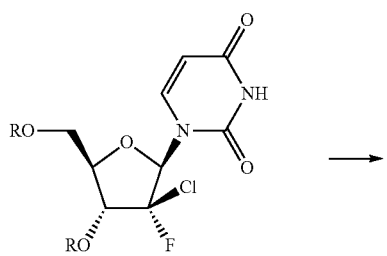

1g' R = H
26a' R = Tol

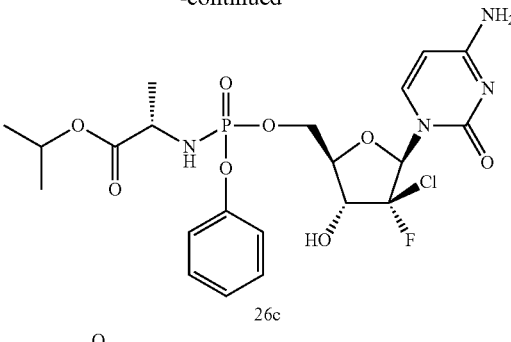
26b

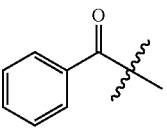
26c

Tol = 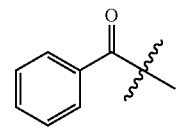

Step a) (2R,3R,4S,5R)-4-Chloro-5-(2,4-dioxo-3,4-dihydropyrimidin-1(2H)-yl)-4-fluoro-2-(((4-methylbenzoyl)oxy)methyl)tetrahydrofuran-3-yl 4-methylbenzoate (26a)

Nucleoside 1g (253 mg, 0.9 mmol) was dissolved in pyridine (5 ml) and DCM (5 ml). Triethylamine (630 µl, 4.52 mmol) was added and the mixture was cooled on an ice bath. After 15 min, 4-methylbenzoyl chloride (300 µl, 2.27 mmol) was added and the mixture was stirred with cooling for 10 min then at 22° C. for 90 min. NaHCO₃ (aq) was added and the mixture was diluted with DCM and washed with 1M HCl (aq) ×3, dried (Na₂SO₄) and concentrated. The residue was purified by column chromatography on silica eluted with petroleum ether/EtOAc (3:1) which gave the title compound (279.2 mg, 60%).

Step b) 4-Amino-1-((2R,3S,4R,5R)-3-chloro-3-fluoro-4-hydroxy-5-(hydroxymethyl)-tetrahydrofuran-2-yl)pyrimidin-2(1H)-one (26b)

Compound 26a (279 mg, 0.54 mmol) was dissolved in pyridine (5 mL), molecular sieves (4 Å, half spoon) was added and the mixture was stirred on an ice bath for 15 min. Phosphorus oxychloride (200 µl, 2.18 mmol) was added and after 5 min 1,2,4-1H-triazole (373 mg, 5.4 mmol) was added. The mixture was stirred with cooling for 15 min then at 22° C. for 5 h. Ammonia (32%, 10 mL, 82.2 mmol) was added and the mixture was stirred overnight at 22° C. The mixture was concentrated, dissolved in water and washed with EtOAc ×2. The combined organic layers were extracted with water, the combined water extracts were concentrated, and the residue was purified by column chromatography on silica eluted with DCM/MeOH (8:2) which gave the title compound (139 mg, 83%). MS ES+ 279.9 [M+H]$^+$.

Step c) (2S)-Isopropyl 2-(((((2R,3R,4S,5R)-5-(4-amino-2-oxopyrimidin-1(2H)-yl)-4-chloro-4-fluoro-3-hydroxytetrahydrofuran-2-yl)methoxy)(phenoxy)phosphoryl)amino)propanoate (26c)

Compound 26b (27.4 mg, 0.1 mmol) was dissolved in dry THF (6 mL) containing molecular sieves, and the mixture was stirred at 22° C. for 30 min then 2M tert-butylmagnesium chloride in THF (0.11 ml) was added and the mixture was stirred another 30 min. (2S)-Isopropyl 2-(((perfluorophenoxy)(phenoxy)phosphoryl)amino)propanoate (51.4 mg, 0.11 mmol) was added and the mixture was stirred for 15 h, then diluted with EtOAc, washed with NaHCO$_3$ (aq), dried (Na$_2$SO$_4$) filtered and concentrated. The residue was purified by YMC-silica eluted with a gradient of DCM:MeOH (95:5→90:10). Appropriate fractions were pooled and concentrated. The residue was purified by preparative HPLC using a Gemini C18 column eluted with a gradient of acetonitrile/water (pH 7, 0.01M NH$_4$OAc, 20-40%). The product was concentrated then purified on a fluorophenyl column eluted with a gradient of MeOH/water (pH 7, 0.01 M NH$_4$OAc, 33-50%). The product was collected, dissolved in acetonitrile/water (1:4) and lyophilized which gave the title compound as a single stereoisomer at the phosphorus atom (13 mg, 24%) LC-MS 548.9 [M+H]$^+$.

Example 27

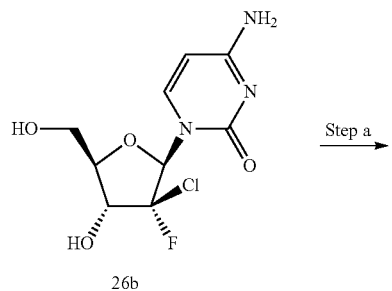

26b

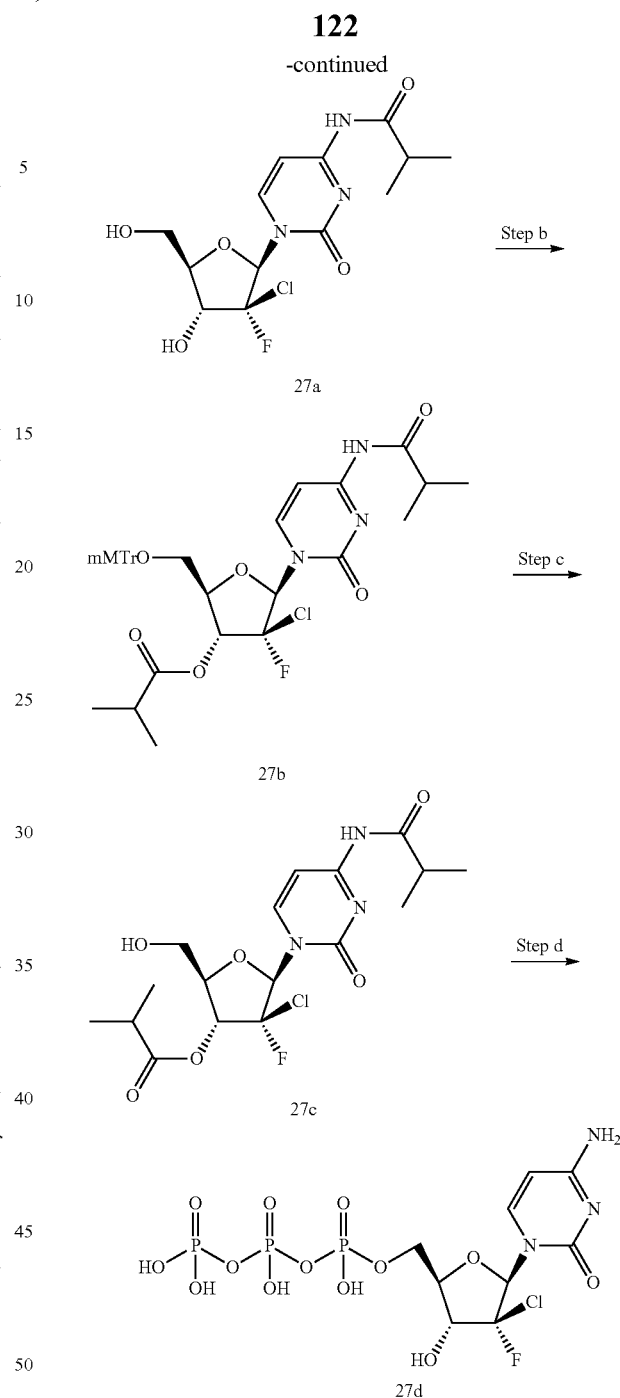

Step a) N-(1-((2R,3S,4R,5R)-3-chloro-3-fluoro-4-hydroxy-5-(hydroxymethyl)tetrahydrofuran-2-yl)-2-oxo-1,2-dihydropyrimidin-4-yl)isobutyramide (27a)

Isobutyric anhydride (118 mg, 0.746 mmol) was added at 58° C. to a solution of nucleoside 26b (139 mg, 0.497 mmol) in dioxane (1.7 mL) and water (0.19 mL). The solution was stirred for 3 h at 58° C., then concentrated. The residue was dissolved in 20% EtOH in DCM and washed (×4) with sat.aq. NaHCO$_3$/brine 30:70 v/v, dried (Na$_2$SO$_4$) filtered and concentrated. The residue was purified by column chromatography on silica gel eluted with a gradient of EtOH/DCM (2→8%), which gave the title compound as a solid (62 mg).

Step b) (2R,3R,4S,5R)-4-chloro-4-fluoro-5-(4-isobutyramido-2-oxopyrimidin-1(2H)-yl)-2-(((4-methoxyphenyl)diphenylmethoxy)methyl)tetrahydrofuran-3-yl isobutyrate (27b)

4-Methoxytrityl chloride (65.7 mg, 0.177 mmol) was added to a solution of compound 27a (62 mg, 0.177 mmol) in pyridine (1.1 mL) and the resulting mixture was shaken at room temperature for about 6 h, then additional 4-methoxytrityl chloride (16 mg, 0.3 eq.) was added and the mixture was shaken for further 18 h. Isobutyric anhydride (33.6 mg, 0.212 mmol) was added and the solution was shaken at rt for 4 h. The reaction was quenched with MeOH, then concentrated and extracted with DCM(×3)/sat. aq. NaHCO$_3$. The organic phase was dried (Na$_2$SO$_4$) filtered and concentrated and the residue was co-evaporated twice with toluene and twice with THF. The afforded solid residue was taken directly to the next step.

Step c) (2R,3R,4S,5R)-4-Chloro-4-fluoro-2-(hydroxymethyl)-5-(4-isobutyramido-2-oxopyrimidin-1(2H)-yl)tetrahydrofuran-3-yl isobutyrate (27c)

Compound 27b (123 mg, 0.177 mmol) was dissolved in 80% AcOH (25 mL) and THF (5 mL) and the solution was stirred at 45° C. for 2 h, then concentrated and co-evaporated with THF (×3) and toluene (×1). The residue was purified by column chromatography on silica geleluted with a gradient of 0→4% EtOH in DCM, which gave the title compound (36 mg, 48.5% over 3 steps). LC-MS 420.0 [M+H]$^+$.

Step d) (((2R,3R,4S,5R)-5-(4-amino-2-oxopyrimidin-1(2H)-yl)-4-chloro-4-fluoro-3-hydroxytetrahydrofuran-2-yl)methyl)triphosphoric acid (27d)

Compound 27c (36.0 mg, 0.086 mmol) was dissolved in a mixture of MeCN/DCM: 1.06/0.54 (~1.6 mL) and the solution cooled to −20° C. under nitrogen. Et$_3$N (31.1 μl, 0.223 mmol) was added to the solution followed by addition of a solution of 2-chloro-6-nitro-4H-benzo[d][1,3,2]dioxaphosphinine (50.1 mg, 0.214 mmol) in DCM (0.71 mL). The cooling bath was removed and the reaction was stirred at room temperature for 1½ h. The reaction was cooled to −5° C. and a solution of Oxone® (0.343 mmol in water (1.73 mL) was added and the two-phase system vigorously stirred for 15 min. The mixture was extracted with ethyl acetate, the organic phase was washed with cold water (2×), dried (Na$_2$SO$_4$) and concentrated. The residue was co-evaporated once with toluene and once with dry DMF, then dissolved in dry DMF (1 mL). Tributylamine pyrophosphate (0.1 mmol, 54.6 mg) was added under nitrogen and the solution shaken for ~18 h at room temperature, then concentrated. 30% MeCN/H$_2$O (~20 mL) was added to the residue and the solution was shaken for 20-25 min at rt. The volatiles were evaporated and the residual oil-solid mix was dissolved in conc. ammonia (10-15 mL) and shaken at room temperature for about 5 h.

Most of the NH$_3$ was removed by evaporation then the residue was extracted with DCM (4×40 mL). The organic extracts were discarded and the water layer was concentrated. The residue was dissolved in 5% MeCN in water (1.5-2.0 mL) and loaded onto an active carbon column (0.85×2.5). The column was washed with 5% MeCN in water and 6-7 mL of eluent was collected and concentrated and freeze dried. The residue was dissolved in 5% MeCN/water (1.6 mL) and purified by semi-preparative HPLC using a Phenomenex Luna 5μ NH$_2$ column on Gilson machine eluted with a gradient (30 mL/min) from 0% B to 40% B over 30 min (Solvent A: 0.05M ammonium bicarbonate, 5% acetonitrile; Solvent B: 0.8M ammonium bicarbonate, 5% acetonitrile). Appropriate NTP fractions were pooled and concentrated to dryness, the residue was dissolved in MQ water with 5% MeCN and freeze dried. The residue was taken up in 5% MeCN in MQ water (4-5 mL) and the suspension was filtered through a 0.45 μm filter and the filtrate was concentrated. The residue was dissolved in 5% MeCN in water (0.5 mL) and applied onto a short Li+ Dowex column (6×1 cm) and washed with the 5% MeCN in water. The first ~10 mL was pooled, concentrated and freeze dried, which gave the title compound (11.7 mg, 30%) in 89% purity containing 6.6% NDP according to PI analysis. MS ES+ 519.9 [M+H]$^+$.

Example 28

Alternative Route to Compound 2

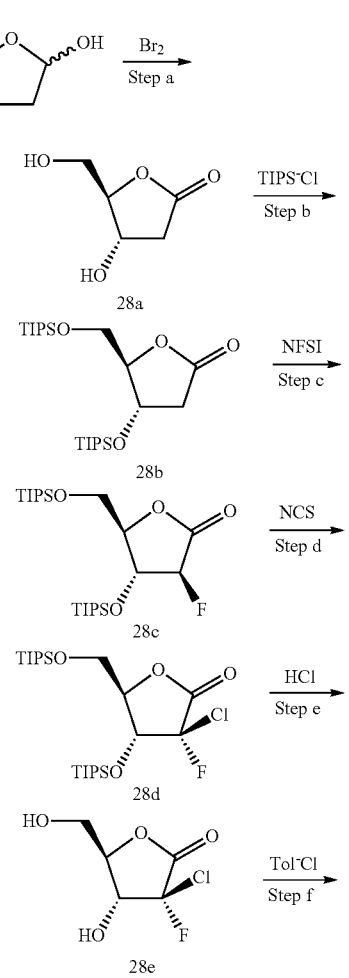

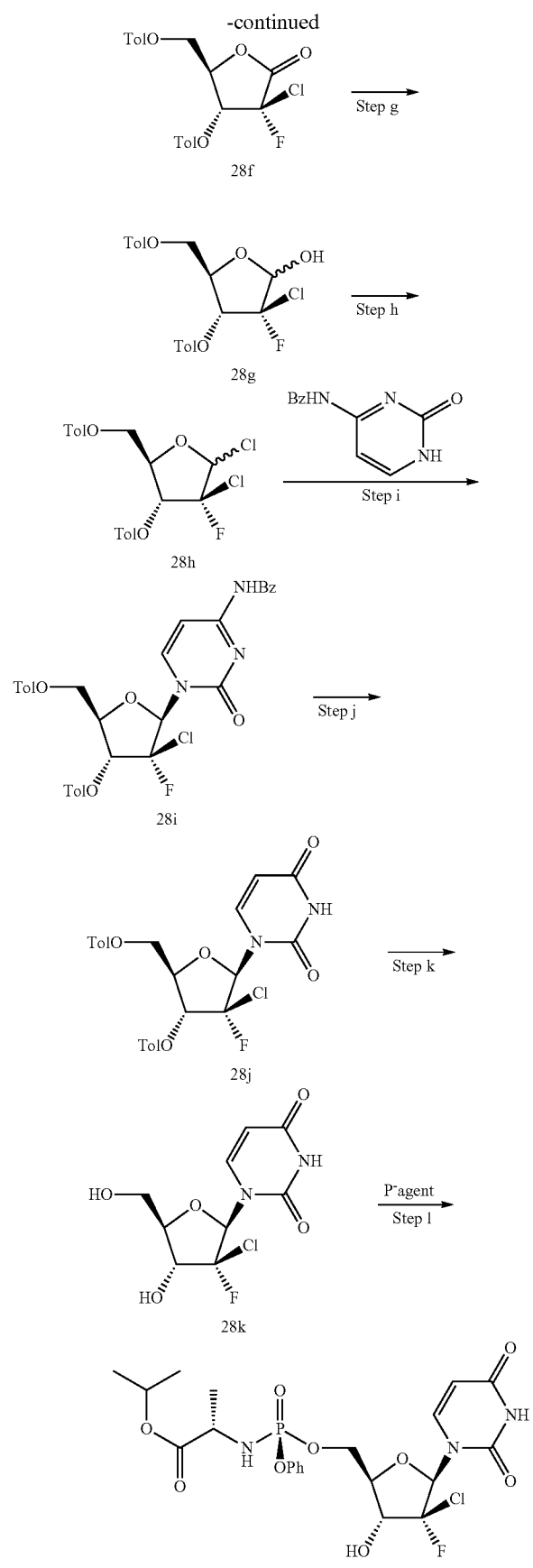

Step a) (4S,5R)-4-Hydroxy-5-(hydroxymethyl)dihydrofuran-2(3H)-one (28a)

Deoxy-D-ribose (400.0 g, 2.98 mol) was dissolved in water (1.6 kg) under nitrogen and the solution cooled to 3-7° C. Bromine (800 g, 10.0 mol, 3.36 eq.) was added at 3-7° C. while stirring over a period of approximately 2 hours and the stirring was continued at 3-7° C. for approximately 1 hour. The reaction mixture was gently warmed to 20-25° C. and then stirred for approximately 20 hours.

The reaction mixture was cooled to −5 to −7° C. and a solution of sodium hydroxide (27.65%, 720 g, 1.67 eq.) was added while keeping the reaction temperature at −3 to −7° C. The temperature was then adjusted to 0-5° C. and aqueous sodium hydroxide (9%, 470 g, 1.06 mol, 0.35 eq. was added at 0-5° C. to obtain a final pH=1.40.

The water was distilled off at reduced pressure using a scrubber (cooled, 14% sodium hydroxide, 0.9 L), finally at p<5 mbar and 50° C. In order to remove residual water from the product, 2-propanol was added portion wise to the residue followed by azeotropic distillation at reduced pressure. The final water content was determined by KF titration to be less than 1%. 2-Propanol (400 mL) was added to the residue and the mixture followed by filtration. The filter cake was washed with 2-propanol (1 L). The solvent was distilled off at reduced pressure. Toluene (400 mL) was added and distillation was resumed in order to remove residual 2-propanol and possibly more water. A residue of 474.6 g (120% yield) was obtained.

Step b) (4S,5R)-4-((Triisopropylsilyl)oxy)-5-(((triisopropylsilyl)oxy)methyl)dihydrofuran-2(3H)-one (28b)

Compound 28a (470.9 g, 2.97 mol) was dissolved in DMF (1.2 L) and cooled to 10-15° C. Imidazole (707.0 g, 10.4 mol, 3.5 eq.) was added and the temperature of the mixture was adjusted to 3-7° C. TIPS-Cl (1145 g, 5.94 mol, 2.0 eq.) was added with cooling to 3-7° C. over a period of 2 hours. The reaction mixture was stirred at 3-7° C. for another ½ h, then gently warmed to 20-25° C. and stirred for 20 h. The progress of the reaction was monitored as follows: A sample of the reaction mixture was diluted 10 times with dry DMF, N;O-bis(trimethylsilyl)trifluoroacetamide (0.25 mL) was added to 0.5 mL of the sample in DMF and analyzed by GC. If the reaction was not complete the necessary amount of TIPS-Cl was calculated and added and the stirring continued for another 20 hours.

When the reaction was completed, methanol (50 mL) was added and the mixture was stirred for ½-1 hour at 20-25° C. Water (1.2 kg) was added and the temperature of the mixture was adjusted to 15-25° C. pH was adjusted to pH 2.0-2.5 by careful addition of 36% hydrochloric acid (491 g, 4.7 mol). Toluene (0.9 kg) was added and the phases were separated. The organic phase was washed twice with 5% aqueous sodium chloride (1 kg). the aqueous phases were washed with toluene (0.9 kg). The organic phases were combined and dried with sodium sulfate (150 g) for minimum 1 hour. The suspension was filtered on a column prepared from silica Gel 60 (210 g) and toluene and the column was washed with toluene (1.1 kg). The combined filtrate was concentrated to dryness at reduced pressure at 50° C. which gave the title compound (1338 g, 84.4% from crude 2a). Purity (GC): 93.9%.

Step c) (3S,4R,5R)-3-fluoro-4-((triisopropylsilyl)oxy)-5-(((triisopropylsilyl)oxy)methyl)-dihydrofuran-2(3H)-one (28c)

Compound 28b (450.0 g, 1.01 mol,) and NFSI (348.0 g, 1.10 mol) were dissolved in Me-THF (2.2 L) under argon. The solution was cooled to below −75° C. and lithium bis(trimethylsilyl)amide (20.2% in THF, 1.190 kg, 1.42 eq.) was added over a period of 3-4 hours. The progress of the reaction was monitored by GC, and when deemed completed, methylsulfide (6 g, 0.1 mol) was added to quench residual NFSI and the stirring continued for another 20-30 minutes.

The reaction mixture was transferred into aqueous 12.5% ammonium chloride (1.7 kg) and the mixture was warmed to room temperature. The aqueous layer (Aq. 1) was separated and the organic phase was washed with purified water (1 L). The aqueous wash (Aq. 2) was separated and the organic phase was secured. Aq.1 was washed with heptanes (0.6 kg). The aqueous phase was separated and then discarded. Aq. 2 was added to the organic phase and the mixture was stirred for 1 minute. The aqueous phase was separated and discarded. The two organic phases were combined and concentrated at reduced pressure at 50° C. Heptanes (0.7 kg) was added to the residue and the resulting suspension was filtered. The filter cake was washed with heptanes (0.2 kg), the combined filtrate was concentrated at reduced pressure at 50° C., which gave 506 g crude product. The crude product was dissolved in a mixture of heptanes and toluene (0.5 L, 3:1) and purified by column chromatography on silica gel (silica gel 60, 2.5 kg and heptanes/toluene 3:1 v/v). The column was eluted with heptanes/toluene (3:1, 5.0 L), heptanes/toluene (2:1, 2.5 L), heptanes/toluene (3:1, 2.5 L) and toluene (7.5 L). Fractions of ~1 L were collected and fractions holding pure compound 2c were combined and concentrated and fractions holding mixtures of compound 2c and di-fluoro compound were combined and re-purified.

The above procedure was repeated twice, starting with 450 g and 525 g of compound 2b. Total yield of the title compound was 877.1 g (59.2%)+104.1 g (7.0%) from reworked material. Purity (GC): 92.4%.

Step d) (3S,4R,5R)-3-Chloro-3-fluoro-4-((triisopropylsilyl)oxy)-5-(((triisopropylsilyl)oxy)methyl)-dihydrofuran-2(3H)-one (28d)

Compound 28c (400.0 g, 0.86 mol) and NCS (138.0 g, 1.04 mol, 1.2 eq.) were stirred in THF (2.0 L) under argon at ~20° C. The suspension was cooled to below −70° C. and then lithium bis(trimethylsilyl)amide (20.2% in THF, 1.150 kg, 1.6 eq.) was added over a period of 1-1.5 hours. The reaction was monitored by GC and when deemed completed, the mixture was transferred into a 12.5% aqueous solution of ammonium chloride (1.5 kg). The mixture was warmed to room temperature. The stirring was stopped and the aqueous layer was separated, washed with heptanes (0.8 L) and then discarded.

The mother organic phase was concentrated to dryness at reduced pressure at 55° C. and then added to the heptane wash. The thus combined organic phases were washed with 5% aqueous sodium chloride. The phases were separated and the aqueous phase washed with heptanes (0.2 L), then discarded. The organic phase was concentrated at reduced pressure which gave 440 g of crude product.

The procedure was repeated starting with 426.5 g of compound 2c which gave 473 g of crude product.

The combined crude products were dissolved in a mixture of heptanes and toluene (1.0 L, 2:1) and purified on a silica gel column prepared from silica gel 60 (2.25 kg) and heptanes/toluene 2:1 v/v. The column was eluted with: heptanes/toluene (2:1, 15 L). Fractions of ~1 L were collected and pure fractions of compound 2d were combined and concentrated at reduced pressure which gave the title compound (667.3 g, 75.1%).

Step e) (3S,4R,5R)-3-Chloro-3-fluoro-4-hydroxy-5-(hydroxymethyl)dihydrofuran-2(3H)-one (28e)

Compound 28d (613.0 g, 1.11 mol) was added to a 3 L glass reactor filled with nitrogen and methanol (1.2 L) and. To the stirred emulsion was added 37% hydrochloric acid (368.0 g, 3.73 mol, 3.4 eq.) and the mixture was heated to gentle reflux (73° C.). The mixture was kept at reflux for 20 hours then cooled to 15-20° C. and extracted with heptanes (4×600 mL). The residual methanolic solution was concentrated to dryness at reduced pressure using a water bath of 80-90° C., finally at p<35 mbar. Dioxane (600 mL) was added and distilled again as above, which gave the title compound (200.7 g, 98%).

Step f (2R,3R,4S)-4-chloro-4-fluoro-2-(((4-methylbenzoyl)oxy)methyl)-5-oxotetrahydrofuran-3-yl 4-methylbenzoate (28f)

A solution of compound 28e (200.7 g, 1.11 mol) in dioxane (1.4 L) in a 3 L glass reactor filled with nitrogen and equipped with mechanical stirring, thermometer and an addition funnel was heated to 40 to 45° C. on a water bath. p-Toluoyl chloride (360.5 g, 2.33 mol, 2.1 eq.) was added whereafter triethylamine (258.3 g, 2.55 mol, 2.3 eq.) was added during 35 minutes so as to keep the reaction temperature below 70° C. The resulting suspension was then stirred at 65° C. for 2 hours, then cooled to 15° C. and filtered. The 800 mL filter cake was washed with dioxane (800 mL, 15° C.), leaving a white filter cake which was discarded. The filtrate was concentrated at reduced pressure, finally at 35 mbar using a water bath of 65° C. 2-Propanol (1.50 L) was added to the residual oil (510 g) so as to keep the temperature of the solution at 40-45° C. The solution was seeded and carefully allowed to cool to room temperature. During the cooling process samples of 0.25 mL were taken and mixed with 0.25 mL of water for pH measurements. Triethylamine (15 g) was added until pH 2.5-3.5 was obtained. Once room temperature was reached (one hour), the crystal suspension was cooled to 10±1° C. and kept at this temperature for 15 hours. The title product was isolated by filtration, washed with 2-propanol (600 mL, 5-10° C.) and then dried at 30-50° C. in an air vented oven. Yield:

374.2 g, 80%. Purity (HPLC): 99.4%. Melting point: 88.0-89.5° C. (1° C./min) crystal form change and then melts at 97-98° C.

Step g) (2R,3R,4S)-4-Chloro-4-fluoro-5-hydroxy-2-(((4-methylbenzoyl)oxy)methyl)-tetrahydrofuran-3-yl 4-methylbenzoate (28g)

A 3 L reaction flask set up with mechanical stirrer, thermometer and an addition funnel was filled with nitrogen. The flask was charged with ethyl acetate (1000 g) and cooled to 10° C. Lithium tri-tert-butoxyaluminium hydride (30% solution in THF, 35 g, 0.05 eq.) was added. Stirring at 10° C. was continued for 5-10 minutes and then compound 28f (370.0 g, 0.88 mol) was added.

Further lithium tri-tert-butoxyaluminium hydride (30% solution in THF, 933.8 g, 1.10 mol, 1.25 eq.) was added over a period of 70 minutes while keeping the reaction temperature at 10° C. The reaction was quenched by pouring the reaction mixture onto a quench mixture (1.45 kg (10% NaCl-10% NH$_4$Cl in 3M HCl)) keeping the temperature at 10-15° C. The resulting suspension was warmed to 20-25° C. The aqueous was separated and discarded and the organic phase was washed with acidic water (1.0 L+10 mL of 3M HCl) followed by a wash with 25% sodium chloride (250 mL). The organic phase was concentrated to dryness, finally at p<35 mbar and 45° C. The residue was re-dissolved in toluene (0.45 kg) and the solution was again concentrated, at p<35 mbar and 45° C., which gave the title compound as an oil containing a little solid sodium chloride (412.6 g, 111%). Purity (HPLC) 97.5%.

Step h) (2R,3R,4S)-4,5-dichloro-4-fluoro-2-(((4-methylbenzoyl)oxy)methyl)tetrahydrofuran-3-yl 4-methylbenzoate (28 h)

A 2000 mL reaction flask set up for mechanical stirring, temperature measurement and condenser was filled with nitrogen and charged with toluene (740 mL), compound 28g (411.5 g, 0.88 mol) and thionyl chloride (174.0 g, 1.46 mol, 1.66 equivalents). The reaction flask was placed on a water bath, pre-heated to 50° C. and DMF (0.50 mL) was added. The top of the condenser was connected a cooled scrubber (700 g of 27.65% sodium hydroxide) and a steady flow of nitrogen was applied. The reaction started shortly after the DMF was added and it was followed by HPLC. After approximately three hours, the gas evolution has decreased and the temperature was increased to 60-65° C. Heating at 60-65° C. was continued for further 4.5 hours after which time the sulfite esters had vanished. The solvent and residual thionyl chloride was distilled off (500 mL) at reduced pressure using a water bath of 60-65° C. Toluene (650 mL) was added to the residual oil and the mixture was cooled to 5° C. Water (650 mL) was added and the pH was adjusted to 2.0-3.0 by addition of 3M sodium hydroxide (40 mL) at a temperature below 10° C. The temperature was adjusted to 20-22° C. and the aqueous phase was separated. The organic phase was washed with 25% sodium chloride (250 mL). The aqueous phases were back washed with toluene (250 mL). The combined organic phase was dried with magnesium sulfate (25 g) and filtered. Evaporation of the solvent (finally at p<35 mbar and 60° C.) provided the title compound as a light brown oil (378.5 g, 97% yield). Chlorobenzene (200 g) was added to the residue and the mixture was concentrated using the above conditions. The residue was again dissolved in chlorobenzene (200.0 g) and the mixture concentrated.

Step i) (2R,3R,4S,5R)-5-(4-Benzamido-2-oxo-3,4-dihydropyrimidin-1(2H)-yl)-4-chloro-4-fluoro-2-(((4-methylbenzoyl)oxy)methyl)tetrahydrofuran-3-yl 4-methylbenzoate (28i)

A 500 mL round bottom flask was charged with N-benzoylcytosine (36.6 g, 170 mmol, 1.5 eq.), chlorobenzene (165 g, 150 mL) and ammonium sulfate (0.45 g, 3.4 mmol, 0.03 eq.), to this suspension was added HMDS (29.3 g, 181.3 mmol, 1.6 eq.). The suspension was heated to reflux. When the reaction mixture became a clear solution, it was refluxed for additional 1 h and then concentrated by distillation in vacuo at 60° C. (distillate: 150 mL). Chlorobenzene (125 mL) was added to the residue.

Residual toluene in Compound 28h (50 g, 113.3 mmol) was removed by distillation in vacuo from chlorobenzene. The residue from this co-evaporation was dissolved in 1,2-dichloroethane (200 mL), and this solution was charged to the solution of silylated nucleoside in chlorobenzene. Tin(IV)chloride (59.0 g, 226.6 mmol, 2 eq.) was added and the mixture was heated to reflux under nitrogen. The reaction mixture was stirred at reflux for 65 h. The reaction mixture was cooled to 5° C., and ethyl acetate (99.8 g, 10 eq.) was added while keeping the temperature at 10-12° C. Total weight of mixture: 601.7 g. A quarter of this mixture (150.4 g, in theory 28.3 mmol) was charged to a 250 mL 3 necked round bottom flask, cooled to 5° C., and dichloromethane (147.5 g, 4×vol. of EtOAc) was added together with Celite (6.25 g). A warm (approx. 60° C.) 50% NaOH solution (17.6 g, 7.76 eq.) was added to the mixture in such a rate that the temperature was kept at 5-12° C. The mixture was stirred for 20 min at 10° C., then the temperature was adjusted to 25° C. and the mixture was stirred at this temperature for 30 min. The suspension was filtered on a pad of Celite (12.5 g) and the filter cake was washed with dichloromethane (190 mL). The combined filtrate and washings were concentrated to dryness by distillation in vacuo at 60° C. Dichloromethane (86 mL) was added to the residue then toluene (62 mL). The content of dichloromethane was removed by distillation in vacuo at 50° C. The resulting suspension was stirred at room temperature for 17 h whereafter the crude title compound was isolated by filtration. The filter cake was washed with toluene (25 mL) and the wet product was dried in an air ventilated dryer at 40° C., which gave title compound as a solid (5.56 g, 31.7%).

Step j) (2R,3R,4S,5R)-4-Chloro-5-(2,4-dioxo-3,4-dihydropyrimidin-1(2H)-yl)-4-fluoro-2-(((4-methylbenzoyl)oxy)methyl)tetrahydrofuran-3-yl 4-methylbenzoate (28j)

Compound 28i (15.2 g 24.5 mmol) was suspended in 65% AcOH/water (152 mL, v/v), and the suspension was heated to reflux for 20 h. The reaction mixture was allowed to cool to room temperature, then water (53 mL) was added and the mixture was stirred at room temperature for 1.5 h. The suspension was filtrated and the filter cake washed with water (2×25 mL). The wet filter cake was dried in an air ventilated dryer at 40° C. for 20 h, which gave the title compound as a solid (10.8 g, 85%).

Step k) 1-((2R,3S,4R,5R)-3-Chloro-3-fluoro-4-hydroxy-5-(hydroxymethyl)tetrahydrofuran-2-yl)pyrimidine-2,4(1H,3H)-dione (28k)

Compound 28j (8.0 g, 15.5 mmol) was suspended in MeOH (80 mL), n-propylamine (9.1 g, 154.8 mmol, 10 eq.) was added and the mixture was heated to 30° C. and stirred at this temperature for 24 h. The solvents were removed by distillation in vacuo at 40° C. The residue was taken up in water (20 mL), the aqueous phase was washed with DCM (3×40 mL) and the combined organic phases were washed with water (5 mL). The two aqueous phases were combined, and pH adjusted to 1.0 with 3 M HCl (approx. 7 mL). The acidic aqueous phase was extracted with Me-THF (4×40 mL), and the combined organic phases were concentrated to dryness by distillation in vacuo at 40° C. Isopropyl acetate (80 mL) was added to the residue, and the turbid mixture was concentrated in vacuo at 60° C. Isopropyl acetate (40 mL) was added and the distillation in vacuo was continued. Isopropyl acetate (10 mL) was added to the resulting thick suspension. The suspension was cooled to room temperature and stirred for 30 min. Crude title compound was collected by filtration, and the filter cake was washed with isopropyl acetate (2×4 mL). The afforded crude was dissolved in Me-THF (35 mL), isopropyl acetate (70 mL) was added and the mixture was concentrated by distillation in vacuo at 60° C. (distillate: 70 mL). Additional isopropyl acetate (30 mL) was added, and the distillation was continued (distillate: 30 mL). The suspension was cooled to room temperature, stirred at for 45 min and then filtered. The filter cake was washed with isopropyl acetate (2×4 mL) then dried in vacuo at room temperature. The title compound was isolated in 70% yield (3.0 g). Purity (HPLC) 98.5%.

Step l) (S)-Isopropyl 2-(((S)-(((2R,3R,4S,5R)-4-chloro-5-(2,4-dioxo-3,4-dihydropyrimidin-1(2H)-yl)-4-fluoro-3-hydroxytetrahydrofuran-2-yl)methoxy)(phenoxy)phosphoryl)amino)propanoate (28)

THF (0.07% water, 12 mL) was added to Compound 28k (500 mg, 1.78 mmol) and the solution was cooled to −10° C. under nitrogen. Tert-butylmagnesium chloride, 20% wt in THF (2.20 g, 3.74 mmol, 2.1 eq.) was added by syringe over 20 min at −10° C. The syringe was rinsed with 500 μL THF and the rinse was added to the reaction mixture. The formed suspension was stirred at −10° C. for 40 min. A solution of (S)-isopropyl 2-(((S)-(perfluorophenoxy)(phenoxy)phosphoryl)-amino)propanoate (1.01 g, 2.23 mmol, 1.25 eq.) in THF (10 mL) and DMPU (2.0 mL, 16.9 mmol, 9.5 eq.) was added with a syringe at −10° C. over a period of 87 min whereafter the reaction mixture was stirred at −10° C. for 22 h. The reaction was quenched by addition of 1 M HCl (4.6 mL, 2.6 eq.) while keeping the temperature below 5° C. Toluene (20 mL) was added and the mixture was heated to 25° C. and stirred at this temperature for 5 min. The phases were separated and the aqueous phase was extracted with toluene/THF (1:1, 10 mL). The organic phases were washed with 1 M HCl (2×10 mL) and 5% $Na_2CO_3$ (2×10 mL). The combined basic aqueous phases were extracted with toluene (1×10 mL) and toluene/THF (1:1, 2×10 mL) and the combined organic phases were washed with 25% NaCl (15 mL). All organic phases were then combined and the solvents removed by distillation in vacuo at 60° C. 2-Propanol (20 mL) and n-heptane (30 mL) was added to the residue and the suspension was cooled to 5° C. overnight. The suspension was filtered and the filtrate was concentrated by distillation in vacuo at 50° C. The residue was dried on a pump for 3 h which gave the title compound as a single stereoisomer at the phosphorus atom as a foam (874 mg, 89%). Purity (HPLC) of crude 91.8%.

NMR spectra obtained for compound 28 prepared in Example 28 were in agreement with spectral data of compound 2 prepared in Example 2.

NMR data for a selection of the exemplified compounds:
Compound 5
$^1$H NMR (500 MHz, DMSO) δ 0.81 (t, 3H), 1.12 (d, 3H), 1.24 (d, 3H), 1.49 (dh, 2H), 3.83 (tq, 1H), 4.03 (m, 1H), 4.30 (m, 3H), 4.71 (h, 1H), 5.60 (d, 1H), 6.11 (dd, 1H), 6.24 (d, 1H), 7.20 (dd, 4H), 7.37 (t, 2H), 7.56 (d, 1H).
$^{13}$C NMR (126 MHz, DMSO) δ 172.59, 172.55, 162.84, 162.82, 150.55, 150.50, 150.21, 129.54, 124.49, 119.96, 119.92, 115.02, 113.01, 102.29, 78.79, 74.45, 74.31, 72.22, 64.31, 49.72, 40.28, 40.24, 39.99, 39.90, 39.82, 39.73, 39.66, 39.57, 39.49, 39.40, 39.23, 39.07, 38.90, 27.98, 19.70, 19.65, 18.93, 9.30, 0.00.
Compound 9
$^1$H NMR (500 MHz, DMSO-$d_6$) δ 7.55 (d, J=7.8 Hz, 1H), 6.87 (d, J=8.4 Hz, 1H), 6.84 (d, J=1.7 Hz, 1H), 6.76-6.60 (m, 2H), 6.32-6.19 (m, 1H), 6.10-6.01 (m, 1H), 6.02 (s, 2H), 5.62 (d, J=8.1 Hz, 1H), 4.86 (p, J=6.3 Hz, 1H), 4.37-4.15 (m, 4H), 4.07-3.97 (m, 1H), 3.79 (tq, J=10.1, 7.1 Hz, 2H), 1.23 (d, J=7.1 Hz, 3H), 1.16 (d, J=6.3 Hz, 5H).
$^{13}$C NMR (126 MHz, DMSO-$d_6$) δ 172.50, 147.46, 144.86, 144.81, 143.91, 115.06, 115.05, 113.05, 113.05, 112.41, 112.40, 112.37, 112.37, 107.88, 102.36, 102.34, 101.52, 78.74, 74.44, 74.30, 67.90, 64.28, 49.65, 40.63, 40.40, 40.34, 40.27, 39.99, 39.90, 39.83, 39.73, 39.66, 39.57, 39.40, 39.23, 39.07, 38.90, 21.28, 21.26, 19.72, 19.67, −0.00.
Compound 10
$^1$H NMR (500 MHz, DMSO-$d_6$) δ 7.58 (d, J=8.1 Hz, 1H), 7.28 (d, J=8.0 Hz, 1H), 7.20-7.05 (m, 2H), 6.90 (td, J=7.9, 1.6 Hz, 1H), 5.60 (d, J=8.1 Hz, 1H), 4.87 (dq, J=12.5, 6.2 Hz, 1H), 4.41-4.20 (m, 5H), 4.09-3.99 (m, 1H), 4.00-3.77 (m, 2H), 3.79 (s, 3H), 1.79 (s, 1H), 1.22 (d, J=7.1 Hz, 3H), 1.16 (d, J=6.3 Hz, 5H).
$^{13}$C NMR (126 MHz, DMSO-$d_6$) δ 172.59, 172.55, 162.64, 150.28, 150.24, 150.09, 139.37, 139.32, 125.29, 120.90, 120.88, 120.25, 115.03, 113.02, 112.85, 102.25, 78.82, 74.38, 74.24, 67.85, 64.26, 55.59, 49.57, 40.26, 40.20, 40.17, 39.99, 39.90, 39.82, 39.73, 39.66, 39.57, 39.40, 39.23, 39.07, 38.90, 21.30, 21.26, 19.63, 19.58.
Compound 11
$^1$H NMR (500 MHz, DMSO-$d_6$) δ 7.57 (d, J=8.1 Hz, 1H), 7.13 (d, J=8.3 Hz, 2H), 6.98-6.86 (m, 3H), 6.25 (t, J=16.6 Hz, 1H), 5.62 (d, J=8.1 Hz, 1H), 4.86 (hept, J=6.2 Hz, 1H), 4.37-4.15 (m, 4H), 4.07-3.97 (m, 1H), 3.78 (tq, J=10.2, 7.1 Hz, 1H), 3.72 (s, 2H), 1.23 (d, J=7.1 Hz, 3H), 1.22-1.11 (m, 8H).

$^{13}$C NMR (126 MHz, DMSO-d$_6$) δ 172.52, 172.48, 162.65, 155.91, 150.08, 143.96, 143.91, 120.95, 120.92, 114.99, 114.42, 112.98, 102.27, 78.77, 74.44, 74.30, 67.86, 64.21, 55.29, 49.65, 40.25, 40.15, 39.99, 39.90, 39.83, 39.74, 39.66, 39.57, 39.40, 39.24, 39.07, 38.90, 21.30, 21.27, 19.69, 19.64.

Compound 13

$^1$H NMR (500 MHz, DMSO-d$_6$) δ 0.82 (t, 3H), 1.12 (d, 3H), 1.25 (d, 3H), 1.49 (m, 2H), 3.83 (dtd, 1H), 4.02 (m, 1H), 4.26 (dt, 2H), 4.34 (m, 1H), 4.72 (h, 1H), 5.58 (d, 1H), 6.12 (dd, 1H), 6.26 (m, 1H), 7.20 (m, 3H), 7.37 (t, 2H), 7.53 (d, 1H).

$^{13}$C NMR (126 MHz, DMSO-d$_6$) δ 9.35, 19.05, 19.77 (d), 28.00, 40.08, 49.72, 64.32, 72.27, 74.35 (d), 78.72 (m), 102.36, 114.08 (d), 119.95 (d), 124.49, 129.54, 150.53 (d), 163.41 (m), 172.62 (d).

Compound 15

$^1$H NMR (500 MHz, DMSO-d$_6$) δ 1.16 (d, 6H), 1.24 (d, 3H), 1.80 (m, 1H), 1.96 (m, 1H), 2.05 (pdd, 2H), 2.26 (m, 2H), 3.49 (p, 1H), 3.81 (tq, 1H), 4.04 (m, 1H), 4.30 (m, 3H), 4.86 (hept, 1H), 5.60 (d, 1H), 6.07 (dd, 1H), 6.24 (d, 1H), 6.68 (d, 1H), 7.03 (m, 3H), 7.28 (t, 1H), 7.58 (d, 1H).

$^{13}$C NMR (126 MHz, DMSO-d$_6$) δ 17.58, 19.65 (d), 21.26, 21.29, 29.13, 49.65, 64.33, 67.87, 74.37 (d), 78.78, 102.28, 113.98 (d), 117.35 (d), 117.76 (d), 122.45, 129.25, 139.49, 147.50, 150.05, 150.56, 162.56, 172.48 (d).

Compound 16

$^1$H NMR (500 MHz, DMSO-d$_6$) δ 0.78 (m, 8H), 1.15 (d, 12H), 1.23 (d, 7H), 1.35 (s, 6H), 3.80 (tq, 2H), 4.03 (m, 2H), 4.25 (m, 4H), 4.34 (m, 2H), 4.86 (p, 2H), 5.59 (d, 2H), 6.07 (dd, 2H), 6.24 (d, 2H), 6.72 (s, 1H), 7.01 (m, 6H), 7.26 (t, 2H), 7.57 (d, 2H).

$^{13}$C NMR (126 MHz, DMSO-d$_6$) δ 16.03, 18.82, 19.65 (d), 21.26, 21.30, 24.42, 49.63, 64.29, 67.87, 74.35 (d), 78.78, 87.51, 102.30, 114.00 (d), 116.92 (d), 117.60 (d), 122.06, 129.18, 139.60 (m), 148.45, 150.13, 150.50 (d), 162.69, 172.47 (d).

Compound 17

$^{13}$C NMR (126 MHz, DMSO-d$_6$) δ 15.52, 18.66, 19.65 (d), 21.25, 21.30, 24.98, 49.67, 64.23, 67.87, 74.35 (d), 78.76, 87.49, 102.25, 113.97 (d), 119.69 (d), 127.19, 139.65 (d), 142.69, 148.17 (d), 150.02, 162.52, 172.46 (d).

Compound 21

$^1$H NMR (500 MHz, DMSO) δ 1.25 (d, 3H), 3.23 (m, 6H), 3.41 (m, 4H), 3.87 (ddt, 1H), 4.04 (m, 1H), 4.31 (m, 3H), 5.02 (p, 1H), 5.61 (d, 1H), 6.20 (m, 2H), 7.21 (m, 3H), 7.38 (t, 2H), 7.57 (d, 1H).

$^{13}$C NMR (126 MHz, DMSO) δ 19.72 (d), 49.60, 58.36, 64.28, 70.33, 70.46, 71.53, 74.38 (d), 78.81 (d), 102.26, 114.00 (d), 119.99 (d), 124.53, 129.55, 150.03, 150.51 (d), 162.54, 172.59 (d).

Compound 24

$^1$H NMR (500 MHz, DMSO) δ 1.15 (dd, 6H), 1.22 (d, 3H), 3.52 (m, 1H), 3.78 (tq, 1H), 4.05 (m, 1H), 4.16 (m, 1H), 4.26 (dt, 1H), 4.34 (m, 1H), 4.86 (hept, 1H), 5.65 (d, 1H), 6.14 (dd, 1H), 6.23 (m, 1H), 6.27 (s, 1H), 7.21 (m, 3H), 7.37 (t, 2H), 7.50 (d, 1H).

$^{13}$C NMR (126 MHz, DMSO) δ 19.62 (d), 21.25 (d), 49.61, 63.83, 67.92, 74.16 (d), 78.53, 102.42, 114.03 (d), 119.85 (d), 124.49, 129.58, 139.35 (dd), 150.26, 150.56 (d), 162.87, 172.51 (d).

Compound 26b $^1$H NMR (500 MHz, DMSO) δ 3.62 (d, 1H), 3.80 (m, 2H), 4.15 (dd, 1H), 5.26 (s, 1H), 5.77 (d, 1H), 6.31 (d, 1H), 6.41 (s, 1H), 7.33 (s, 1H), 7.36 (s, 1H), 7.73 (d, 1H).

$^{13}$C NMR (126 MHz, DMSO) δ 58.50, 58.62, 73.62 (d), 80.48, 87.01 (m), 94.50, 94.56, 114.92 (d), 140.04, 154.57, 165.42.

Compound 27d $^1$H NMR (500 MHz, D2O) δ 4.12 (d, 1H), 4.24 (ddd, 1H), 4.33 (m, 1H), 4.46 (dd, 1H), 6.09 (d, 1H), 6.39 (d, 1H), 7.80 (d, 1H).

$^{13}$C NMR (126 MHz, D2O) δ 62.48 (d), 73.03 (d), 78.99 (d), 88.15 (d), 97.04, 113.71 (d), 140.63, 157.39, 166.21.

BIOLOGICAL EXAMPLES

Replicon Assay

The compounds of formula I may be examined for activity in the inhibition of HCV RNA replication in a cellular assay aimed at identifying compounds that inhibit a HCV functional cellular replicating cell line, also known as HCV replicons. A suitable cellular assay is based on a bicistronic expression construct, as described by Lohmann et al. (1999), Science vol. 285 pp. 110-113 with modifications described by Krieger et al. (2001), Journal of Virology 75: 4614-4624, in a multi-target screening strategy.

The assay utilizes the stably transfected cell line Huh-7 luc/neo (hereafter referred to as Huh-Luc). This cell line harbors an RNA encoding a bicistronic expression construct comprising the wild type NS3-NS5B regions of HCV type 1b translated from an Internal Ribosome Entry Site (IRES) from encephalomyocarditis virus (EMCV), preceded by a reporter portion (FfL-luciferase), and a selectable marker portion (neo$^R$, neomycine phosphotransferase). The construct is bordered by 5' and 3' NTRs (non-translated regions) from HCV type 1b. Continued culture of the replicon cells in the presence of G418 (neo$^R$) is dependent on the replication of the HCV RNA. The stably transfected replicon cells that express HCV RNA, which replicates autonomously and to high levels, encoding inter alia luciferase, are used for screening the antiviral compounds.

The replicon cells are plated in 384 well plates in the presence of the test and control compounds which are added in various concentrations. Following an incubation of three days, HCV replication is measured by assaying luciferase activity (using standard luciferase assay substrates and reagents and a Perkin Elmer ViewLux™ ultraHTS microplate imager). Replicon cells in the control cultures have high luciferase expression in the absence of any inhibitor. The inhibitory activity of a compound on luciferase activity is monitored on the Huh-Luc cells, enabling a dose-response curve for each test compound. EC$_{50}$ values are then calculated, which value represents the amount of the compound required to decrease the level of detected luciferase activity by 50%, or more specifically, the ability of the genetically linked HCV replicon RNA to replicate.

Enzyme Assay

As may be demonstrated in the replicon assay, the compounds of the invention are metabolised by cellular kinases in target tissues to the 5'-trisphosphate. It is this triphosphate which is believed to be the antivirally active species. The enzyme assay described here may be used to confirm that compounds of the invention are antivirally active as the 5'-triphosphate metabolite.

The enzyme assay measures the inhibitory effect of triphosphate compounds in an HCV NS5B-21 (21-amino-acid C-terminally truncated version) SPA assay (scintillation proximity assay). The assay is performed by evaluating the amount of radiolabelled ATP incorporated by HCV NS5B-21 into newly synthesized RNA using an heterogeneous biotinylated RNA template.

To determine $IC_{50}$ values the compounds are tested at various concentrations in a final volume of 100 µl of reaction mixture. The reaction is stopped by addition of 0.5M EDTA solution.

The samples are transferred into flashplates precoated with streptavidin. The incorporated radioactivity is quantified using a scintillation counter (Wallac Microbeta Trilux).

| Materials & Supplier | |
|---|---|
| Flashplate coated with streptavidin | Perkin Elmer Life Sciences |
| 96 well polypropylene plate | Corning |
| Biotinylated RNA template: with a sequence of 5'-UUU UUU UUU UAG UCA GUC GGC CCG GUU UUC CGG GCC-3' (SEQ ID NO: 1) and biotinylated at the 5'-primer end made up to 83 µM in 10 mM Tris-HCl, 100 mM NaCl, pH = 8.0 | Medprobe |
| Enzyme: HCV NS5B-21, made up to 500 µg/ml in water. | Replizyme |
| Nucleotides: GTP, CTP, UTP | Invitrogen |
| Radiolabelled $^3$H-ATP (cat. no TRK747) | GE Healthcare |
| 0.5M EDTA, pH = 8.0 | Life Technologies |
| Tris-HCl | Sigma |
| $MnCl_2$ | Sigma |
| Ammonium acetate | Sigma |
| DTT (dithiothreitol) | Sigma |
| CHAPS | Sigma |
| RNase Out (cat. No 10777-019) | Invitrogen |
| DMSO | Carlo Erba Reactifs - SDS |
| Equipment | |
| Wallac Microbeta Trilux | Perkin Elmer Life Sciences |
| Method | |
| Assay conditions | |
| Buffer: 20 mM tris-HCl, 100 mM ammonium acetate, 20 mM NaCl, 2.5 mM $MnCl_2$, 10 mM DTT, 2 mM CHAPS, RNase Out | pH 7.5 |
| GTP | 50 µM |
| CTP | 2 µM |
| UTP | 2 µM |
| ATP | 2 µM |
| $^3$H-ATP (47 Ci/mmol) | 0.5 µM |
| Template: RNA-H3 | 83 nM |
| Enzyme: NS5B-21 (500 µg/ml) | 2 µg/ml |
| Assay volume | 100 µl |

The assay should include enzyme controls (about four, containing 1 µl DMSO instead of inhibitor) and background control containing all ingredients except template.

Compounds are serially diluted in DMSO on a separate dilution plate to 100× the final desired assay concentrations.

Sufficient reaction mixture for the number of wells to be used is made up according to the table below and 90 µl/well is added to a 96 well polyproylene plate. 1 µl of compound in DMSO from the dilution plate is added to each well, except the enzyme control wells and background control wells to which 1 µl DMSO is added.

| Reaction mixture | |
|---|---|
| Component | µl/well |
| 50 mM tris-HCl pH = 7.5 | 40 |
| 1M Ammonium acetate | 10 |
| 1M $MnCl_2$ | 0.25 |
| 0.5M DTT | 2 |
| 100 mM CHAPS | 2 |
| RNase Out | 0.2 |
| 1 mM GTP | 5 |
| 200 µM CTP + UTP | 2 |
| NS5B-21 500 µg/ml | 0.4 |
| Template: RNA-H3, 83 µM | 0.1 |
| Template buffer: 10 mM tris-HCl, 100 mM NaCl pH = 8.0 | 28.25 |

Prepare an ATP cocktail containing 1.5 of $^3$H-ATP (45 Ci/mmol), 2.0 µl/well of 100 µM ATP and 6.5 µl/well of $H_2O$ and start the reaction by adding 10 µl/well of this cocktail.

Incubate at 22° C. for 120 min.

Stop the reaction with the addition of 100 µl/well of 0.5M EDTA, pH=8.0.

Transfer 185 µl/well to the streptavidin flash plate.

Incubate the plate over night and read the flash plate in the Microbeta Trilux using the protocol Flash plates H3.

Treatment of Results

Calculation for Inhibition:

% Inhibition=CompoundCPM−BackgroundCPM/
AverageEnzymeControlCPM−BackgroundCPM

Background=Reaction buffer without template.

$IC_{50}$ is determined using Graphpad Prism. Plot Compound concentration in Log versus percentage inhibition. Fit the curve with nonlinear regression to the Log (Inhibitor) versus Response equation.

$$Y = \text{Bottom} + \frac{\text{Top} - \text{Bottom}}{1 + 10^{(X-\log(IC_{50}))}}$$

Where Y is % Inhibition, X is log (inhibitor) and top and bottom are the upper and lower limits of the % Inhibition.

Biological Example 1

The inhibition of HCV replication exhibited by the compounds of the invention were tested in the above described replicon assay. The compounds showed sub micromolar activity, with a cell toxicity in the Huh-Luc cell line being in excess of 50 µM. The $EC_{50}$ values are presented in Table 1.

TABLE 1

| Example | $EC_{50}$ (µM) |
|---|---|
| 1 | >50 |
| 2 | 0.055 |

TABLE 1-continued

| Example | $EC_{50}$ (μM) |
| --- | --- |
| 4 | 0.090 |
| 5 | 0.043 |
| 6 | 0.079 |
| 7 | 0.055 |
| 8 | 0.044 |
| 9 | 0.19 |
| 10 | 0.045 |
| 11 | 0.15 |
| 12 | 0.18 |
| 13 | 0.061 |
| 14 | 0.076 |
| 15 | 0.090 |
| 16 | 0.091 |
| 17 | 0.11 |
| 20 | 0.065 |
| 21 | 0.21 |
| 22 | 0.058 |
| 23 | 5.1 |
| 24 | 1.4 |
| 25 | 0.1 |
| 26 | 0.086 |

Biological Example 2

The nucleotides of Examples 3 and 27 were tested in the above described enzyme assay and the $IC_{50}$ values determined to be 0.72 μM and 0.089 μM respectively.

Comparative Example 1

Sofosbuvir is marketed in several countries for the treatment of HCV, predominantly against genotypes 1 and 4. The structure of sofosbuvir is:

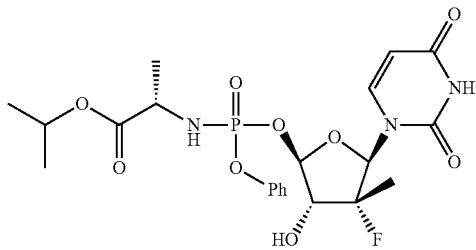 [SMILES: CC(C)OC(=O)[C@H](C)NP(=O)(Oc1ccccc1)O[C@H]1O[C@@H](n2ccc(=O)[nH]c2=O)[C@](C)(F)[C@@H]1O]

As can been seen, sofosbuvir differs from the compound of present Example 2, in that it possesses a beta-methyl group at the 2'-position, whereas the compounds of the invention have a beta-chloro substituent at this position. In the Fission phase III clinical trials reported in Lawitz et al., N. Eng. J. Med., 2013; 368:1878-87, "Response rates in the sofosbuvir-ribavirin group were lower among patients with genotype 3 infection than amongst those with genotype 2 infection (56% vs. 97%)".

The antiviral activity of commercially available sofosbuvir and the compound of Example 2 were compared in a genotype 3a transient replicon assay described in Kylefjord et al., J Virol. Methods 2014 195:156-63.

The $EC_{50}$ of sofosbuvir against genotype 3a is 0.230 μM+/−0.067, n=11, compared to an $EC_{50}$ of 0.072 μM+/−0.024, n=9 for the compound of Example 2. A threefold better potency for the compound of the invention relative to sofosbuvir is expected to markedly improve viral response rates in the clinic.

The several-fold improvement in potency of the compounds of the invention relative to sofosbuvir was maintained in transient replicons of genotype 3a bearing the troublesome S282T mutation (conferring resistance to the HCV nucleoside mericitabine) where sofosbuvir had an $EC_{50}$ of 0.48 μM (n=1) and the compound of Example 2 had an $EC_{50}$ of 0.13 μM (n=1). Similarly, the L159F/L320F double mutant generated by exposure to the nucleoside mericitabine and conferring cross resistance to sofosbuvir (Tong et al 2013 J. Infect. Dis., 209 (5), 668-75) was prepared in a genotype 3a transient replicon as described above in Kylefjord et al. ibid. In the this double mutant, sofosbuvir had an $EC_{50}$ of 0.190 (n=1) whereas the compound of Example 2 shows an $EC_{50}$ of 0.062 (n=1).

The compound of Example 2 was further evaluated to assess the antiviral activity against genotypes 1-6 of HCV, both wild type and a number of clinically relevant mutant strains. The result of the evaluation together with the average $EC_{50}$ of the genotypes and the corresponding values for sofosbuvir are summarised in Tables 2 and 3.

TABLE 2

| Wild Type | | |
| --- | --- | --- |
| HCV Assay | sofosbuvir | Cmpd of Ex. 2 |
| HCV GT1b (stable) | 0.098 (n = 126) | 0.045 (n = 63) |
| HCV GT1b (transient) | 0.081 (n = 31) | 0.044 (n = 22) |
| HCV GT1a* | 0.131 (n = 16) | 0.050 (n = 16) |
| HCV GT2a replicon | 0.048 (n = 2) | 0.023 (n = 2) |
| HCV GT2a virus | 0.054 (n = 4) | 0.017 (n = 3) |
| HCV GT3a* | 0.129 (n = 8) | 0.046 (n = 8) |
| HCV GT4a* | 0.218 (n = 8) | 0.059 (n = 8) |
| HCV GT5a* | 0.114 (n = 5) | 0.044 (n = 8) |
| HCV GT6a* | 0.179 (n = 4) | 0.058 (n = 6) |
| AVG $EC_{50}$: | 0.117 +/− 0.019 | 0.043 +/− 0.005 |
| (potency increase vs sofosbuvir) | 1.0 | 2.7 |

$EC_{50}$ data (all in μM) presented as geometric means except AVG where the $EC_{50}$ is presented as the arithmetic means +/− SEM.
*Chimeric replicons containing stated GT NS5B genes in con1 background.
References: Con1 (Lohmann et al 2003); H77 (Blight et al 2003); GT2a (Wakita et al 2005); GT3a (Kylefjord et al 2013); GT4-6 (Wong et al 2012); L159F/L320F (Tong et al 2013).

TABLE 3

| Mutants | | |
| --- | --- | --- |
| HCV Assay | sofosbuvir | Cmpd of Ex. 2 |
| HCV GT1b S282T | 0.741 (n = 18) | 0.298 (n = 9) |
| FC vs WT | 8.8 | 6.8 |
| HCV GT1b L159F/L320F | 0.199 (n = 5) | 0.070 (n = 5) |
| FC vs WT | 2.5 | 1.6 |
| HCV GT1a* S282T | 1.01 (n = 5) | 0.301 (n = 5) |
| FC vs WT | 7.7 | 6.0 |
| HCV GT3a* S282T | 0.521 (n = 6) | 0.122 (n = 6) |
| FC vs WT | 4.0 | 2.7 |
| HCV GT3a* L159F/L320F | 0.190 (n = 1) | 0.062 (n = 1) |
| FC vs WT | 1.5 | 1.3 |
| AVG $EC_{50}$ | 0.532 +/− 0.158 | 0.171 +/− 0.054 |
| (potency increase vs sofosbuvir) | 1.0 | 3.1 |

$EC_{50}$ data (all in μM) presented as geometric means except AVG where the $EC_{50}$ is presented as the arithmetic means +/− SEM.
*Chimeric replicons containing stated GT NS5B genes in con1 background.
References: Con1 (Lohmann et al 2003); H77 (Blight et al 2003); GT2a (Wakita et al 2005); GT3a (Kylefjord et al 2013); GT4-6 (Wong et al 2012); L159F/L320F (Tong et al 2013).

From these two tables it is evident that the compound of present Example 2 has a significant improved potency as compared to sofosbuvir against HCV GT3a both in the wild type strain and in two clinically relevant mutant strains, while keeping the good potency against the other genotypes.

Triphosphate Formation Assay

To estimate the ability of the compounds of the invention to generate the antivirally active triphosphate species, a triphosphate formation assay was conducted. Each compound was tested in triplicates in the assay.

Fresh human plated hepatocytes (Biopredic, France) in 12-well plates were used. Each well was plated with 0.76× $10^6$ cells and incubated with a 10 μM DMSO solution of compound (0.1% DMSO) in 1 mL incubation medium in a $CO_2$ incubator at 37° C. for 6-8 hours. The incubation was stopped by washing each well with 1 mL ice cold Hank's balanced solution, pH 7.2 twice, followed by addition of 0.5 mL ice cold 70% methanol Immediately after the addition of methanol, the cell-layer was detached from the bottom of the well by a cell scraper and sucked up and down 5-6 times with an automatic pipet. The cell suspension was transferred to a glass vial and stored over night at −20° C.

The samples, each consisting of various levels of protide, free nucleoside, and mono-, di- and triphosphate were then vortexed and centrifuged at 10° C. for 10 minutes, at 14000 rpm in an Eppendorf centrifuge 5417R. The supernatants were transferred to 2 mL glass vials with insert and subjected to bioanalysis.

Bioanalysis

An internal standard (Indinavir) was added to each sample and the samples (10 μL injection volume) were analysed on a two column system coupled to a QTRAP 5000 mass spectrometer. The two column system consisted of two binary pumps, X and Y, two switching valves and an autosampler. The two HPLC columns used were a Synergy POLAR-RP 50*4.6 mm, 4 μm particles and a BioBasic AX 50*2.1 mm 5 μm particles. The LC flow rates were 0.4-0.6 mL/min (the higher flow rate were used in the recondition step).

The HPLC mobile phases for the POLAR-RP column consisted of 10 mmol/L ammonium acetate in 2% acetonitrile (mobile phase A) and 10 mmol/L ammonium acetate in 90% acetonitrile (mobile phase B) and for the BioBasic AX column 10 mmol/L ammonium acetate in 2% acetonitrile (mobile phase C) and 1% ammonium hydroxide in 2% acetonitrile (mobile phase D). The HPLC gradient for pump Y started at 0% mobile phase B and was held for 2 min. During loading phase, the mobile phase went through the POLAR-RP and BioBasic AX column, and prodrug, nucleoside and internal standard were trapped on the POLAR-RP column; whereas the nucleotides (mono-, di- and triphosphates) eluted on to the BioBasic AX column and were trapped there.

In the next step, the flow was switched from the POLAR-RP column to the MS and the mobile phase C switched from pump X to the BioBasic AX column. The compounds on the POLAR-RP column were eluted with a gradient from 0% B up to 100% B in about two minutes and analyzed in positive or negative mode using the multiple reaction monitoring mode (MRM).

In the last step the flow from the BioBasic AX column was switched to the MS and the phosphates were eluted with a of about 7 minutes gradient up 50% D) and analyzed in positive or negative mode using MRM. During the last step both columns are reconditioned.

Triphosphate concentration for each compound was then determined by comparison with standard curves. The standard curves were made by analysis of standard samples with known concentrations of triphosphate. The standards were ran in the same matrices as the test samples. Due to variations in phosphorylation levels depending on hepatocyte donor, an internal reference compound is required in each run of the assay in order to enable ranking the results from different runs to each other.

Throughout the specification and the claims which follow, unless the context requires otherwise, the word 'comprise', and variations such as 'comprises' and 'comprising', will be understood to imply the inclusion of a stated integer, step, group of integers or group of steps but not to the exclusion of any other integer, step, group of integers or group of steps.

All documents referred to herein, including patents and patent applications, are incorporated by reference in their entirety.

The invention claimed is:
1. A compound represented by formula:

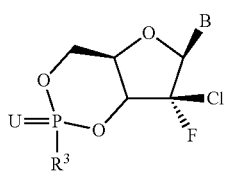

wherein:
B is a nucleobase selected from the groups (a) to (d):

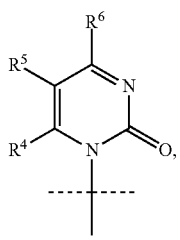
(a)

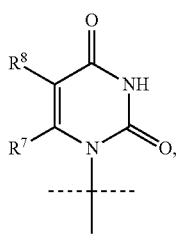
(b)

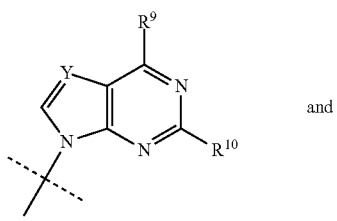
and
(c)

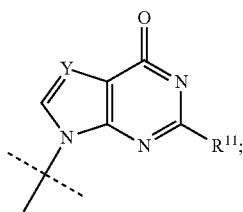
(d)

wherein Y is N or —C($R^{19}$)—;
$R^3$ is OH, $C_1$-$C_6$alkoxy, $C_3$-$C_7$cycloalkoxy, $C_3$-$C_7$cycloalkyl$C_1$-$C_3$alkoxy, benzyloxy, O—($C_1$-$C_6$alkylene)-T-$R^{21}$ or NHC($R^{15}$)($R^{15'}$)C(=O)$R^{16}$;
$R^4$, $R^5$, $R^7$ and $R^8$ are each independently H, $C_1$-$C_6$alkyl, $C_1$-$C_6$haloalkyl, $C_1$-$C_6$hydroxyalkyl, halo, —O$R^{18}$, —S$R^{18}$ or —N($R^{18}$)$_2$;
$R^6$, $R^9$, $R^{10}$, $R^{11}$ are each independently selected from H, $C_1$-$C_6$alkyl, $C_2$-$C_6$alkenyl, $C_2$-$C_6$alkynyl, $C_3$-$C_7$cycloalkyl, $C_1$-$C_6$haloalkyl, $C_1$-$C_6$hydroxyalkyl, halo, O$R^{18}$, S$R^{18}$, N($R^{18}$)$_2$, —NHC(O)O$R^{18}$, —NHC(O)N($R^{18}$)$_2$, —CN, —NO$_2$, —C(O)$R^{18}$, —C(O)O$R^{18}$, —C(O)N($R^{18}$)$_2$ and —NHC(O)$R^{18}$, wherein said $C_2$-$C_6$alkenyl group and said $C_2$-$C_6$alkynyl group can be optionally substituted with halo or $C_3$-$C_5$cycloalkyl;
$R^{16}$ is H, $C_1$-$C_{10}$alkyl, $C_2$-$C_{10}$alkenyl, $C_3$-$C_7$cycloalkyl, $C_3$-$C_7$cycloalkyl$C_1$-$C_3$alkyl, benzyl, phenyl or adamantyl, any of which is optionally substituted with 1, 2 or 3 groups, each independently selected from halo, O$R^{18}$ and N($R^{18}$)$_2$;
each $R^{18}$ is independently H, $C_1$-$C_6$alkyl, $C_1$-$C_6$haloalkyl or $C_3$-$C_7$cycloalkyl;
each $R^{21}$ is independently H, $C_1$-$C_{24}$alkyl, $C_1$-$C_6$haloalkyl, $C_1$-$C_6$hydroxyalkyl, $C_2$-$C_6$alkenyl, $C_2$-$C_6$alkynyl, $C_3$-$C_7$cycloalkyl or $C_3$-$C_7$cycloalkenyl;
U is O or S;
each T is independently —S—, —O—, —SC(O)—, —C(O)S—, —SC(S)—, —C(S)S—, —OC(O)—, —C(O)O— and —OC(O)O—;
or a pharmaceutically acceptable salt and/or solvate thereof.

2. The compound according to claim 1, wherein B is the group (a'):

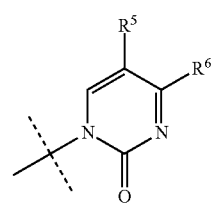
(a')

wherein
$R^5$ is H or F, and $R^6$ is N($R^{18}$)$_2$ or NHCO$C_1$-$C_6$alkyl.

3. The compound according to claim 2, wherein $R^6$ is NH$_2$.

4. The compound according to claim 1, wherein B is the group (b'):

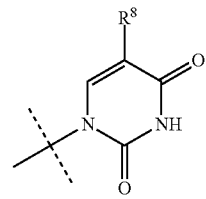
(b')

wherein $R^8$ is H or F.

5. The compound according to claim 4, wherein $R^8$ is H.

6. The compound according to claim 1, wherein U is O.

7. The compound according to claim 1 wherein $R^3$ is $C_1$-$C_6$alkoxy or NHC($R^{15}$)($R^{15'}$)C(=O)$R^{16}$.

8. The compound according to claim 1, wherein $R^2$ is H.

9. A pharmaceutical composition comprising a compound according to claim 1 in association with a pharmaceutically acceptable adjuvant, diluent or carrier.

10. A pharmaceutical composition comprising a compound according to claim 1, further comprising one or more additional other antiviral agent(s).

11. A method for the treatment of hepatitis C virus infection comprising the administration of a compound according to claim 1 to a patient in need thereof.

12. The compound according to claim 7, wherein $R^3$ is $C_1$-$C_3$alkoxy.

13. The compound according to claim 12 wherein $R^3$ is isopropoxy or methoxy.

14. The compound according to claim 7, wherein one of $R^{15}$ and $R^{15'}$ is H and the other is methyl, isopropyl, isobutyl or 1-methylprop-1-yl.

15. The compound according to claim 14, wherein one of $R^{15}$ and $R^{15'}$ is H and the other is methyl.

16. The compound according to claim 7, wherein $R^{16}$ is straight or branched $C_1$-$C_6$ alkyl or $C_3$-$C_7$ alkyl.

17. The compound according to claim 16, wherein $R^{16}$ is isopropyl.

\* \* \* \* \*